(12) United States Patent
Cojocaru et al.

(10) Patent No.: US 8,999,335 B2
(45) Date of Patent: Apr. 7, 2015

(54) COMPOSITIONS AND METHODS FOR TREATMENT OF DRUG RESISTANT MULTIPLE MYELOMA

(75) Inventors: Gad S. Cojocaru, Ramat HaSharon (IL); Haiming Chen, West Hillls, CA (US); James Berenson, Beverly Hills, CA (US)

(73) Assignee: Compugen Ltd., Tel Aviv (IL)

(*) Notice: Subject to any disclaimer, the term of this patent is extended or adjusted under 35 U.S.C. 154(b) by 0 days.

(21) Appl. No.: 13/821,176

(22) PCT Filed: Sep. 16, 2011

(86) PCT No.: PCT/IB2011/054060
§ 371 (c)(1),
(2), (4) Date: Jun. 21, 2013

(87) PCT Pub. No.: WO2012/035518
PCT Pub. Date: Mar. 22, 2012

(65) Prior Publication Data
US 2013/0266510 A1  Oct. 10, 2013

Related U.S. Application Data

(60) Provisional application No. 61/383,784, filed on Sep. 17, 2010.

(51) Int. Cl.
| A61K 39/00 | (2006.01) |
| A61K 39/395 | (2006.01) |
| A61K 31/713 | (2006.01) |
| C07K 16/30 | (2006.01) |
| C12N 15/113 | (2010.01) |
| G01N 33/574 | (2006.01) |
| A61K 45/06 | (2006.01) |
| C12Q 1/68 | (2006.01) |
| G01N 33/68 | (2006.01) |

(52) U.S. Cl.
CPC ........... *A61K 39/3955* (2013.01); *A61K 31/713* (2013.01); *A61K 39/39558* (2013.01); *A61K 2039/505* (2013.01); *C07K 16/3061* (2013.01); *C07K 2317/73* (2013.01); *C07K 2317/732* (2013.01); *C07K 2317/77* (2013.01); *C07K 2319/30* (2013.01); *C12N 15/1138* (2013.01); *C12N 2310/11* (2013.01); *C12N 2310/12* (2013.01); *C12N 2310/14* (2013.01); *G01N 33/57426* (2013.01); *A61K 45/06* (2013.01); *C12Q 1/6886* (2013.01); *G01N 33/6893* (2013.01)

(58) Field of Classification Search
CPC ........... A61K 31/713; A61K 2039/505; A61K 39/00; G01N 33/6893; C07K 16/3061; C07K 2317/73; C07K 2317/732; C07K 2317/77; C07K 2319/30; C07K 16/28; C07K 16/30; C07K 2317/55; C12N 15/1138; C12N 2310/11; C12N 2310/12; C12N 2310/14
See application file for complete search history.

(56) References Cited

U.S. PATENT DOCUMENTS

| 6,979,557 | B2 | 12/2005 | Isogai et al. | |
|---|---|---|---|---|
| 7,411,051 | B2 | 8/2008 | Rosen et al. | |
| 2003/0219741 | A1 | 11/2003 | Isogai et al. | |
| 2004/0241803 | A1 | 12/2004 | Rosen et al. | |
| 2006/0068405 | A1 | 3/2006 | Diber et al. | |
| 2007/0015163 | A1 | 1/2007 | Isogai et al. | |
| 2007/0037741 | A1 | 2/2007 | Baldwin et al. | |
| 2007/0224663 | A1 | 9/2007 | Rosen et al. | |
| 2008/0057519 | A1* | 3/2008 | McWhirter | 435/7.23 |
| 2010/0144538 | A1 | 6/2010 | Belouchi et al. | |
| 2010/0286048 | A1 | 11/2010 | Rosen et al. | |
| 2011/0059471 | A1 | 3/2011 | Yamashiro et al. | |

FOREIGN PATENT DOCUMENTS

| EP | 1293569 A2 | 3/2003 |
|---|---|---|
| EP | 2264071 A1 | 12/2010 |
| WO | 02070539 A2 | 9/2002 |
| WO | 03090694 A2 | 11/2003 |
| WO | 2004081199 A2 | 9/2004 |
| WO | 2004/110369 A2 | 12/2004 |
| WO | 2006020266 A2 | 2/2006 |
| WO | 2008112177 A2 | 9/2008 |
| WO | WO 2009113649 A1 * | 9/2009 |
| WO | 2010067308 A2 | 6/2010 |

OTHER PUBLICATIONS

ISR for PCT/IB2011/054060 mailed Feb. 1, 2012.
PCT search report for parent PCT Application No. PCT/IB2009/055585, mailed Jun. 22, 2010.
Office action for corresponding EP Application No. 09799402.4, mailed Jan. 25, 2013.
OA for IL 213300 mailed Aug. 22, 2013.
ER for AU 2009325878 mailed Jul. 3, 2013.
Genbank accession No. AAH60775.1; from 2002.
Genbank accession No. AAH19600.1; from 2002.
NCBI accession No. NP_689893.1; from 2007.
Genbank Accession No. EAX04974.1; from 2001.
Genbank Accession No. EAX04975.1; from 2001.
Office action for corresponding Chinese Application No. 200980155730.6. mailed on Mar. 15 2013.
Office action for corresponding Chinese Application No. 200980155730.6. mailed on Oct. 31 2013.
Office Action for IL 213300 mailed Mar. 23, 2014.

* cited by examiner

*Primary Examiner* — Daniel C Gamett
(74) *Attorney, Agent, or Firm* — Graeser Associates International Inc; Dvorah Graeser

(57) ABSTRACT

This invention relates to a novel target for production of immune and non-immune based therapeutics and for disease diagnosis. More particularly, the invention provides therapeutic antibodies against TMEM154 antigens, which are differentially expressed in cancer, and diagnostic and therapeutic usages, wherein the cancer is relates to multiple myeloma, including multiple myeloma precursor diseases. This invention further relates to extracellular domains of TMEM154 proteins and variants, and therapeutic usages thereof.

11 Claims, 20 Drawing Sheets

ATGCAGGCTCCCCGCGCAGCCCTAGTCTTCGCCCTGGTGATCGCGCTCGTTCCCGTCGGCCGG
GGTAATTATGAGGAATTAGAAAACTCAGGAGATACAACTGTGGAATCTGAAAGACCAAATAAA
GTGACTATTCCAAGCACATTTGCTGCAGTGACCATCAAAGAAACATTAAATGCAAATATAAAT
TCTACCAACTTTGCTCCGGATGAAAATCAGTTAGAGTTTATACTGATGGTGTTAATCCCATTG
ATTTTATTGGTCCTCTTACTTTTATCCGTGGTATTCCTTGCAACATACTATAAAAGAAAAAGAA
CTAAACAAGAACCTTCTAGCCAAGGATCTCAGAGTGCTTTACAGACATATGAACTGGGAAGT
GAAAACGTGAAAGTCCCTATTTTTGAGGAAGATACACCCTCTGTTATGGAAATTGAAATGGA
AGAGCTTGATAAATGGATGAACAGCATGAATAGAAATGCCGACTTTGAATGTTTACCTACCTT
GAAGGAAGAGAAGGAATCAAATCACAACCCAAGTGACAGTGAATCCGACTACAAAGACGAT
GACGACAAGTAA

FIG. 3

MQAPRAALVFALVIALVPVGRGNYEELENSGDTTVESERPNKVTIPSTFA
AVTIKETLNANINSTNFAPDENQLEFILMVLIPLILLVLLLLSVVFLATY
YKRKRTKQEPSSQGSQSALQTYELGSENVKVPIFEEDTPSVMEIEMEELD
KWMNSMNRNADFECLPTLKEEKESNHNPSDSESDYKDDDDK

FIG. 4

COMPOSITIONS AND METHODS FOR TREATMENT OF DRUG RESISTANT MULTIPLE MYELOMA

FIELD OF THE INVENTION

The present invention relates to compositions and methods for treatment of drug resistant cancer, and in particular, but not exclusively, to TMEM154 related polypeptides and polynucleotides as suitable targets and/or candidates for development of therapeutics and diagnostics, particularly for cancer therapy and treatment of immune related disorders.

BACKGROUND OF THE INVENTION

Tumor antigens are ideally positioned as biomarkers and drug targets, and they play a critical role in the development of novel strategies for active and passive immunotherapy agents, to be used as stand-alone therapies or in conjunction with conventional therapies for cancer. Tumor antigens can be classified as either tumor-specific antigens (TSAs) where the antigens are expressed only in tumor cells and not in normal tissues, or tumor-associated antigens (TAAs) where the antigens are overexpressed in tumor cells but nonetheless also present at low levels in normal tissues.

TAAs and TSAs are validated as targets for passive (antibody) therapy as well as active immunotherapy using strategies to break immune tolerance and stimulate the immune system. The antigenic epitopes that are targeted by these therapeutic approaches are present at the cell surface, overexpressed in tumor cells compared to non-tumor cells, and are targeted by antibodies that block functional activity, inhibit cell proliferation, or induce cell death.

There are a growing number of tumor-associated antigens against which monoclonal antibodies have been tested or are in use as treatment for cancer. The identification and molecular characterization of novel tumor antigens expressed by human malignancies is an active field in tumor immunology. Several approaches have been used to identify tumor-associated antigens as target candidates for immunotherapy, including high throughput bioinformatic approaches, based on genomics and proteomics. The identification of novel TAAs or TSAs expands the spectrum of tumor antigen targets available for immune recognition and provides new target molecules for the development of therapeutic agents for passive immunotherapy, including monoclonal antibodies, whether unmodified or armed.

Such novel antigens may also point the way to more effective therapeutic vaccines for active or adoptive immunotherapy.

Cancer vaccination involves the administration of tumor antigens and is used to break immune tolerance and induce an active T-cell response to the tumor. Vaccine therapy includes the use of naked DNA, peptides, recombinant protein, and whole cell therapy, where the patient's own tumor cells are used as the source of the vaccine. With the identification of specific tumor antigens, vaccinations are more often carried out by dendritic cell therapy, whereby dendritic cells are loaded with the relevant protein or peptide, or transfected with vector DNA or RNA.

The major applications of anti-TAA antibodies for treatment of cancer are therapy with naked antibody, therapy with enhanced effector function enhanced Antibody-Dependent Cell-Mediated Cytotoxicity (ADCC) or enhanced Complement dependent cytotoxicity (CDC), therapy with a drug-conjugated antibody, and fusion therapy with cellular immunity. Ever since their discovery, antibodies were envisioned as "magic bullets" that would deliver toxic agents, such as drugs, toxins, enzymes and radioisotopes, specifically to the diseased site and leaving the non-target normal tissues unaffected. Indeed, antibodies, and in particular antibody fragments, can function as carriers of cytotoxic substances such as radioisotopes, drugs and toxins. Immunotherapy with such immunoconjugates is more effective than with the naked antibody.

With the advent of antibody engineering, small molecular weight antibody fragments exhibiting improved tumor penetration have been generated. Such antibody fragments are often conjugated to specific cytotoxic molecules and are designed to selectively deliver them to cancer cells. Still, solid tumors remain a formidable challenge for therapy, even with immunoconjugated antibody fragments.

The new wave of optimization strategies involves the use of biological modifiers to modulate the impediments posed by solid tumors. Thus, in combination to antibodies or their conjugated antibody fragments, various agents are being used to improve the tumor blood flow, enhance vascular permeability, lower tumor interstitial fluid pressure by modulating stromal cells and extracellular matrix components, upregulate expression of target antigens and improve penetration and retention of the therapeutic agent.

Immunotherapy with antibodies represents an exciting opportunity for combining with standard modalities, such as chemotherapy, as well as combinations with diverse biological agents to obtain a synergistic activity. Indeed, unconjugated mAbs are more effective when used in combination with other therapeutic agents, including other antibodies.

Passive tumor immunotherapy uses the exquisite specificity and lytic capability of the immune system to target tumor specific antigens and treat malignant disease with a minimum of damage to normal tissue. Several approaches have been used to identify tumor-associated antigens as target candidates for immunotherapy. The identification of novel tumor specific antigens expands the spectrum of tumor antigen targets available for immune recognition and provides new target molecules for the development of therapeutic agents for passive immunotherapy, including monoclonal antibodies, whether unmodified or armed. Such novel antigens may also point the way to more effective therapeutic vaccines for active or adoptive immunotherapy.

Drug resistance in general remains a significant problem for treatment of cancer, such as multiple myeloma (MM). Although patients with MM typically initially respond to current treatment modalities, it remains an incurable disease. Many new therapeutic options have become available during the past several years but nearly all patients develop resistance to currently available therapeutic options. In addition, there is no tumor marker that is uniformly expressed in all MM cells. For example, CD138 is considered to be present on the surface of tumor cells in most cases of MM, but generally is only present in a subset of the patients' tumor population, and may in fact be absent in the most resistant part of the tumor clone (J Clin Oncol, 21: 4239-4247, 2003).

BRIEF SUMMARY OF THE INVENTION

The background art fails to provide efficient therapies that for treatment of drug resistant cancer, such as drug resistant multiple myeloma and/or refractory multiple myeloma (MM), and/or an efficient tumor marker that is uniformly expressed in all MM cells.

The present invention, in at least some embodiments, is of a pharmaceutical composition comprising a polyclonal or monoclonal antibody, or antibody binding fragment, that specifically binds to a TMEM154 polypeptide comprising at least one of SEQ ID NOS: 10, 5, 62 or 63 in a pharmaceutically acceptable carrier, and a second medicament, wherein the second medicament is suitable for treatment of multiple myeloma, wherein the antibody and the second medicament are provided in a single dosage form or separately, and wherein the second medicament is selected for a synergistic effect between the antibody and the second medicament.

According to at least some embodiments there is provided use of the above composition for treatment of multiple myeloma. Optionally, the multiple myeloma is selected from the group consisting of a precursor to myeloma, multiple myeloma cancers which produce light chains of kappa-type and/or light chains of lambda-type; aggressive multiple myeloma; refractory multiple myeloma, and drug resistant multiple myeloma.

According to at least some embodiments there is provided use of a polyclonal or monoclonal antibody, or antibody binding fragment, that specifically binds to a TMEM154 polypeptide comprising at least one of SEQ ID NOS: 10, 5, 62 or 63, for treatment of a disease selected from the group consisting of a precursor to myeloma, multiple myeloma cancers which produce light chains of kappa-type and/or light chains of lambda-type; aggressive multiple myeloma; refractory multiple myeloma, and drug resistant multiple myeloma.

Optionally the aggressive multiple myeloma comprises primary plasma cell leukemia (PCL).

Optionally, such use further comprises use of another medicament for treatment of multiple myeloma, wherein the antibody and the other medicament are provided in a single dosage form or separately.

Optionally, such use further comprises use of another therapy in combination with the antibody.

Optionally the polyclonal or monoclonal antibody, or antibody binding fragment specifically binds to a TMEM154 polypeptide comprising SEQ ID NO: 10 or a fragment thereof.

Optionally the polyclonal or monoclonal antibody, or antibody binding fragment specifically binds to a TMEM154 polypeptide consisting essentially of SEQ ID NO: 10.

Optionally the antibody or fragment specifically binds to a polypeptide consisting essentially of an amino acid sequence of SEQ ID NO:5.

Optionally the antibody or fragment specifically binds to a peptide consisting essentially of at least one SEQ ID NOS: 62 or 63.

Optionally the antibody or fragment is selected from the group consisting of: a fully human antibody, a humanized or primatized antibody, a chimeric antibody, Fab, Fab', F(ab')2, F(ab'), F(ab), Fv or scFv fragment and minimal recognition unit.

Optionally the antibody or fragment is coupled to a detectable marker, or to an effector moiety.

Optionally the effector moiety is one or more of a radionuclide, fluorophore, an enzyme, a toxin, a therapeutic agent, a chemotherapeutic agent, a cytokine antibody, a cytokine receptor, or an immunomodulatory agent; or the detectable marker is one or more of a radioisotope, a metal chelator, an enzyme, a fluorescent compound, a bioluminescent compound or a chemiluminescent compound.

According to at least some embodiments there is provided use of an antibody or a fragment that specifically binds to a TMEM154 polypeptide comprising SEQ ID NO 10 or a fragment thereof for diagnosing a disease selected from the group consisting of a precursor to myeloma, multiple myeloma cancers which produce light chains of kappa-type and/or light chains of lambda-type; aggressive multiple myeloma; refractory multiple myeloma, and drug resistant multiple myeloma, the use comprising detecting in a sample obtained from a subject the presence of a polypeptide and/or an over expressed level of the polypeptide having an amino acid sequence comprising SEQ ID NO: 10 or a fragment thereof; wherein the over expressed level is determined with regard to a normal level of the polypeptide in a corresponding normal tissue.

Optionally the aggressive multiple myeloma comprises primary plasma cell leukemia (PCL).

Optionally the detection is conducted by immunoassay.

According to at least some embodiments there is provided an assay for detecting the presence of a polypeptide having an amino acid sequence consisting essentially of SEQ ID NO: 10 or a fragment thereof in a biological sample, comprising contacting an isolated sample from a subject with an antibody or a fragment that specifically binds to a TMEM154 polypeptide comprising SEQ ID NO: 10 or a fragment thereof, wherein a presence of the polypeptide having the amino acid sequence consisting essentially of SEQ ID NO:10 is indicative of a presence of a disease selected from the group consisting of a precursor to myeloma, multiple myeloma cancers which produce light chains of kappa-type and/or light chains of lambda-type; aggressive multiple myeloma; refractory multiple myeloma, and drug resistant multiple myeloma.

According to at least some embodiments there is provided a method for diagnosing a disease selected from the group consisting of a precursor to myeloma, multiple myeloma cancers which produce light chains of kappa-type and/or light chains of lambda-type; aggressive multiple myeloma, refractory multiple myeloma, and drug resistant multiple myeloma, in a subject, comprising detecting in the subject or in a sample obtained from the subject a polynucleotide and/or an overexpressed level of the polynucleotide having a sequence at least 85% homologous to the nucleic acid sequence as set forth in at least one of SEQ ID NOs:57, 1-4, 41, or a fragment thereof; wherein the overexpressed level is determined with regard to a normal level of the polynucleotide in a corresponding normal tissue.

Optionally diagnosing comprises screening for multiple myeloma in a subject, detecting a presence or a severity of multiple myeloma in a subject, distinguishing multiple myeloma from other diseases, providing prognosis of multiple myeloma, monitoring progression or relapse of multiple myeloma, in a subject, assessment of treatment efficacy or relapse of multiple myeloma, in a subject, selecting a therapy and a treatment for multiple myeloma, in a subject, optimization of a given therapy for multiple myeloma, in a subject, monitoring the treatment of multiple myeloma, in a subject, predicting the suitability of a therapy for specific patients or subpopulations, determining the appropriate dosing of a therapeutic product in patients or subpopulations.

Optionally the aggressive multiple myeloma comprises primary plasma cell leukemia (PCL).

According to at least some embodiments there is provided a siRNA, antisense RNA, or ribozyme that binds the transcript according to any of SEQ ID NOs:57, 1-4, 41, or a fragment thereof, and inhibits its expression, adapted for treatment or diagnosis of multiple myeloma.

Optionally, the precursor form of the disease is selected from the group consisting of MGUS (monoclonal gammopathy of undetermined significance), Waldenström's macroglobulinemia (WM, also known as lymphoplasmacytic lymphoma) which may proceed to multiple myeloma; smoldering multiple myeloma (SMM), indolent multiple myeloma, and premalignant forms of multiple myeloma which may also proceed to multiple myeloma.

As described in greater detail below, the terms "polypeptides" and "proteins" are used to describe specific variants, the known proteins themselves or derived amino acid sequences related to TMEM154, or fragments or portions of any of the above. According to at least some embodiments of the present invention, the TMEM154 proteins are differentially expressed by Multiple Myeloma, and therefore are suitable targets for treatment and diagnosis of Multiple Myeloma, and drug development.

By "multiple myeloma" it is meant any type of B-cell malignancy characterised by the accumulation of terminally differentiated B-cells (plasma cells) in the bone marrow, including multiple myeloma cancers which produce light chains of kappa-type and/or light chains of lambda-type; drug resistant multiple myeloma, refractor multiple myeloma or aggressive multiple myeloma, including primary plasma cell leukemia (PCL); and/or optionally including any precursor forms of the disease, including but not limited to benign plasma cell disorders such as MGUS (monoclonal gammopathy of undetermined significance) and/or Waldenström's macroglobulinemia (WM, also known as lymphoplasmacytic lymphoma) which may proceed to multiple myeloma; and/or smoldering multiple myeloma (SMM), and/or indolent multiple myeloma, premalignant forms of multiple myeloma which may also proceed to multiple myeloma. With regard to premalignant or benign forms of the disease, optionally the compositions and methods thereof may be applied for prevention, in addition to or in place of treatment, for example optionally to halt the progression of the disease to a malignant form of multiple myeloma.

It should be noted that TMEM154 proteins and discrete portions thereof were originally disclosed in PCT Application No. WO 2010/067308, owned in common with the present application, which is hereby incorporated by reference as if fully set forth herein. According to at least some embodiments, the subject invention provides isolated polypeptides comprising the soluble ectodomain (ECD) of the TMEM154 proteins and fragments and conjugates thereof, as well as nucleic acid sequences encoding said soluble ectodomain, and the use thereof as therapeutic agents for Multiple Myeloma, aggressive and/or drug resistant multiple myeloma and/or refractory multiple myeloma therapy, and drug development.

As used herein, the term "diagnosis of a disease" encompasses screening for a disease, diagnosing a diseases, detecting the presence or a severity of a disease, prognosis of a diseases, monitoring of disease progression and/or treatment efficacy and/or relapse of a disease, disorder or condition, as well as selecting a therapy and/or a treatment for a disease, optimization of a given therapy for a disease, monitoring the treatment of a disease, and/or predicting the suitability of a therapy for specific patients or subpopulations or determining the appropriate dosing of a therapeutic product in patients or subpopulations.

According to one embodiment, detecting the presence of the polypeptide or polynucleotide is indicative of the presence of the disease and/or its severity and/or its progress. According to another embodiment, a change in the expression and/or the level of the polynucleotide or polypeptide compared to its expression and/or level in a healthy subject or a sample obtained therefrom is indicative of the presence of the disease and/or its severity and/or its progress. According to a further embodiment, a change in the expression and/or level of the polynucleotide or polypeptide compared to its level and/or expression in said subject or in a sample obtained therefrom at earlier stage is indicative of the progress of the disease. According to still further embodiment, detecting the presence and/or relative change in the expression and/or level of the polynucleotide or polypeptide is useful for selecting a treatment and/or monitoring a treatment of the disease (multiple myeloma). According to still further embodiment, detecting the presence and/or relative change in the expression and/or level of the polynucleotide or polypeptide is useful for prediction of the suitability of a therapeutic product for specific patients or subpopulations or for determining the appropriate dosing of a therapeutic product in patients or subpopulations. According to still further embodiment, the method comprising quantitatively and/or qualitatively determining or assessing expression of the polypeptides and/or polynucleotides, whereby differences in expression from an index sample, or a sample taken from a subject prior to the initiation of the therapy, or during the course of therapy, is indicative of the efficacy, or optimal activity of the therapy.

In at least some embodiments of the present invention, the methods are conducted on a whole body.

In at least some embodiments of the present invention, the methods are conducted with a sample isolated from a subject having, predisposed to, or suspected of having any one or more of the above types of multiple myeloma (including without limitation its precursor diseases). In at least some embodiments of the present invention, the sample is a cell or tissue or a body fluid sample.

In at least some embodiments, the subject invention therefore also relates to diagnostic methods and or assays for diagnosis a disease optionally in a biological sample taken from a subject (patient), which is optionally some type of body fluid or secretion including but not limited to seminal plasma, blood, serum, urine, prostatic fluid, seminal fluid, semen, the external secretions of the skin, respiratory, intestinal, and genitourinary tracts, tears, cerebrospinal fluid, sputum, saliva, milk, peritoneal fluid, pleural fluid, cyst fluid, broncho alveolar lavage, lavage of the reproductive system and/or lavage of any other part of the body or system in the body, and stool or a tissue sample. The term may also optionally encompass samples of in vivo cell culture constituents. The sample can optionally be diluted with a suitable eluant before contacting the sample to an antibody and/or performing any other diagnostic assay.

According to at least some embodiments of the present invention there are provided diagnostic methods that include the use of any of the foregoing antibodies according to at least some embodiments of the present invention, by way of example in immunohistochemical assay, radioimaging assays, in-vivo imaging, positron emission tomography (PET), single photon emission computer tomography (SPECT), magnetic resonance imaging (MRI), Ultra Sound, Optical Imaging, Computer Tomography, radioimmunoassay (RIA), ELISA (enzyme-linked immunosorbent assay), slot blot, competitive binding assays, fluorimetric imaging assays, Western blot, FACS, and the like.

According to at least some embodiments of the present invention there are provided diagnostic methods that include the detection of at least one of TMEM154 polynucleotides, selected from the group consisting of SEQ ID NOs: 57, 1-4, 41, or a fragment or a variant or a homolog thereof, by employing a NAT-based technology.

In at least some embodiments of the present invention, the NAT-based assay is selected from the group consisting of a PCR, Real-Time PCR, LCR, Self-Sustained Synthetic Reaction, Q-Beta Replicase, Cycling Probe Reaction, Branched DNA, RFLP analysis, DGGE/TGGE, Single-Strand Conformation Polymorphism, Dideoxy Fingerprinting, Microarrays, Fluorescence In Situ Hybridization or Comparative Genomic Hybridization.

In at least some embodiments of the present invention, the kit comprises markers and reagents for detecting the changes by employing a NAT-based technology.

In at least some embodiments of the present invention, the kit comprises at least one nucleotide probe or primer. In at least some embodiments of the present invention, the kit comprises at least one primer pair capable of selectively hybridizing to a nucleic acid sequence according to the teaching of the present invention. In at least some embodiments of the present invention, the kit comprises at least one oligonucleotide capable of selectively hybridizing to a nucleic acid sequence according to the teaching of the present invention.

In at least some embodiments of the present invention, the kit comprises an antibody capable of recognizing or interacting with a polypeptide or protein according to at least some embodiments of the present invention. In at least some embodiments of the present invention, the kit further comprises at least one reagent for performing an immunohistochemical assay, radioimaging assays, in-vivo imaging, positron emission tomography (PET), single photon emission computer tomography (SPECT), magnetic resonance imaging (MRI), Ultra Sound, Optical Imaging, Computer Tomography, radioimmunoassay (RIA), ELISA, slot blot, competitive binding assays, fluorimetric imaging assays, Western blot, FACS, and the like.

According to at least some embodiments of the present invention, there is provided use of a isolated polypeptide of TMEM154 ectodomain (ECD), or fragment or variant thereof that possesses at least 95% sequence identity therewith, for treatment of multiple myeloma (according to any subtype or precursor as described herein).

Optionally the ECD comprises SEQ ID NO:10. Optionally, the TMEM154 ECD refers to any one of the polypeptide sequences below or fragments thereof: ECD region of the polypeptide W38346_P3 (SEQ ID NO:5):
W38346_P3_23-75 (SEQ ID NO:10)-sequence: EELENSGDTTVESERPNKVTIPSTFAAVTIKETLNANINSTNFAPDENQLE (and optionally bridging amino acids of any of one, two, three, four, five, six, seven, eight, nine or 10 amino acids on either side, starting anywhere from residue 13 and ending anywhere up to residue 85; and also non-linear epitopes incorporating this sequence or a portion thereof, as well as any of one, two, three, four, five, six, seven, eight, nine or 10 non-contiguous amino acids of the sequence);
ECD region of the polypeptide W38346_P4 (SEQ ID NO:8):
W38346_P4_20-105 (SEQ ID NO:11)-sequence: ATYYKRKRTKQEPSSQGSQSALQTYELGSENVKVPIFEEDTPSVMEIEMEELDKWMNSMRNADFECLPTLKEEKESNHNPSDSES (and optionally bridging amino acids of any of one, two, three, four, five, six, seven, eight, nine or 10 amino acids on either side, starting anywhere from residue 10 and ending anywhere up to residue 115; and also non-linear epitopes incorporating this sequence or a portion thereof, as well as any of one, two, three, four, five, six, seven, eight, nine or 10 non-contiguous amino acids of the sequence);
ECD region of the polypeptide W38346_P7 (SEQ ID NO:9):
W38346_P7_23-75 (SEQ ID NO:10)-sequence: EELENSGDTTVESERPNKVTIPSTFAAVTIKETLNANINSTNFAPDENQLE (and optionally bridging amino acids of any of one, two, three, four, five, six, seven, eight, nine or 10 amino acids on either side, starting anywhere from residue 13 and ending anywhere up to residue 85; and also non-linear epitopes incorporating this sequence or a portion thereof, as well as any of one, two, three, four, five, six, seven, eight, nine or 10 non-contiguous amino acids of the sequence);
and fragments and variants and homologs thereof possessing at least 80%, at least 85%, at least 90%, at least 95, at least 96, at least 97, at least 98 or at least 99% sequence identity therewith.

The TMEM154 extracellular domain can contain one or more amino acids from the signal peptide or the putative transmembrane domain of TMEM154. During secretion, the number of amino acids of the signal peptide that are cleaved can vary depending on the expression system and the host. Additionally or alternatively, fragments of TMEM154 extracellular domain missing one or more amino acids from the C-terminus or the N-terminus that retain the ability to bind to the TMEM154 receptor can be used as a fusion partner for the disclosed fusion proteins.

Optionally the polypeptide is fused to a non-TMEM154 protein sequence, or attached to a detectable or therapeutic moiety, fused together directly or indirectly via a peptide linker sequence or a chemical linker. Optionally the non-TMEM154 protein is at least a portion of an immunoglobulin molecule.

Optionally the fusion protein comprises an immunoglobulin heavy chain constant region corresponding to an antibody isotype selected from the group consisting of an IgG1, IgG2, IgG3, IgG4, IgM, IgE, IgA and IgD.

Optionally the immunoglobulin constant domain comprises the hinge, CH2 and CH3 regions of a human IgG immunoglobulin, selected from the group consisting of Cγ1, Cγ2, Cγ3 and Cγ4 chain.

Optionally the fusion protein further comprises a domain that mediates dimerization or multimerization of the fusion protein to form homodimers, heterodimers, homomultimers, or heteromultimers.

Optionally the domain that mediates dimerization or multimerization is selected from the group consisting of one or more cysteines that are capable of forming an intermolecular disulfide bond with a cysteine on the partner fusion protein, a coiled-coil domain, an acid patch, a zinc finger domain, a calcium hand domain, a CHI region, a CL region, a leucine zipper domain, an SH2 (src homology 2) domain, an SH3 (src Homology 3) domain, a PTB (phosphotyrosine binding) domain, a WW domain, a PDZ domain, a 14-3-3 domain, a WD40 domain, an EH domain, a Lim domain, an isoleucine zipper domain, and a dimerization domain of a receptor dimer pair.

Optionally, the fusion proteins are bound together by disulfide bonds.

Optionally, multiple myeloma comprises one or more of a precursor form of the disease, multiple myeloma cancers which produce light chains of kappa-type and/or light chains of lambda-type; aggressive multiple myeloma, refractory multiple myeloma, and drug resistant multiple myeloma. Optionally, the precursor form of the disease is selected from the group consisting of MGUS (monoclonal gammopathy of undetermined significance), Waldenström's macroglobulinemia (WM, also known as lymphoplasmacytic lymphoma) which may proceed to multiple myeloma; smoldering multiple myeloma (SMM), indolent multiple myeloma, and premalignant forms of multiple myeloma which may also proceed to multiple myeloma. Optionally the aggressive multiple myeloma comprises primary plasma cell leukemia (PCL).

All nucleic acid sequences and/or amino acid sequences, according to at least some embodiments of the invention, relate to their isolated form.

It should be noted that oligonucleotide and polynucleotide, or peptide, polypeptide and protein, may optionally be used interchangeably.

BRIEF DESCRIPTION OF THE FIGURES

FIGS. 6A and 6B present the results obtained using TM21 antibodies purified from rabbit #6285 and rabbit #6286, respectively.

FIGS. 7A and 7B present the results obtained using TM101 antibodies purified from rabbit #6248 and rabbit #6249, respectively.

FIGS. 8A and 8B present the results obtained using TM21 antibodies purified from rabbit #6285 and rabbit #6286, respectively. FIG. 8C presents the results obtained using TM101 antibodies purified from rabbit #6249.

FIGS. 9A-1-9A-4 present the results on CESS (ATCC cat no TIB-190) calls; FIGS. 9B-1-9B-3 present the results on Ramos (ATCC cat no CRL-1923) cells; and FIGS. 9C-1-9C-3 present the results on Daudi (ATCC cat no CCL-213) cells. FIGS. 9A-1 and 9A-2 present the results obtained using TM21 antibodies purified from rabbit #6285 and rabbit #6286, respectively. FIGS. 9A-3 and 9A-4 present the results obtained using TM101 antibodies purified from rabbit #6248 and rabbit #6249, respectively. FIGS. 9B-1 and 9B-2 present the results obtained using TM21 antibodies purified from rabbit #6285 and rabbit #6286, respectively. FIG. 9B-3 presents the results obtained using TM101 antibodies purified from rabbit #6248. FIGS. 9C-1 and 9C-2 present the results obtained using TM21 antibodies purified from rabbit #6285 and rabbit #6286, respectively. FIG. 9C-3 presents the results obtained using TM101 antibodies purified from rabbit #6248.

DETAILED DESCRIPTION OF THE INVENTION

Figure 1A:
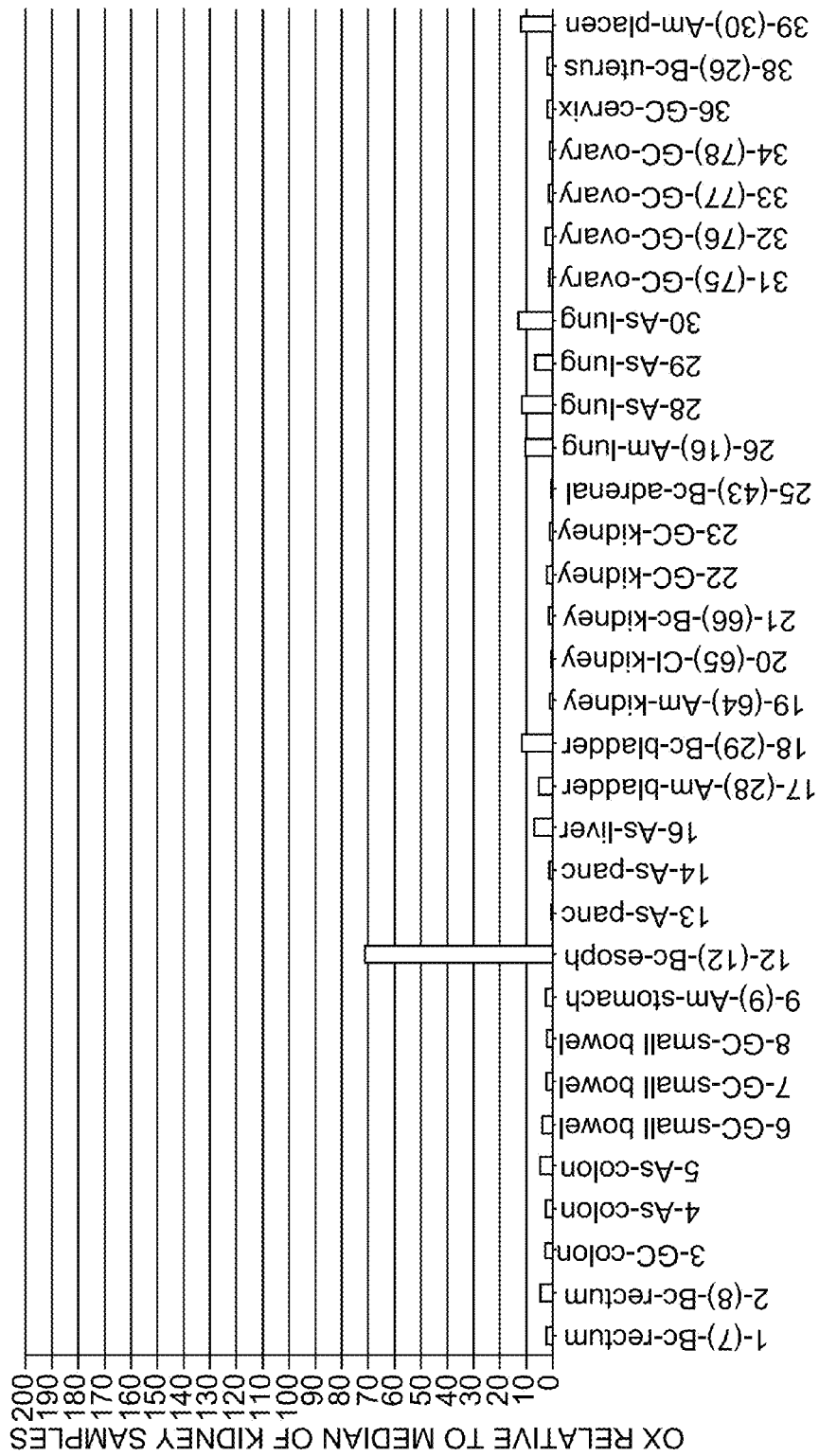
FIGS. 1A and 1B show a histogram showing the expression of TMEM154 W38346 transcripts which are detectable by amplicon as depicted in sequence name W38346_seg6-20F1R1 (SEQ ID NO:41) in different normal tissues (FIG. 1B is a continuation of FIG. 1A).
Figure 1B:
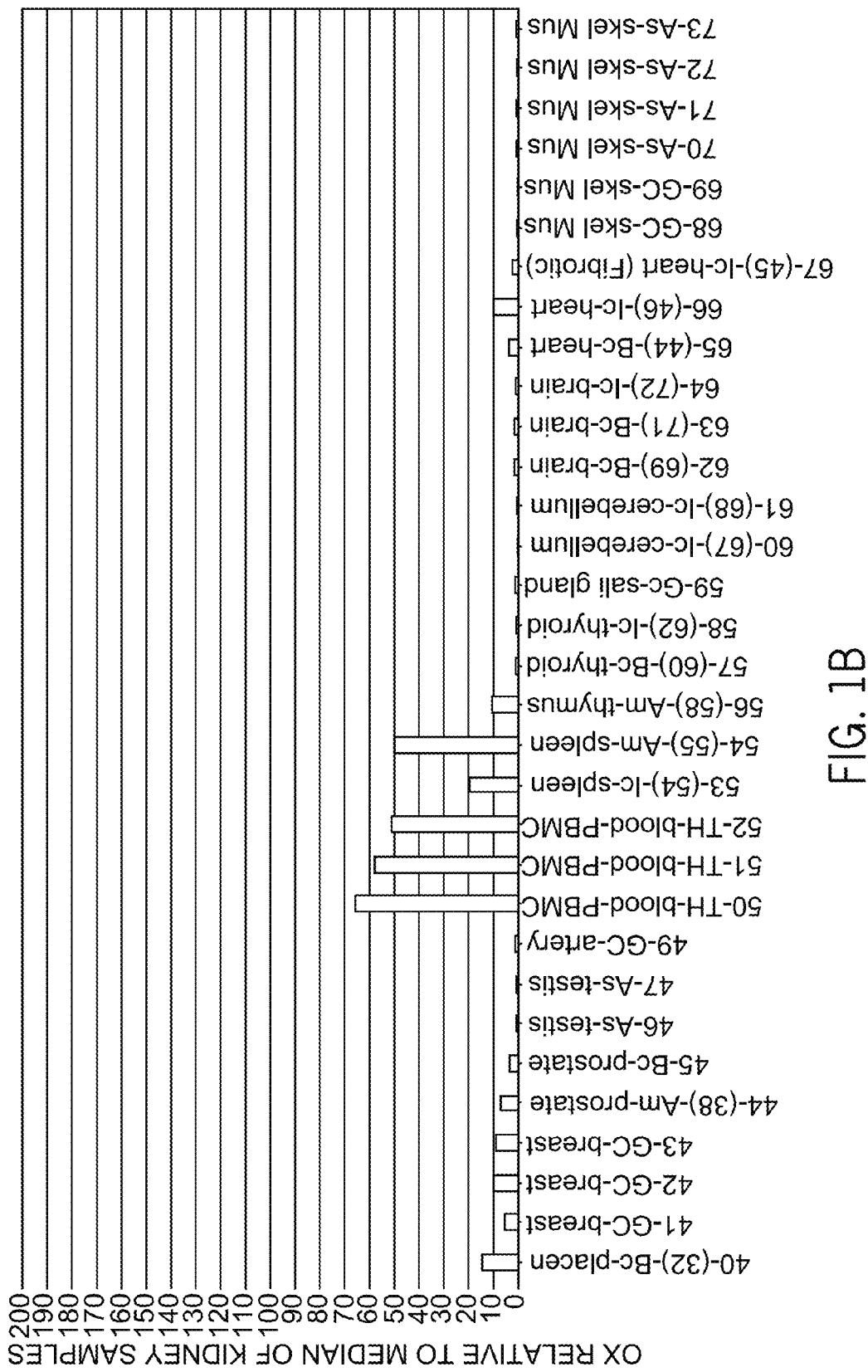
Figure 2A:
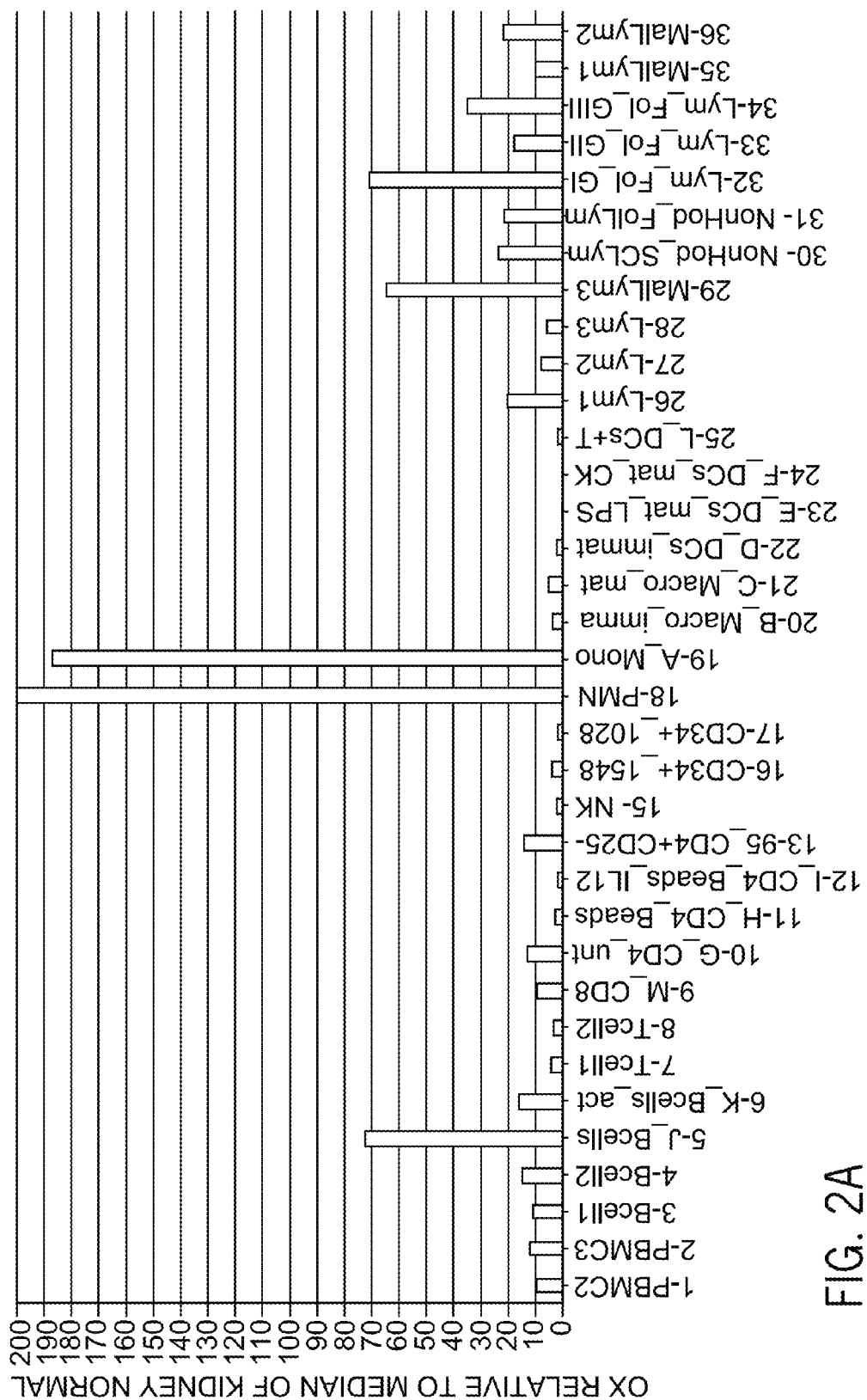
FIGS. 2A and 2B show a histogram showing the expression of TMEM154 W38346 transcripts which are detectable by amplicon as depicted in sequence name W38346_seg6-20F1R1 (SEQ ID NO:41) in blood specific panel (FIG. 2B is a continuation of FIG. 2A).
Figure 2B:
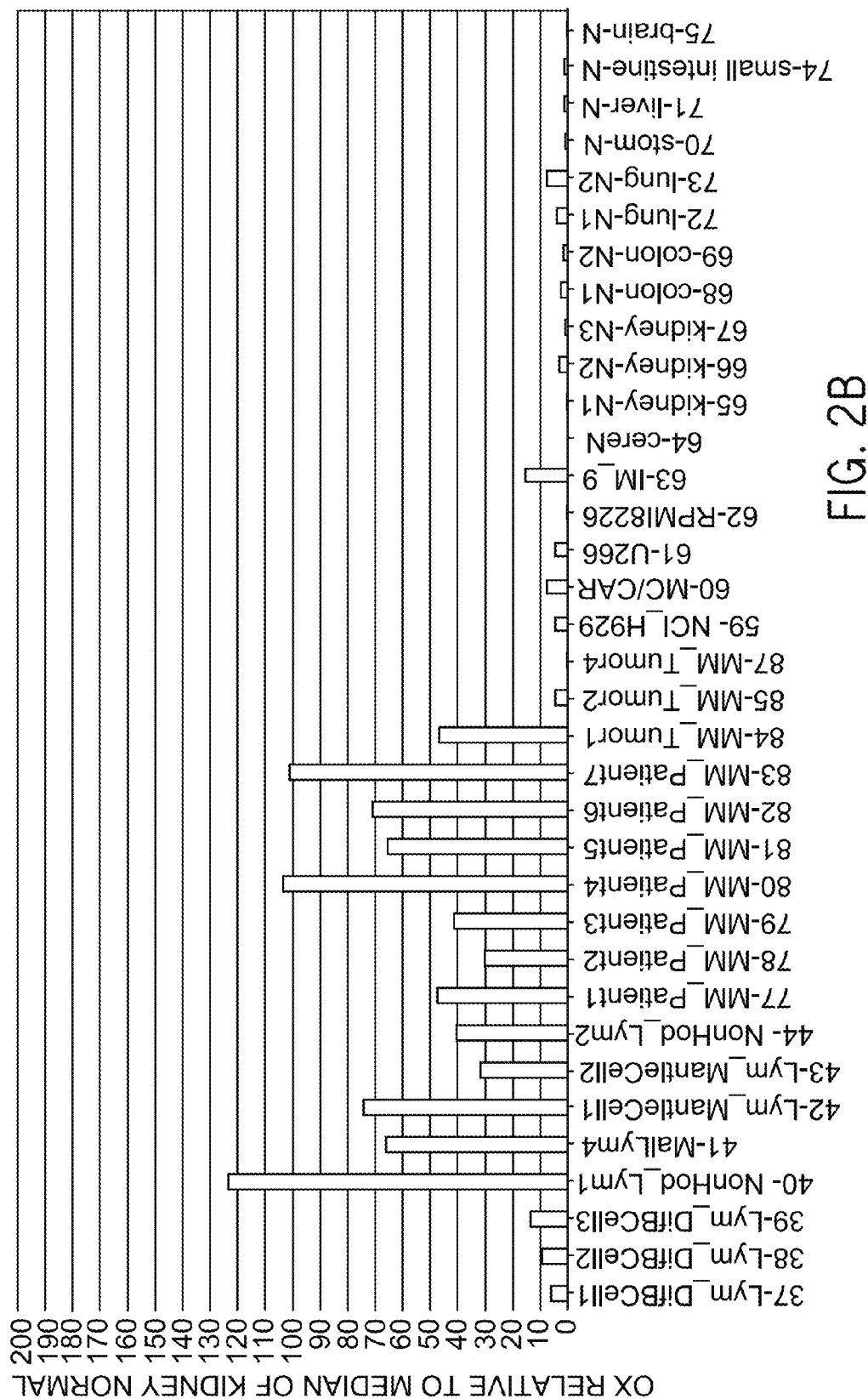

According to at least some embodiments of the present invention, there is provided a pharmaceutical composition comprising a polyclonal or monoclonal antibody, or antibody binding fragment, that specifically binds to a TMEM154 polypeptide comprising at least one of SEQ ID NOS: 5, 10, 62 or 63, or a fragment thereof, in a pharmaceutically acceptable carrier, and a second medicament, wherein said second medicament is suitable for treatment of multiple myeloma, wherein said antibody and said second medicament are provided in a single dosage form or separately, and wherein said second medicament is selected for a synergistic effect between said antibody and said second medicament. Optionally a dosage form of one or both of said antibody and said second medicament is selected for said synergistic effect.

The composition is optionally and preferably used for treatment of multiple myeloma, in which multiple myeloma is preferably selected from the group consisting of a precursor to myeloma, multiple myeloma cancers which produce light chains of kappa-type and/or light chains of lambda-type; aggressive multiple myeloma; refractory multiple myeloma, and drug resistant multiple myeloma.

According to at least some other embodiments of the present invention, there is provided use of a polyclonal or monoclonal antibody, or antibody binding fragment, that specifically binds to a TMEM154 polypeptide comprising at least one of SEQ ID NOS: 5, 10, 62 or 63, or a fragment thereof, for treatment of a disease selected from the group consisting of a precursor to myeloma, multiple myeloma cancers which produce light chains of kappa-type and/or light chains of lambda-type; aggressive multiple myeloma; refractory multiple myeloma, and drug resistant multiple myeloma.

Optionally aggressive multiple myeloma comprises primary plasma cell leukemia (PCL). Also optionally another medicament for treatment of multiple myeloma is provided, wherein said antibody and said other medicament are provided in a single dosage form or separately. The precursor form of multiple myeloma may optionally be any precursor form of the disease as described herein.

In order that the present invention may be more readily understood, certain terms are first defined. Additional definitions are set forth throughout the detailed description.

The term "TMEM154 protein", as used herein, includes any protein encoded by a TMEM154 gene product, including the known or "wild type" protein, any splice variants thereof, any other variants thereof, or any fragments thereof (including but not limited to any extracellular portions thereof).

The term "TMEM154 polypeptide", as used herein, refers to a polypeptide encoded by any one of the nucleic acid sequences set forth in any one of SEQ ID NOs:1-4, 41, 57, and fragments and homologous thereof, especially those possessing at least 80, 85, 90, 95, 96, 97, 98, 99% sequence identity therewith. These nucleic acid sequences are referred to herein as "TMEM154 polynucleotide". The term also refers to any one of the polypeptides set forth in any one of SEQ ID NOs:5-9; extracellular portions thereof, set forth in any one of SEQ ID NOs:10, 11; unique bridge, edge portion, tail or head portion thereof, set forth in any one of SEQ ID NOs: 55, 56; protein fragments selected from any of the isolated polypeptides, used for rabbit immunization and specific antibodies production, set forth in any one of SEQ ID NOs:62, 63; and fragments and homologous thereof, especially those possessing at least 80, 85, 90, 95, 96, 97, 98, 99% sequence identity therewith. The term "TMEM154 polynucleotide" or "TMEM154 polypeptide", as used herein, further refers to any one of the foregoing polynucleotides and polypeptides, respectively, that are differentially expressed e.g., in multiple myeloma, aggressive and/or drug resistant and/or refractory multiple myeloma.

As used herein the term "soluble TMEM154" or "soluble ectodomain (ECD)" or "ectodomain" or "soluble TMEM154 proteins/molecules" refers to fragments of TMEM154 that include some or all of the extracellular domain of the TMEM154 polypeptide, and lack some or all of the intracellular and/or transmembrane domains. In one embodiment, soluble TMEM154 polypeptide fragments include the entire extracellular domain of the TMEM154 polypeptide. In other embodiments, the soluble fragments of TMEM154 polypeptides include fragments of the extracellular domain.

As used herein, the term "soluble TMEM154" or "soluble ectodomain (ECD)" or "ectodomain" or "soluble TMEM154 proteins/molecules" further means non-cell-surface-bound (i.e. circulating) TMEM154 molecules or any portion of a TMEM154 molecule including, but not limited to: TMEM154 polypeptides, fragments or fusions proteins thereof fusion proteins, wherein the extracellular domain of TMEM154 is fused to an immunoglobulin (Ig) moiety rendering the fusion molecule soluble, or fragments and derivatives thereof, proteins with the extracellular domain of TMEM154 fused or joined with a portion of a biologically active or chemically active protein such as the papillomavirus E7 gene product, melanoma-associated antigen p97 or HIV env protein, or fragments and derivatives thereof; hybrid (chimeric) fusion proteins such as TMEM154 polypeptides, fragments or fusions proteins thereof, or fragments and derivatives thereof. "Soluble TMEM154 proteins/molecules" also include TMEM154 molecules with the transmembrane domain removed to render the protein soluble, or fragments and derivatives thereof; and soluble TMEM154 mutant molecules. The soluble TMEM154 molecules used in the methods of the invention may or may not include a signal (leader) peptide sequence.

The term the "soluble ectodomain (ECD)" or "ectodomain" or "soluble" form of TMEM154 refers also to the nucleic acid sequences encoding the corresponding proteins of TMEM154 "soluble ectodomain (ECD)" or "ectodomain" or "soluble TMEM154 proteins/molecules"). Optionally, the TMEM154 ECD refers to any one of the polypeptide sequences below or fragments thereof: ECD region of the polypeptide W38346_P3 (SEQ ID NO:5): W38346_P3__23-75 (SEQ ID NO:10)-sequence: EELENS-GDTTVESERPNKVTIPSTFAAVTIKETL-NANINSTNFAPDENQLE (and optionally bridging amino acids of any of one, two, three, four, five, six, seven, eight, nine or 10 amino acids on either side, starting anywhere from residue 13 and ending anywhere up to residue 85; and also non-linear epitopes incorporating this sequence or a portion thereof, as well as any of one, two, three, four, five, six, seven, eight, nine or 10 non-contiguous amino acids of the sequence);

ECD region of the polypeptide W38346_P4 (SEQ ID NO:8): W38346_P4__20-105 (SEQ ID NO:11)-sequence: ATYYKRKRTKQEPSSQGSQSALQTYELG-SENVKVPIFEEDTPSVMEIEMEELDKW-MNSMNRNADFECLPTLKEEKESNHNPSDSES (and optionally bridging amino acids of any of one, two, three, four, five, six, seven, eight, nine or 10 amino acids on either side, starting anywhere from residue 10 and ending anywhere up to residue 115; and also non-linear epitopes incorporating this sequence or a portion thereof, as well as any of one, two, three, four, five, six, seven, eight, nine or 10 non-contiguous amino acids of the sequence);

ECD region of the polypeptide W38346_P7 (SEQ ID NO:9): W38346_P7__23-75 (SEQ ID NO:10)-sequence: EELENS-GDTTVESERPNKVTIPSTFAAVTIKETL-NANINSTNFAPDENQLE (and optionally bridging amino acids of any of one, two, three, four, five, six, seven, eight, nine or 10 amino acids on either side, starting anywhere from residue 13 and ending anywhere up to residue 85; and also non-linear epitopes incorporating this sequence or a portion thereof, as well as any of one, two, three, four, five, six, seven, eight, nine or 10 non-contiguous amino acids of the sequence);

and fragments and variants and homologs thereof possessing at least 80%, at least 85%, at least 90%, at least 95, at least 96, at least 97, at least 98 or at least 99% sequence identity therewith.

The TMEM154 extracellular domain can contain one or more amino acids from the signal peptide or the putative transmembrane domain of TMEM154. During secretion, the number of amino acids of the signal peptide that are cleaved can vary depending on the expression system and the host. Additionally or alternatively, fragments of TMEM154 extracellular domain missing one or more amino acids from the C-terminus or the N-terminus that retain the ability to bind to the TMEM154 receptor can be used as a fusion partner for the disclosed fusion proteins.

The term "immune response" refers to the action of, for example, lymphocytes, antigen presenting cells, phagocytic cells, granulocytes, and soluble macromolecules produced by the above cells or cells produced by the liver or spleen (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

The term "antibody" as referred to herein includes whole polyclonal and monoclonal antibodies and any antigen binding fragment (i.e., "antigen-binding portion") or single chains thereof. An "antibody" refers to a glycoprotein comprising at least two heavy (H) chains and two light (L) chains interconnected by disulfide bonds, or an antigen binding portion thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., TMEM154 polypeptides and proteins). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the V Light, V Heavy, Constant light (CL) and CH1 domains; (ii) a F(ab').2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds TMEM154 proteins or polypeptides is substantially free of antibodies that specifically bind antigens other than TMEM154 proteins or polypeptides, respectively. An isolated antibody that specifically binds TMEM154 proteins or polypeptides may, however, have cross-reactivity to other antigens, such as, TMEM154 proteins or TMEM154 polypeptides from other species, respectively. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies according to at least some embodiments of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

As used herein, an antibody that "specifically binds" to human TMEM154 proteins or polypeptides is intended to refer to an antibody that binds to human TMEM154 proteins or polypeptides optionally one with a KD of 5×10-8 M or less, 3×10-8 M or less, or 1×10-9 M or less.

The term "K-assoc" or "Ka", as used herein, is intended to refer to the association rate of a particular antibody-antigen interaction, whereas the term "Kdiss" or "Kd," as used herein, is intended to refer to the dissociation rate of a particular antibody-antigen interaction. The term "KD", as used herein, is intended to refer to the dissociation constant, which is obtained from the ratio of Kd to Ka (i.e., Kd/Ka) and is expressed as a molar concentration (M). KD values for antibodies can be determined using methods well established in the art. A preferred method for determining the KD of an antibody is by using surface Plasmon resonance, optionally using a biosensor system such as a Biacore® system.

As used herein, the term "high affinity" for an IgG antibody refers to an antibody having a KD of $10^{-8}$ M or less, $10^{-9}$ M or less or $10^{-10}$ M or less for a target antigen. However, "high affinity" binding can vary for other antibody isotypes. For example, "high affinity" binding for an IgM isotype refers to an antibody having a KD of $10^{-7}$ M or less, or $10^{-8}$ M or less.

As used herein, the term "tail" refers to a peptide sequence at the end of an amino acid sequence that is unique to a splice variant according to the present invention. Therefore, a splice variant having such a tail may optionally be considered as a chimera, in that at least a first portion of the splice variant is typically highly homologous (often 100% identical) to a portion of the corresponding known protein, while at least a second portion of the variant comprises the tail.

As used herein, the term "head" refers to a peptide sequence at the beginning of an amino acid sequence that is unique to a splice variant according to the present invention. Therefore, a splice variant having such a head may optionally be considered as a chimera, in that at least a first portion of the splice variant comprises the head, while at least a second portion is typically highly homologous (often 100% identical) to a portion of the corresponding known protein.

As used herein, the term "an edge portion" refers to a connection between two portions of a splice variant according to the present invention that were not joined in the wild type or known protein. An edge may optionally arise due to a join between the above "known protein" portion of a variant and the tail, for example, and/or may occur if an internal portion of the wild type sequence is no longer present, such that two portions of the sequence are now contiguous in the splice variant that were not contiguous in the known protein. A "bridge" may optionally be an edge portion as described above, but may also include a join between a head and a "known protein" portion of a variant, or a join between a tail and a "known protein" portion of a variant, or a join between an insertion and a "known protein" portion of a variant.

In some embodiments, a bridge between a tail or a head or a unique insertion, and a "known protein" portion of a variant, comprises at least about 10 amino acids, or in some embodiments at least about 20 amino acids, or in some embodiments at least about 30 amino acids, or in some embodiments at least about 40 amino acids, in which at least one amino acid is from the tail/head/insertion and at least one amino acid is from the "known protein" portion of a variant. In some embodiments, the bridge may comprise any number of amino acids from about 10 to about 40 amino acids (for example, 10, 11, 12, 13 . . . 37, 38, 39, 40 amino acids in length, or any number in between).

It should be noted that a bridge cannot be extended beyond the length of the sequence in either direction, and it should be assumed that every bridge description is to be read in such manner that the bridge length does not extend beyond the sequence itself.

Furthermore, bridges are described with regard to a sliding window in certain contexts below. For example, certain descriptions of the bridges feature the following format: a bridge between two edges (in which a portion of the known protein is not present in the variant) may optionally be described as follows: a bridge portion of CONTIG-NAME_P1 (representing the name of the protein), comprising a polypeptide having a length "n", wherein n is at least about 10 amino acids in length, optionally at least about 20 amino acids, at least about 30 amino acids, at least about 40 amino acids, or at least about 50 amino acids in length, wherein at least two amino acids comprise XX (2 amino acids in the center of the bridge, one from each end of the edge), having a structure as follows (numbering according to the sequence of CONTIG-NAME_P1): a sequence starting from any of amino acid numbers 49−x to 49 (for example); and ending at any of amino acid numbers 50+((n−2)−x) (for example), in which x varies from 0 to n−2. In this example, it should also be read as including bridges in which n is any number of amino acids between 10-50 amino acids in length. Furthermore, the bridge polypeptide cannot extend beyond the sequence, so it should be read such that 49−x (for example) is not less than 1, nor 50+((n−2)−x) (for example) greater than the total sequence length.

As used herein the term "treatment" refers to care provided to relieve illness and refers to both a therapeutic treatment or prophylactic/preventative measures, wherein the objective is to prevent or slow down (lessen) the targeted pathologic condition or disorder. Those in need of treatment include those already with the disorder as well as those prone to have the disorder or those in whom the disorder is to be prevented. The term treatment as used herein refers also to "maintenance therapy", which is a treatment that is given to keep a pathologic condition or disorder from coming back after it has disappeared following the initial therapy.

The term "therapeutically effective amount" refers to an amount of agent according to the present invention that is effective to treat a disease or disorder in a mammal.

As used herein the term "diagnosis" refers to the process of identifying a medical condition or disease by its signs, symptoms, and in particular from the results of various diagnostic procedures, including e.g. detecting the expression of the nucleic acids or polypeptides according to at least some embodiments of the invention in a biological sample (e.g. in cells, tissue or serum, as defined below) obtained from an individual. Furthermore, as used herein the term "diagnosis" encompasses screening for a disease, detecting a presence or a severity of a disease, distinguishing a disease from other diseases including those diseases that may feature one or more similar or identical symptoms, providing prognosis of a disease, monitoring disease progression or relapse, as well as assessment of treatment efficacy and/or relapse of a disease, disorder or condition, as well as selecting a therapy and/or a treatment for a disease, optimization of a given therapy for a disease, monitoring the treatment of a disease, and/or predicting the suitability of a therapy for specific patients or subpopulations or determining the appropriate dosing of a therapeutic product in patients or subpopulations. The diagnostic procedure can be performed in vivo or in vitro. It should be noted that a "biological sample obtained from the subject" may also optionally comprise a sample that has not been physically removed from the subject.

As used herein the term "combination therapy" refers to the simultaneous or consecutive administration of two or more medications or types of therapy to treat a single disease. In particular, the term refers to the use of any of the polypeptides, polynucleotides, antibodies or pharmaceutical compositions according to at least some embodiments of the invention in combination with at least one additional medication or therapy. Thus, treatment of a disease using the agents according to at least some embodiments of the present invention may be combined with therapies well known in the art that include, but are not limited to, radiation therapy, antibody therapy, chemotherapy or surgery or in combination therapy with other biological agents, conventional drugs, anti-cancer agents, immunosuppressants, cytotoxic drugs for cancer, chemotherapeutic agents. According to at least some embodiments, treatment of multiple myeloma using the agents according to at least some embodiments of the present invention may be combined with an agent including but not limited to Melphalan, thalidomide (MPT), or combination Bortezomib (Velcade), melphalan, prednisone (VMP) or a combination of Lenalidomide plus low-dose dexamethasone;

and/or biophosphonates; chemotherapy (e.g., alkylating agents, vincristine, doxorubicin); autologous stem cell transplantation; and corticosteroids (e.g., prednisone and dexamethasone).

As used herein, the term "synergistic effect" or "synergism" refers to a greater effect seen with a combination of a plurality of therapeutic agents, including at least one therapeutic agent according to any embodiment of the present invention, in which the therapeutic effect is greater than the additive effects of the plurality of agents when administered singly. By "greater therapeutic effect", it is meant a greater cancer effect and/or a reduction in one or more side effects.

As used herein, the term "subject" includes any human or nonhuman animal. The term "nonhuman animal" includes all vertebrates, e.g., mammals and non-mammals, such as non-human primates, sheep, dogs, cats, horses, cows, chickens, amphibians, reptiles, etc.

Various aspects of the invention are described in further detail in the following subsections.

Nucleic Acids

A "nucleic acid fragment" or an "oligonucleotide" or a "polynucleotide" are used herein interchangeably to refer to a polymer of nucleic acid residues. A polynucleotide sequence according to at least some embodiments of the present invention refers to a single or double stranded nucleic acid sequences which is isolated and provided in the form of an RNA sequence, a complementary polynucleotide sequence (cDNA), a genomic polynucleotide sequence and/or a composite polynucleotide sequences (e.g., a combination of the above).

Thus, the present invention encompasses nucleic acid sequences described hereinabove; fragments thereof, sequences hybridizable therewith, sequences homologous thereto [e.g., at least 90%, at least 95, 96, 97, 98 or 99% or more identical to the nucleic acid sequences set forth herein], sequences encoding similar polypeptides with different codon usage, altered sequences characterized by mutations, such as deletion, insertion or substitution of one or more nucleotides, either naturally occurring or man induced, either randomly or in a targeted fashion. The present invention also encompasses homologous nucleic acid sequences (i.e., which form a part of a polynucleotide sequence according to at least some embodiments of the present invention), which include sequence regions unique to the polynucleotides according to at least some embodiments of the present invention.

In cases where the polynucleotide sequences according to at least some embodiments of the present invention encode previously unidentified polypeptides, the present invention also encompasses novel polypeptides or portions thereof, which are encoded by the isolated polynucleotide and respective nucleic acid fragments thereof described hereinabove.

Thus, the present invention also encompasses polypeptides encoded by the polynucleotide sequences according to at least some embodiments of the present invention. The present invention also encompasses homologues of these polypeptides, such homologues can be at least 90%, at least 95, 96, 97, 98 or 99% or more homologous to the amino acid sequences set forth below, as can be determined using BlastP software of the National Center of Biotechnology Information (NCBI) using default parameters. Finally, the present invention also encompasses fragments of the above described polypeptides and polypeptides having mutations, such as deletions, insertions or substitutions of one or more amino acids, either naturally occurring or man induced, either randomly or in a targeted fashion.

Oligonucleotides designed for carrying out the methods according to at least some embodiments of the present invention for any of the sequences provided herein (designed as described above) can be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art.

Oligonucleotides used according to this aspect according to at least some embodiments of the present invention are those having a length selected from a range of about 10 to about 200 bases, optionally about 15 to about 150 bases, about 20 to about 100 bases, or about 20 to about 50 bases.

The oligonucleotides according to at least some embodiments of the present invention may comprise heterocyclic nucleosides consisting of purines and the pyrimidines bases, bonded in a 3' to 5' phosphodiester linkage.

Polypeptides

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

Polypeptide products can be biochemically synthesized such as by employing standard solid phase techniques. Such methods include exclusive solid phase synthesis, partial solid phase synthesis methods, fragment condensation, classical solution synthesis. These methods are optionally used when the peptide is relatively short (i.e., 10 kDa) and/or when it cannot be produced by recombinant techniques (i.e., not encoded by a nucleic acid sequence) and therefore involves different chemistry.

Solid phase polypeptide synthesis procedures are well known in the art and further described by John Morrow Stewart and Janis Dillaha Young, Solid Phase Peptide Syntheses (2nd Ed., Pierce Chemical Company, 1984).

Synthetic polypeptides can be purified by preparative high performance liquid chromatography [Creighton T. (1983) Proteins, structures and molecular principles. WH Freeman and Co. N.Y.] and the composition of which can be confirmed via amino acid sequencing.

In cases where large amounts of a polypeptide are desired, it can be generated using recombinant techniques such as described by Bitter et al., (1987) Methods in Enzymol. 153: 516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

It will be appreciated that peptides according to at least some embodiments of the present invention may be degradation products, synthetic peptides or recombinant peptides as well as peptidomimetics, typically, synthetic peptides and peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted by synthetic non-natural acid such as Phenylglycine, TIC, naphthylelanine (Nol), ring-methylated derivatives of Phe, halogenated derivatives of Phe or o-methyl-Tyr.

In addition to the above, the peptides according to at least some embodiments of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

The peptides according to at least some embodiments of the present invention might include one or more non-natural or natural polar amino acids, including but not limited to serine and threonine which are capable of increasing peptide solubility due to their hydroxyl-containing side chain.

The peptides according to at least some embodiments of the present invention can be biochemically synthesized such as by using standard solid phase techniques. These methods include exclusive solid phase synthesis, partial solid phase synthesis methods, fragment condensation, classical solution synthesis. These methods are optionally used when the peptide is relatively short (i.e., 10 kDa) and/or when it cannot be produced by recombinant techniques (i.e., not encoded by a nucleic acid sequence) and therefore involves different chemistry.

Solid phase peptide synthesis procedures are well known in the art and further described by John Morrow Stewart and Janis Dillaha Young, Solid Phase Peptide Syntheses (2nd Ed., Pierce Chemical Company, 1984).

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

In cases where large amounts of the peptides according to at least some embodiments of the present invention are desired, the peptides can be generated using recombinant techniques such as described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

Recombinant Expression of Polypeptides

Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, nucleic acid molecules may be introduced into mammalian cells by viral vectors. Methods of transforming cells are well known in the art. See, e.g., U.S. Pat. Nos. 4,399,216, 4,912,040, 4,740,461, and 4,959,455 (which patents are hereby incorporated herein by reference). Methods of transforming plant cells are well known in the art, including, e.g., Agrobacterium-mediated transformation, biolistic transformation, direct injection, electroporation and viral transformation. Methods of transforming bacterial and yeast cells are also well known in the art.

Mammalian cell lines available as hosts for expression are well known in the art and include many immortalized cell lines available from e.g. the American Type Culture Collection (ATCC). These include, inter alia, Chinese hamster ovary (CHO) cells, NS0, SP2 cells, HEK-293T cells, NIH-3T3 cells, HeLa cells, baby hamster kidney (BHK) cells, monkey kidney cells (COS), human hepatocellular carcinoma cells (e.g., Hep G2), A549 cells, 3T3 cells, and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. When recombinant expression vectors encoding the polypeptides according to at least some embodiments of the invention or fragments thereof are introduced into mammalian host cells, the polypeptides are produced by culturing the host cells for a period of time sufficient to allow for expression of the polypeptide in the host cells or, more preferably, secretion of the polypeptide into the culture medium in which the host cells are grown. Polypeptides can be recovered from the culture medium using standard protein purification methods. Plant host cells include, e.g., *Nicotiana, Arabidopsis*, duckweed, corn, wheat, potato, etc. Bacterial host cells include *E. coli* and *Streptomyces* species. Yeast host cells include *Schizosaccharomyces pombe, Saccharomyces cerevisiae* and *Pichia pastoris*.

Further, expression of the polypeptides according to at least some embodiments of the invention (or other moieties derived therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, 0 338 841 and 0 323 997.

It is likely that polypeptides expressed by different cell lines or in transgenic animals will have different glycosylation patterns. However, all polypeptides encoded by the nucleic acid molecules provided herein, or comprising the amino acid sequences provided herein are part of the instant invention, regardless of their glycosylation pattern.

Vectors

According to at least some embodiments, the invention provides vectors comprising the nucleic acid molecules that encode the polypeptides, fusion proteins, modified polypeptides, and polypeptide fragments of at least some embodiments the invention.

To express the polypeptides according to at least some embodiments of the invention, or fragments thereof, DNAs encoding partial or full-length polypeptides, obtained as described above, are inserted into expression vectors such that the genes are operatively linked to transcriptional and translational control sequences. Expression vectors include plasmids, retroviruses, adenoviruses, adeno-associated viruses (AAV), plant viruses such as cauliflower mosaic virus, tobacco mosaic virus, cosmids, YACs, EBV derived episomes, and the like. The gene is ligated into a vector such that transcriptional and translational control sequences within the vector serve their intended function of regulating the transcription and translation of the gene. The expression vector and expression control sequences are chosen to be compatible with the expression host cell used. The gene is inserted into the expression vector by standard methods (e.g., ligation of complementary restriction sites on the gene fragment and vector, or blunt end ligation if no restriction sites are present).

A convenient vector is one that encodes a functionally complete sequence, with appropriate restriction sites engineered so that any sequence can be easily inserted and expressed, as described above. Polyadenylation and transcription termination occur at native chromosomal sites downstream of the coding regions. The recombinant expression vector can also encode a signal peptide that facilitates secretion of the polypeptide from a host cell. The gene may be cloned into the vector such that the signal peptide is linked in-frame to the amino terminus of the gene.

In addition to the nucleic acid according to at least some embodiments of the invention, the recombinant expression vectors carry regulatory sequences that control the expression of the gene in a host cell. It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. Nos. 5,168,062, 4,510,245, and 4,968,615, each of which is hereby incorporated by reference. Methods of expressing polypeptides in bacterial cells or fungal cells, e.g., yeast cells, are also well known in the art.

In addition to the nucleic acids according to at least some embodiments of the invention and regulatory sequences, the recombinant expression vectors according to at least some embodiments of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene, the neo gene (for G418 selection), and the glutamate synthetase gene.

Variants of TMEM154 Polypeptides

Useful variants of such TMEM154 polypeptides include those that increase biological activity, as indicated by any of the assays described herein, or that increase half life or stability of the protein. Soluble TMEM154 polypeptides and TMEM154 fragments, or fusions thereof having TMEM154 activity, can be engineered to increase biological activity. In a further embodiment, the TMEM154 polypeptide or fusion protein has been modified with at least one amino acid substitution, deletion, or insertion that increases the binding of the molecule to its partner molecule. Preferential binding refers to binding that is at least 10%, 20%, 30%, 40%, 50%, 60% f 70%, 80%, 90%, 95%, or greater for one type of cell over another type of cell. Still other variants of TMEM154 can be engineered to have reduced binding to its partner molecule relative to wildtype TMEM154. Also optionally, variant TMEM154 polypeptides can be engineered to have an increased half-life relative to wildtype. These variants typically are modified to resist enzymatic degradation. Exemplary modifications include modified amino acid residues and modified peptide bonds that resist enzymatic degradation. Various modifications to achieve this are known in the art.

Fusion Proteins

According to at least some embodiments, TMEM154 fusion polypeptides have a first fusion partner comprising all or a part of a TMEM154 protein fused to a second polypeptide directly or via a linker peptide sequence or a chemical linker useful to connect the two proteins. The TMEM154 polypeptide may optionally be fused to a second polypeptide to form a fusion protein as described herein. The presence of the second polypeptide can alter the solubility, stability, affinity and/or valency of the TMEM154 fusion polypeptide. As used herein, "valency" refers to the number of binding sites available per molecule. In one embodiment the second polypeptide is a polypeptide from a different source or different protein.

According to at least some embodiments, the TMEM154 protein or fragment is selected for its activity for the treatment of immune related disorder and/or according to one or more in vitro biological activities as described herein.

In one embodiment, the second polypeptide contains one or more domains of an immunoglobulin heavy chain constant region, preferably having an amino acid sequence corresponding to the hinge, CH2 and CH3 regions of a human immunoglobulin Cγ1 chain or to the hinge, CH2 and CH3 regions of a murine immunoglobulin Cγ2a chain. SEQ ID NO: 64 provides exemplary sequence for the hinge, CH2 and CH3 regions of a human immunoglobulin Cγ1.

According to at least some embodiments, the fusion protein is a dimeric fusion protein. In an optional dimeric fusion protein, the dimer results from the covalent bonding of Cys residue in the hinge region of two of the Ig heavy chains that are the same Cys residues that are disulfide linked in dimerized normal Ig heavy chains. Such proteins are referred to as TMEM154-Ig.

In one embodiment, the immunoglobulin constant domain may contain one or more amino acid insertions, deletions or substitutions that enhance binding to specific cell types, increase the bioavailablity, or increase the stability of the TMEM154 polypeptides, fusion proteins, or fragments thereof. Suitable amino acid substitutions include conservative and non-conservative substitutions, as described above.

The fusion proteins optionally contain a domain that functions to dimerize or multimerize two or more fusion proteins. The peptide/polypeptide linker domain can either be a separate domain, or alternatively can be contained within one of the other domains (TMEM154 polypeptide or second polypeptide) of the fusion protein. Similarly, the domain that functions to dimerize or multimerize the fusion proteins can either be a separate domain, or alternatively can be contained within one of the other domains (TMEM154 polypeptide, second polypeptide or peptide/polypeptide linker domain) of the fusion protein. In one embodiment, the dimerization/multimerization domain and the peptide/polypeptide linker domain are the same. Further specific, illustrative and non-limiting examples of dimerization/multimerization domains and linkers are given below.

Fusion proteins disclosed herein according to at least some embodiments of the present invention are of formula I: N-R1-R2-R3-C wherein "N" represents the N-terminus of the fusion protein, "C" represents the C-terminus of the fusion protein. In the further embodiment, "R1" is a TMEM154 polypeptide, "R2" is an optional peptide/polypeptide or chemical linker domain, and "R3" is a second polypeptide. Alternatively, R3 may be a TMEM154 polypeptide and R1 may be a second polypeptide.

Optionally, the fusion protein comprises the TMEM154 polypeptide fragments comprising SEQ ID NO:10, fused, optionally by a linker peptide of one or more amino acids (e.g. GS) to one or more "half-life extending moieties". A "half-life extending moiety" is any moiety, for example, a polypeptide, small molecule or polymer, that, when appended to protein, extends the in vivo half-life of that protein in the body of a subject (e.g., in the plasma of the subject). For example, a half-life extending moiety is, in an embodiment of the invention, polyethylene glycol (PEG), monomethoxy PEG (mPEG) or an immunoglobulin (Ig). In an embodiment of the invention, PEG is a 5, 10, 12, 20, 30, 40 or 50 kDa moiety or larger or comprises about 12000 ethylene glycol units (PEG12000).

Dimerization or multinierization can occur between or among two or more fusion proteins through dimerization or multimerization domains. Alternatively, dimerization or multimerization of fusion proteins can occur by chemical crosslinking. The dimers or multimers that are formed can be homodimeric/homomultimeric or heterodimeric/heteromultimeric. The second polypeptide "partner" in the TMEM154 fusion polypeptides may be comprised of one or more other proteins, protein fragments or peptides as described herein, including but not limited to any immunoglobulin (Ig) protein or portion thereof, preferably the Fc region, or a portion of a biologically or chemically active protein such as the papillomavirus E7 gene product, melanoma-associated antigen p97), and HIV env protein (gp120). The "partner" is optionally selected to provide a soluble dimer/multimer and/or for one or more other biological activities as described herein.

Dimerization or multimerization can occur between or among two or more fusion proteins through dimerization or multimerization domains, including those described above. Alternatively, dimerization or multimerization of fusion proteins can occur by chemical crosslinking. Fusion protein dimers can be homodimers or heterodimers. Fusion protein multimers can be homomultimers or heteromultimers. Fusion protein dimers as disclosed herein are of formula II:

N-R1-R2-R3-C

N-R4-R5-R6-C or, alternatively, are of formula III:

N-R1-R2-R3-C

C-R4-R5-R6-N wherein the fusion proteins of the dimer provided by formula II are defined as being in a parallel orientation and the fusion proteins of the dimer provided by formula III are defined as being in an antiparallel orientation. Parallel and antiparallel dimers are also referred to as cis and trans dimers, respectively. "N" and "C" represent the N- and C-termini of the fusion protein, respectively. The fusion protein constituents "R1", "R2" and "R3" are as defined above with respect to formula I. With respect to both formula II and formula III, "R4" is a TMEM154 polypeptide or a second polypeptide, "R5" is an optional peptide/polypeptide linker domain, and "R6" is a TMEM154 polypeptide or a second polypeptide, wherein "R6" is a TMEM154 polypeptide when "R4" is a second polypeptide, and "R6"' is a second polypeptide when "R4" is a TMEM154 polypeptide. In one embodiment, "R1" is a TMEM154 polypeptide, "R4" is also a TMEM154 polypeptide, and "R3" and "R6" are both second polypeptides.

Fusion protein dimers of formula II are defined as homodimers when "R1"="R4", "R2"="R5" and "R3"="R6". Similarly, fusion protein dimers of formula III are defined as homodimers when "R1"="R6", "R2"="R5" and "R3"="R4". Fusion protein dimers are defined as heterodimers when these conditions are not met for any reason. For example, heterodimers may contain domain orientations that meet these conditions (i.e., for a dimer according to formula II, "R1" and "R4" are both TMEM154 polypeptides, "R2" and "R5" are both peptide/polypeptide linker domains and "R3" and "R6" are both second polypeptides), however the species of one or more of these domains is not identical. For example, although "R3" and "R6" may both be TMEM154 polypeptides, one polypeptide may contain a wild-type TMEM154 amino acid sequence while the other polypeptide may be a variant TMEM154 polypeptide. An exemplary variant TMEM154 polypeptide is TMEM154 polypeptide that has been modified to have increased or decreased binding to a target cell, increased activity on immune cells, increased or decreased half life or stability. Dimers of fusion proteins that contain either a CHI or CL region of an immunoglobulin as part of the polypeptide linker domain preferably form heterodimers wherein one fusion protein of the dimer contains a CHI region and the other fusion protein of the dimer contains a CL region.

Fusion proteins can also be used to form multimers. As with dimers, multimers may be parallel multimers, in which all fusion proteins of the multimer are aligned in the same orientation with respect to their N- and C-termini. Multimers may be antiparallel multimers, in which the fusion proteins of the multimer are alternatively aligned in opposite orientations with respect to their N- and C-termini. Multimers (parallel or antiparallel) can be either homomultimers or heteromultimers.

The fusion protein is optionally produced in dimeric form; more preferably, the fusion is performed at the genetic level as described below, by joining polynucleotide sequences corresponding to the two (or more) proteins, portions of proteins and/or peptides, such that a joined or fused protein is produced by a cell according to the joined polynucleotide sequence. A description of preparation for such fusion proteins is described with regard to U.S. Pat. No. 5,851,795 to Linsley et al, which is hereby incorporated by reference as if fully set forth herein as a non-limiting example only.

The fusion protein may also optionally be prepared by chemical synthetic methods and the "join" effected chemically, either during synthesis or post-synthesis. Cross-linking and other such methods may optionally be used (optionally also with the above described genetic level fusion methods), as described for example in U.S. Pat. No. 5,547,853 to Wallner et al, which is hereby incorporated by reference as if fully set forth herein as a non-limiting example only.

According to the present invention, a fusion protein may be prepared from a protein of the invention by fusion with a portion of an immunoglobulin comprising a constant region of an immunoglobulin. More preferably, the portion of the immunoglobulin comprises a heavy chain constant region which is optionally and more preferably a human heavy chain constant region. The heavy chain constant region is most preferably an IgG heavy chain constant region, and optionally and most preferably is an Fc chain, most preferably an IgG Fc fragment that comprises the hinge, CH2 and CH3 domains. The Fc chain may optionally be a known or "wild type" Fc chain, or alternatively may be mutated. The Fc portion of the fusion protein may optionally be varied by isotype or subclass, may be a chimeric or hybrid, and/or may be modified, for example to improve effector functions, control of half-life, tissue accessibility, augment biophysical characteristics such as stability, and improve efficiency of production (and less costly). Many modifications useful in construction of disclosed fusion proteins and methods for making them are known in the art, see for example Mueller, et al, MoI. Immun., 34(6):441-452 (1997), Swann, et al., Cur. Opin. Immun., 20:493-499 (2008), and Presta, Cur. Opin. Immun 20:460-470 (2008). In some embodiments the Fc region is the native IgG1, IgG2, or IgG4 Fc region. In some embodiments the Fc region is a hybrid, for example a chimeric consisting of IgG2/IgG4 Fc constant regions. Modifications to the Fc region include, but are not limited to, IgG4 modified to prevent binding to Fc gamma receptors and complement, IgG1 modified to improve binding to one or more Fc gamma receptors, IgG1 modified to minimize effector function (amino acid changes), IgG1 with altered/no glycan (typically by changing expression host), and IgG1 with altered pH-dependent binding to FcRn. The Fc region may include the entire hinge region, or less than the entire hinge region. In another embodiment, the Fc domain may contain one or more amino acid insertions, deletions or substitutions that reduce binding to the low affinity inhibitory Fc receptor CD32B (FcγRIIB) and retain wild-type levels of binding to or enhance binding to the low affinity activating Fc receptor CD16A (FcγRIIIA) Another embodiment includes IgG2-4 hybrids and IgG4 mutants that have reduced binding to FcR (Fc receptor) which increase their half life. Representative IgG2-4 hybrids and IgG4 mutants are described in Angal, S. et al., Molecular Immunology, 30(1):105-108 (1993); Mueller, J. et al., Molecular Immunology, 34(6): 441-452 (1997); and U.S. Pat. No. 6,982,323 to Wang et al. In some embodiments the IgG1 and/or IgG2 domain is deleted; for example, Angal et al. describe IgG1 and IgG2 having serine 241 replaced with a proline. In a further embodiment, the Fc domain contains amino acid insertions, deletions or substitutions that enhance binding to CD16A. A large number of substitutions in the Fc domain of human IgG1 that increase binding to CD16A and reduce binding to CD32B are known in the art and are described in Stavenhagen, et al., Cancer Res., 57(18):8882-90 (2007). Exemplary variants of human IgG1 Fc domains with reduced binding to CD32B and/or increased binding to CD16A contain F243L, R929P, Y300L, V305I or P296L substitutions. These amino acid substitutions may be present in a human IgG1 Fc domain in any combination.

In one embodiment, the human IgG1 Fc domain variant contains a F243L, R929P and Y300L substitution. In another embodiment, the human IgG1 Fc domain variant contains a F243L, R929P, Y300L, V305I and P296L substitution. In another embodiment, the human IgG1 Fc domain variant contains an N297A/Q substitution, as these mutations abolish FcγR binding. Non-limiting, illustrative, exemplary types of mutations are described in US Patent Application No. 20060034852, published on Feb. 16, 2006, hereby incorporated by reference as if fully set forth herein. The term "Fc chain" also optionally comprises any type of Fc fragment.

Several of the specific amino acid residues that are important for antibody constant region-mediated activity in the IgG subclass have been identified. Inclusion, substitution or exclusion of these specific amino acids therefore allows for inclusion or exclusion of specific immunoglobulin constant region-mediated activity. Furthermore, specific changes may result in aglycosylation for example and/or other desired changes to the Fc chain. At least some changes may optionally be made to block a function of Fc which is considered to be undesirable, such as an undesirable immune system effect, as described in greater detail below.

Non-limiting, illustrative examples of mutations to Fc which may be made to modulate the activity of the fusion protein include the following changes (given with regard to the Fc sequence nomenclature as given by Kabat, from Kabat E A et al: Sequences of Proteins of Immunological Interest. US Department of Health and Human Services, NIH, 1991): 220C->S; 233-238 ELLGGP->EAEGAP; 265D->A, preferably in combination with 434N->A; 297N->A (for example to block N-glycosylation); 318-322 EYKCK->AYACA; 330-331AP->SS; or a combination thereof (see for example M. Clark, "Chemical Immunol and Antibody Engineering", pp 1-31 for a description of these mutations and their effect). The construct for the Fc chain which features the above changes optionally and preferably comprises a combination of the hinge region with the CH2 and CH3 domains.

The above mutations may optionally be implemented to enhance desired properties or alternatively to block non-desired properties. For example, aglycosylation of antibodies was shown to maintain the desired binding functionality while blocking depletion of T-cells or triggering cytokine release, which may optionally be undesired functions (see M. Clark, "Chemical Immunol and Antibody Engineering", pp 1-31). Substitution of 331proline for serine may block the ability to activate complement, which may optionally be considered an undesired function (see M. Clark, "Chemical Immunol and Antibody Engineering", pp 1-31). Changing 330alanine to serine in combination with this change may also enhance the desired effect of blocking the ability to activate complement.

Residues 235 and 237 were shown to be involved in antibody-dependent cell-mediated cytotoxicity (ADCC), such that changing the block of residues from 233-238 as described may also block such activity if ADCC is considered to be an undesirable function.

Residue 220 is normally a cysteine for Fc from IgG1, which is the site at which the heavy chain forms a covalent linkage with the light chain. Optionally, this residue may be changed to a serine, to avoid any type of covalent linkage (see M. Clark, "Chemical Immunol and Antibody Engineering", pp 1-31).

The above changes to residues 265 and 434 may optionally be implemented to reduce or block binding to the Fc receptor, which may optionally block undesired functionality of Fc related to its immune system functions (see "Binding site on Human IgG1 for Fc Receptors", Shields et al, Vol 276, pp 6591-6604, 2001).

The above changes are intended as illustrations only of optional changes and are not meant to be limiting in any way. Furthermore, the above explanation is provided for descriptive purposes only, without wishing to be bound by a single hypothesis.

The aforementioned exemplary fusion proteins can incorporate any combination of the variants described herein. In another embodiment the terminal lysine of the aforementioned exemplary fusion proteins is deleted. The disclosed fusion proteins can be isolated using standard molecular biology techniques. For example, an expression vector containing a DNA sequence encoding a TMEM154-Ig fusion protein is transfected into 293 cells by calcium phosphate precipitation and cultured in serum-free DMEM. The supernatant is collected at 72 h and the fusion protein is purified by Protein G, or preferably Protein A SEPHAROSE® columns (Pharmacia, Uppsala, Sweden). Optionally, a DNA sequence encoding a TMEM154-Ig fusion protein is transfected into GPEx® retrovectors and expressed in CHO-S cells following four rounds of retrovector transduction. The protein is clarified from supernatants using protein A chromatography.

In another embodiment the second polypeptide TMEM154 have a conjugation domain through which additional molecules can be bound to the TMEM154 fusion proteins. In one such embodiment, the conjugated molecule is capable of targeting the fusion protein to a particular organ or tissue; further specific, illustrative, non-limiting examples of such targeting domains and/or molecules are given below.

In another such embodiment the conjugated molecule is another immunomodulatory agent that can enhance or augment the effects of the TMEM154 fusion protein. In another embodiment the conjugated molecule is Polyethylene Glycol (PEG).

Peptide or Polypeptide Linker Domain

The disclosed TMEM154 fusion proteins optionally contain a peptide or polypeptide linker domain that separates the TMEM154 polypeptide from the second polypeptide. In one embodiment, the linker domain contains the hinge region of an immunoglobulin. In a further embodiment, the hinge region is derived from a human immunoglobulin. Suitable human immunoglobulins that the hinge can be derived from include IgG, IgD and IgA. In a further embodiment, the hinge region is derived from human IgG Amino acid sequences of immunoglobulin hinge regions and other domains are well known in the art. In one embodiment, TMEM154 fusion polypeptides contain the hinge, CH2 and CH3 regions of a human immunoglobulin Cγ1 chain having at least 85%, 90%, 95%, 99% or 100% sequence homology to amino acid sequence set forth in SEQ ID NO:64:

The hinge can be further shortened to remove amino acids 1, 2, 3, 4, 5, or combinations thereof of SEQ ID NO: 64. In one embodiment, amino acids 1 and 2 of SEQ ID NO: 64 are deleted.

In another embodiment, the TMEM154 fusion polypeptides contain the hinge, CH2 and CH3 regions of a murine immunoglobulin Cγ2a chain at least 85%, 90%, 95%, 99% or 100% sequence homology to amino acid sequence set forth in SEQ ID NO: 66: EPRGPTIKPCPPCKCPAPNLLGGPS-VFIFPPKIKDVLMISLSPIVTCVVVDVSEDDPDVQISW FVNNVEVHTAQTQTHREDYNSTLRVVSALPIQHQDW MSGKEFKCKVNNKDLPAPIERTISKPKGSVRAPQVY VLPPPEEEMTKKQVTLTCMVTDFMPEDIYVEWTNN GKTELNYKNTEPVLDSDGSYFMYSKLRVEKKNWVE RNSYSCSVVHEGLHNHHTTKSFSRTPGK. In another embodiment, the linker domain contains a hinge region of an immunoglobulin as described above, and further includes one or more additional immunoglobulin domains. Other suitable peptide/polypeptide linker domains include naturally occurring or non-naturally occurring peptides or polypeptides. Peptide linker sequences are at least 2 amino acids in length. Optionally the peptide or polypeptide domains are flexible peptides or polypeptides. A "flexible linker" herein refers to a peptide or polypeptide containing two or more amino acid residues joined by peptide bond(s) that provides increased rotational freedom for two polypeptides linked thereby than the two linked polypeptides would have in the absence of the flexible linker. Such rotational freedom allows two or more antigen binding sites joined by the flexible linker to each access target antigen(s) more efficiently.

Exemplary flexible peptides/polypeptides include, but are not limited to, the amino acid sequences Gly-Ser (SEQ ID NO:67), Gly-Ser-Gly-Ser (SEQ ID NO:68), Ala-Ser (SEQ ID NO:69), Gly-Gly-Gly-Ser (SEQ ID NO:70), (Gly4-Ser)3 (SEQ ID NO:71) and (Gly4-Ser)4 (SEQ ID NO: 72). Additional flexible peptide/polypeptide sequences are well known in the art.

Dimerization, Multimerization and Targeting Domains

The fusion proteins disclosed herein optionally contain a dimerization or multimerization domain that functions to dimerize or multimerize two or more fusion proteins. The domain that functions to dimerize or multimerize the fusion proteins can either be a separate domain, or alternatively can be contained within one of the other domains (TMEM154 polypeptide, second polypeptide, or peptide/polypeptide linker domain) of the fusion protein.

```
EPKSCDKTHTCPPCPAPELLGGPSVFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKAKGQPREPQVYTLPPSRDELTKNQV

SLTCLVKGFYPSDIAVEWESNGQPENNYKTTPPVLDSDGSFFLYSKLTVDKSRWQQGNVFSCSVMHEALHNHYT

QKSLSLSPGK
```

In another embodiment, TMEM154 fusion polypeptides contain the, CH2 and CH3 regions of a human immunoglobulin Cγ1 chain having at least 85%, 90%, 95%, 99% or 100% sequence homology to amino acid sequence set forth in SEQ ID NO:65:

A "dimerization domain" is formed by the association of at least two amino acid residues or of at least two peptides or polypeptides (which may have the same, or different, amino acid sequences). The peptides or polypeptides may interact with each other through covalent and/or non-covalent asso-

```
DKTHTCPPCPAPELLGGPSVFLFPPKPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQGNVFSCSVMHEALHNHYTQKSLS

LSPGK.
``` ciations). Optional dimerization domains contain at least one cysteine that is capable of forming an intermolecular disulfide bond with a cysteine on the partner fusion protein. The dimerization domain can contain one or more cysteine residues such that disulfide bond(s) can form between the partner fusion proteins. In one embodiment, dimerization domains contain one, two or three to about ten cysteine residues. In a further embodiment, the dimerization domain is the hinge region of an immunoglobulin.

Additional exemplary dimerization domains can be any known in the art and include, but not limited to, coiled coils, acid patches, zinc fingers, calcium hands, a $C_H1$-$C_L$ pair, an "interface" with an engineered "knob" and/or "protruberance" as described in U.S. Pat. No. 5,821,333, leucine zippers (e.g., from jun and/or fos) (U.S. Pat. No. 5,932,448), SH2 (src homology 2), SH3 (src Homology 3) (Vidal, et al, Biochemistry, 43, 7336-44 ((2004)), phosphotyrosine binding (PTB) (Zhou, et al., Nature, 378:584-592 (1995)), WW (Sudol, Prog, Biochys. Mol. Bio., 65:113-132 (1996)), PDZ (Kim, et al., Nature, 378: 85-88 (1995); Komau, et al, Science, 269.1737-1740 (1995)) 14-3-3, WD40 (Hu5 et al., J Biol Chem., 273, 33489-33494 (1998)) EH, Lim, an isoleucine zipper, a receptor dimer pair (e.g., interleukin-8 receptor (IL-8R); and integrin heterodimers such as LFA-I and GPIIIb/IIIa), or the dimerization region(s) thereof, dimeric ligand polypeptides (e.g. nerve growth factor (NGF), neurotrophin-3 (NT-3), interleukin-8 (IL-8), vascular endothelial growth factor (VEGF), VEGF-C, VEGF-D, PDGF members, and brain-derived neurotrophic factor (BDNF) (Arakawa, et al., J Biol. Chem., 269(45): 27833-27839 (1994) and Radziejewski, et al., Biochem., 32(48): 1350 (1993)) and can also be variants of these domains in which the affinity is altered. The polypeptide pairs can be identified by methods known in the art, including yeast two hybrid screens. Yeast two hybrid screens are described in U.S. Pat. Nos. 5,283,173 and 6,562,576. Affinities between a pair of interacting domains can be determined using methods known in the art, including as described in Katahira, et al, J. Biol Chem, 277, 9242-9246 (2002)). Alternatively, a library of peptide sequences can be screened for heterodimerization, for example, using the methods described in WO 01/00814. Useful methods for protein-protein interactions are also described in U.S. Pat. No. 6,790,624.

A "multimerization domain" is a domain that causes three or more peptides or polypeptides to interact with each other through covalent and/or non-covalent association(s). Suitable multimerization domains include, but are not limited to, coiled-coil domains. A coiled-coil is a peptide sequence with a contiguous pattern of mainly hydrophobic residues spaced 3 and 4 residues apart, usually in a sequence of seven amino acids (heptad repeat) or eleven amino acids (undecad repeat), which assembles (folds) to form a multimeric bundle of helices. Coiled-coils with sequences including some irregular distribution of the 3 and 4 residues spacing are also contemplated. Hydrophobic residues are in particular the hydrophobic amino acids Val, He, Leu, Met, Tyr, Phe and Trp. "Mainly hydrophobic" means that at least 50% of the residues must be selected from the mentioned hydrophobic amino acids.

The coiled coil domain may be derived from laminin. In the extracellular space, the heterotrimeric coiled coil protein laminin plays an important role in the formation of basement membranes. Apparently, the multifunctional oligomeric structure is required for laminin function. Coiled coil domains may also be derived from the thrombospondins in which three (TSP-I and TSP-2) or five (TSP-3, TSP-4 and TSP-5) chains are connected, or from COMP (COMPcc) (Guo, et al., EMBO J, 1998, 17: 5265-5272) which folds into a parallel five-stranded coiled coil (Malashkevich, et al., Science, 274: 761-765 (1996)). Additional coiled-coil domains derived from other proteins, and other domains that mediate polypeptide multimerization are known in the art and are suitable for use in the disclosed fusion proteins.

In another embodiment, TMEM154 polypeptides, fusion proteins, or fragments thereof can be induced to form multimers by binding to a second multivalent polypeptide, such as an antibody. Antibodies suitable for use to multimerize TMEM154 polypeptides, fusion proteins, or fragments thereof include, but are not limited to, IgM antibodies and cross-linked, multivalent IgG, IgA, IgD, or IgE complexes.

Targeting Domains

The TMEM154 polypeptides and fusion proteins can contain a targeting domain to target the molecule to specific sites in the body. Optional targeting domains target the molecule to areas of inflammation. Exemplary targeting domains are antibodies, or antigen binding fragments thereof that are specific for inflamed tissue or to a proinflammatory cytokine including but not limited to IL17, IL-4, IL-6, IL-12, IL-21, IL-22, and IL-23. In the case of neurological disorders such as Multiple Sclerosis, the targeting domain may target the molecule to the CNS or may bind to VCAM-1 on the vascular epithelium. Additional targeting domains can be peptide aptamers specific for a proinflammatory molecule. In other embodiments, the TMEM154 fusion protein can include a binding partner specific for a polypeptide displayed on the surface of an immune cell, for example a T cell. In still other embodiments, the targeting domain specifically targets activated immune cells. Optional immune cells that are targeted include Th0, Th1, Th 17, Th2 and Th22 T cells, other cells that secrete, or cause other cells to secrete inflammatory molecules including, but not limited to, IL-1beta, TNF-alpha, TGF-beta, IFN-gamma, IL-17, IL-6, IL-23, IL-22, IL-21, and MMPs, and Tregs. For example, a targeting domain for Tregs may bind specifically to CD25.

The terms "individual", "host", "subject", and "patient" are used interchangeably herein, and refer any human or nonhuman animal. The term "nonhuman animal" includes all vertebrates, e.g., mammals and non-mammals, such as nonhuman primates, sheep, dogs, cats, horses, cows chickens, amphibians, reptiles, etc.

Various aspects of the invention are described in further detail in the following subsections.

Chemical Modifications

In the present invention any part of a protein according to at least some embodiments of the invention may optionally be chemically modified, i.e. changed by addition of functional groups. For example the side amino acid residues appearing in the native sequence may optionally be modified, although as described below alternatively other parts of the protein may optionally be modified, in addition to or in place of the side amino acid residues. The modification may optionally be performed during synthesis of the molecule if a chemical synthetic process is followed, for example by adding a chemically modified amino acid. However, chemical modification of an amino acid when it is already present in the molecule ("in situ" modification) is also possible.

The amino acid of any of the sequence regions of the molecule can optionally be modified according to any one of the following exemplary types of modification (in the peptide conceptually viewed as "chemically modified"). Non-limiting exemplary types of modification include carboxymethylation, acylation, phosphorylation, glycosylation or fatty acylation. Ether bonds can optionally be used to join the serine or threonine hydroxyl to the hydroxyl of a sugar. Amide bonds can optionally be used to join the glutamate or aspartate carboxyl groups to an amino group on a sugar (Garg and Jeanloz, Advances in Carbohydrate Chemistry and Biochemistry, Vol. 43, Academic Press (1985); Kunz, Ang. Chem. Int. Ed. English 26:294-308 (1987)). Acetal and ketal bonds can also optionally be formed between amino acids and carbohydrates. Fatty acid acyl derivatives can optionally be made, for example, by acylation of a free amino group (e.g., lysine) (Toth et al., Peptides: Chemistry, Structure and Biology, Rivier and Marshal, eds., ESCOM Publ., Leiden, 1078-1079 (1990)).

As used herein the term "chemical modification", when referring to a protein or peptide according to the present invention, refers to a protein or peptide where at least one of its amino acid residues is modified either by natural processes, such as processing or other post-translational modifications, or by chemical modification techniques which are well known in the art. Examples of the numerous known modifications typically include, but are not limited to: acetylation, acylation, amidation, ADP-ribosylation, glycosylation, GPI anchor formation, covalent attachment of a lipid or lipid derivative, methylation, myristylation, pegylation, prenylation, phosphorylation, ubiquitination, or any similar process.

Other types of modifications optionally include the addition of a cycloalkane moiety to a biological molecule, such as a protein, as described in PCT Application No. WO 2006/050262, hereby incorporated by reference as if fully set forth herein. These moieties are designed for use with biomolecules and may optionally be used to impart various properties to proteins.

Furthermore, optionally any point on a protein may be modified. For example, pegylation of a glycosylation moiety on a protein may optionally be performed, as described in PCT Application No. WO 2006/050247, hereby incorporated by reference as if fully set forth herein. One or more polyethylene glycol (PEG) groups may optionally be added to O-linked and/or N-linked glycosylation. The PEG group may optionally be branched or linear. Optionally any type of water-soluble polymer may be attached to a glycosylation site on a protein through a glycosyl linker.

Altered Glycosylation

Proteins according to at least some embodiments of the invention may be modified to have an altered glycosylation pattern (i.e., altered from the original or native glycosylation pattern). As used herein, "altered" means having one or more carbohydrate moieties deleted, and/or having at least one glycosylation site added to the original protein.

Glycosylation of proteins is typically either N-linked or O-linked. N-linked refers to the attachment of the carbohydrate moiety to the side chain of an asparagine residue. The tripeptide sequences, asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to proteins according to at least some embodiments of the invention is conveniently accomplished by altering the amino acid sequence of the protein such that it contains one or more of the above-described tripeptide sequences (for N-linked glycosylation sites). The alteration may also be made by the addition of, or substitution by, one or more serine or threonine residues in the sequence of the original protein (for O-linked glycosylation sites). The protein's amino acid sequence may also be altered by introducing changes at the DNA level.

Another means of increasing the number of carbohydrate moieties on proteins is by chemical or enzymatic coupling of glycosides to the amino acid residues of the protein. Depending on the coupling mode used, the sugars may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330, and in Aplin and Wriston, CRC Crit. Rev. Biochem., 22: 259-306 (1981).

Removal of any carbohydrate moieties present on proteins according to at least some embodiments of the invention may be accomplished chemically or enzymatically. Chemical deglycosylation requires exposure of the protein to trifluoromethanesulfonic acid, or an equivalent compound. This treatment results in the cleavage of most or all sugars except the linking sugar (N-acetylglucosamine or N-acetylgalactosamine), leaving the amino acid sequence intact.

Chemical deglycosylation is described by Hakimuddin et al., Arch. Biochem. Biophys., 259: 52 (1987); and Edge et al., Anal. Biochem., 118: 131 (1981). Enzymatic cleavage of carbohydrate moieties on proteins can be achieved by the use of a variety of endo- and exo-glycosidases as described by Thotakura et al., Meth. Enzymol., 138: 350 (1987).

Methods of Treatment Using TMEM154 Polypeptides and Proteins

As mentioned hereinabove the TMEM154 proteins and polypeptides according to at least some embodiments of the present invention or nucleic acid sequence or fragments thereof especially the ectodomain or secreted forms of TMEM154 proteins and polypeptides, can be used to treat multiple myeloma, aggressive and/or drug resistant and/or refractory multiple myeloma conditions or disorders.

Thus, according to at least some embodiments of the present invention there is provided a method of treating multiple myeloma, aggressive and/or drug resistant and/or refractory multiple myeloma conditions or disorders, alone or in combination and preferably synergism with one or more additional treatments for multiple myeloma. Such one or more additional treatments could easily be selected by one of ordinary skill in the art.

As used herein the term "treating" refers to preventing, curing, reversing, attenuating, alleviating, minimizing, suppressing or halting the deleterious effects of the above-described diseases, disorders or conditions. The term treatment as used herein refers also to "maintenance therapy", which is a treatment that is given to keep a pathologic condition or disorder from coming back after it has disappeared following the initial therapy.

Treating, according to the present invention, can be effected by specifically upregulating the expression of at least one of the polypeptides according to at least some embodiments of the present invention in the subject.

Optionally, upregulation may be effected by administering to the subject at least one of the polypeptides according to at least some embodiments of the present invention (e.g., recombinant or synthetic) or an active portion thereof, as described herein. However, since the bioavailability of large polypeptides may potentially be relatively small due to high degradation rate and low penetration rate, administration of polypeptides is preferably confined to small peptide fragments (e.g., about 100 amino acids). The polypeptide or peptide may optionally be administered in as part of a pharmaceutical composition, described in more detail below.

It will be appreciated that treatment of the above-described diseases according to the present invention may be combined with other treatment methods known in the art (i.e., combination therapy).

Anti-TMEM154 Antibodies

The antibodies according to at least some embodiments of the invention including those having the particular germline sequences, homologous antibodies, antibodies with conservative modifications, engineered and modified antibodies are characterized by particular functional features or properties of the antibodies. For example, the antibodies bind specifically to human or TMEM154 polypeptides. Optionally, an antibody according to at least some embodiments of the invention binds to corresponding TMEM154 polypeptides with high affinity, for example with a KD of 10-8 M or less or 10-9 M or less or even 10-10 M or less. The anti-TMEM154 antibodies according to at least some embodiments of the invention optionally exhibit one or more of the following characteristics:

(i) binds to one of the corresponding human TMEM154 polypeptides with a KD of 5×10-8 M or less;

(ii) binds to one of the TMEM154 antigen expressed by multiple myeloma, aggressive and/or drug resistant and/or refractory multiple myeloma cells according to any type or subtype as described herein, but does not substantially bind to normal cells. In addition, optionally these antibodies and conjugates thereof will be effective in eliciting selective killing of such cancer cells and for modulating immune responses involved in autoimmunity and cancer.

Optionally, the antibody binds to one of the corresponding human TMEM154 antigens with a KD of 3×10-8 M or less, or with a KD of 1×10-9 M or less, or with a KD of 0.1×10-9 M or less, or with a KD Of 0.05×10-9 M or less or with a KD of between 1×10-9 and 1×10-11 M.

Standard assays to evaluate the binding ability of the antibodies toward TMEM154 polypeptides are known in the art, including for example, ELISAs, Western blots and RIAs. Suitable assays are described in detail in the Examples. The binding kinetics (e.g., binding affinity) of the antibodies also can be assessed by standard assays known in the art, such as by Biacore analysis.

Upon production of anti-TMEM154 antibody sequences from antibodies can bind to TMEM154 the VH and VL sequences can be "mixed and matched" to create other TMEM154 binding molecules according to at least some embodiments of the invention. TMEM154 binding of such "mixed and matched" antibodies can be tested using the binding assays described above. e.g., ELISAs). Optionally, when VH and VL chains are mixed and matched, a VH sequence from a particular VH/VL pairing is replaced with a structurally similar VH sequence. Likewise, optionally a VL sequence from a particular VH/VL pairing is replaced with a structurally similar VL sequence. For example, the VH and VL sequences of homologous antibodies are particularly amenable for mixing and matching.

Antibodies Having Particular Germline Sequences

In certain embodiments, an antibody according to at least some embodiments of the invention comprises a heavy chain variable region from a particular germline heavy chain immunoglobulin gene and/or a light chain variable region from a particular germline light chain immunoglobulin gene.

As used herein, a human antibody comprises heavy or light chain variable regions that is "the product of" or "derived from" a particular germline sequence if the variable regions of the antibody are obtained from a system that uses human germline immunoglobulin genes.

Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody.

A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95, 96, 97, 98 or 99%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Homologous Antibodies

In yet another embodiment, an antibody according to at least some embodiments of the invention comprises heavy and light chain variable regions comprising amino acid sequences that are homologous to isolated Anti-TMEM154 amino acid sequences of preferred Anti-TMEM154 antibodies, respectively, wherein the antibodies retain the desired functional properties of the parent Anti-TMEM154 antibodies.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package (available commercially), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences according to at least some embodiments of the present invention can further be used as a "query sequence" to perform a search against public databases to, for example, identify related sequences. Such searches can be performed using the XBLAST program (version 2.0) of Altschul, et al. (1990) J Mol. Biol. 215:403-10. BLAST protein searches can be performed with the XBLAST program, score=50, wordlength=3 to obtain amino acid sequences homologous to the antibody molecules according to at least some embodiments of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used.

Antibodies with Conservative Modifications

In certain embodiments, an antibody according to at least some embodiments of the invention comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on preferred Anti-TMEM154 antibodies isolated and produced using methods herein, or conservative modifications thereof, and wherein the antibodies retain the desired functional properties of the Anti-TMEM154 antibodies according to at least some embodiments of the invention, respectively.

In various embodiments, the anti-TMEM154 antibody can be, for example, human antibodies, humanized antibodies or chimeric antibodies.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody according to at least some embodiments of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody according to at least some embodiments of the invention can be replaced with other amino acid residues from the same side chain family and the altered antibody can be tested for retained function (i.e., the functions set forth in (c) through (j) above) using the functional assays described herein.

Engineered and Modified Antibodies

An antibody according to at least some embodiments of the invention can be prepared using an antibody having one or more of the VH and/or VL sequences derived from an anti-TMEM154 antibody starting material to engineer a modified antibody, which modified antibody may have altered properties from the starting antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant regions, for example to alter the effector functions of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332:323-327; Jones, P. et al. (1986) Nature 321:522-525; Queen, C. et al. (1989) Proc. Natl. Acad. See. U.S.A. 86:10029-10033; U.S. Pat. No. 5,225,539 to Winter, and U.S. Pat. Nos. 5,530,101; 5,585,089; 5,693,762 and 6,180,370 to Queen et al.)

Suitable framework sequences can be obtained from public DNA databases or published references that include germline antibody gene sequences. For example, germline DNA sequences for human heavy and light chain variable region genes can be found in the "VBase" human germline sequence database (available on the Internet), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline VH Sequences Reveals about Fifty Groups of VH Segments with Different Hypervariable Loops" J. Mol. Biol. 227:776-798; and Cox, J. P. L. et al. (1994) "A Directory of Human Germline VH Segments Reveals a Strong Bias in their Usage" Eur. J Immunol. 24:827-836; the contents of each of which are expressly incorporated herein by reference.

Another type of variable region modification is to mutate amino acid residues within the VH and/or VL CDR 1, CDR2 and/or CDR3 regions to thereby improve one or more binding properties (e.g., affinity) of the antibody of interest. Site-directed mutagenesis or PCR-mediated mutagenesis can be performed to introduce the mutations and the effect on antibody binding, or other functional property of interest, can be evaluated in appropriate in vitro or in vivo assays. Optionally conservative modifications (as discussed above) are introduced. The mutations may be amino acid substitutions, additions or deletions, but are preferably substitutions. Moreover, typically no more than one, two, three, four or five residues within a CDR region are altered.

Engineered antibodies according to at least some embodiments of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived.

In addition or alternative to modifications made within the framework or CDR regions, antibodies according to at least some embodiments of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody according to at least some embodiments of the invention may be chemically modified (e.g., one or more chemical moieties can be attached to the antibody) or be modified to alter its glycosylation, again to alter one or more functional properties of the antibody. Such embodiments are described further below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for Fc grammar, Fc gamma RII, Fc gammaRIII and FcRn have been mapped and variants with improved binding have been described (see Shields, R. L. et al. (2001) J. Biol. Chem. 276:6591-6604). Specific mutations at positions 256, 290, 298, 333, 334 and 339 are shown to improve binding to FcγRIII. Additionally, the following combination mutants are shown to improve Fcgamma.RIII binding: T256A/S298A, S298A/E333A, S298A/K224A and S298A/E333A/K334A.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies according to at least some embodiments of the invention to thereby produce an antibody with altered glycosylation. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their carbohydrates. The Ms704, Ms705, and Ms709 FUT8.−/− cell lines are created by the targeted disruption of the FUT8 gene in CHO/DG44 cells using two replacement vectors (see U.S. Patent Publication No. 20040110704 by Yamane et al. and Yamane-Ohnuki et al. (2004) Biotechnol Bioeng 87:614-22). As another example, EP 1,176,195 by Hanai et al. describes a cell line with a functionally disrupted FUT8 gene, which encodes a fucosyl transferase, such that antibodies expressed in such a cell line exhibit hypofucosylation by reducing or eliminating the alpha 1,6 bond-related enzyme. Hanai et al. also describe cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) J. Biol. Chem. 277: 26733-26740). PCT Publication WO 99/54342 by Umana et al. describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) Nat. Biotech. 17:176-180). Alternatively, the fucose residues of the antibody may be cleaved off using a fucosidase enzyme. For example, the fucosidase alpha-L-fucosidase removes fucosyl residues from antibodies (Tarentino, A. L. et al. (1975) Biochem. 14:5516-23).

Another modification of the antibodies herein that is contemplated by the invention is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Optionally, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies according to at least some embodiments of the invention. See for example, EP 0 154 316 by Nishimura et al. and EP 0 401 384 by Ishikawa et al.

Methods of Engineering Antibodies

As discussed above, the anti-TMEM154 antibodies having VH and VK sequences disclosed herein can be used to create new anti-TMEM154 antibodies, respectively, by modifying the VH and/or VL sequences, or the constant regions attached thereto. Thus, according to at least some embodiments of the invention, the structural features of an anti-TMEM154 antibody according to at least some embodiments of the invention, are used to create structurally related anti-TMEM154 antibodies that retain at least one functional property of the antibodies according to at least some embodiments of the invention, such as binding to human TMEM154, respectively. For example, one or more CDR regions of one TMEM154 antibody or mutations thereof, can be combined recombinantly with known framework regions and/or other CDRs to create additional, recombinantly-engineered, Anti-TMEM154 antibodies according to at least some embodiments of the invention, as discussed above. Other types of modifications include those described in the previous section. The starting material for the engineering method is one or more of the VH and/or VK sequences provided herein, or one or more CDR regions thereof. To create the engineered antibody, it is not necessary to actually prepare (i.e., express as a protein) an antibody having one or more of the VH and/or VK sequences provided herein, or one or more CDR regions thereof. Rather, the information contained in the sequences is used as the starting material to create a "second generation" sequences derived from the original sequences and then the "second generation" sequences is prepared and expressed as a protein.

Standard molecular biology techniques can be used to prepare and express altered antibody sequence.

Optionally, the antibody encoded by the altered antibody sequences is one that retains one, some or all of the functional properties of the anti-TMEM154 antibodies, respectively, produced by methods and with sequences provided herein, which functional properties include binding to TMEM154 antigen with a specific KD level or less and/or selectively binding to desired target cells such as multiple myeloma, aggressive and/or drug resistant and/or refractory multiple myeloma, that express TMEM154 antigen.

The functional properties of the altered antibodies can be assessed using standard assays available in the art and/or described herein.

In certain embodiments of the methods of engineering antibodies according to at least some embodiments of the invention, mutations can be introduced randomly or selectively along all or part of an anti-TMEM154 antibody coding sequence and the resulting modified anti-TMEM154 antibodies can be screened for binding activity and/or other desired functional properties.

Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies

According to at least some embodiments of the invention pertains to nucleic acid molecules that encode the antibodies according to at least some embodiments of the invention. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid according to at least some embodiments of the invention can be, for example, DNA or RNA and may or may not contain intronic sequences. In a preferred embodiment, the nucleic acid is a cDNA molecule.

Nucleic acids according to at least some embodiments of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker.

The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region.

To create a scFv gene, the VH- and VL-encoding DNA fragments are operatively linked to another fragment encoding a flexible linker, e.g., encoding the amino acid sequence (Gly4-Ser)$_3$, such that the VH and VL sequences can be expressed as a contiguous single-chain protein, with the VL and VH regions joined by the flexible linker (see e.g., Bird et al. (1988) Science 242:423-426; Huston et al. (1988) Proc. Natl. Acad. Sci. USA 85:5879-5883; McCafferty et al., (1990) Nature 348:552-554).

Production of Anti-TMEM154 Monoclonal Antibodies

Monoclonal antibodies (mAbs) according to at least some embodiments of the present invention can be produced by a variety of techniques, including conventional monoclonal antibody methodology e.g., the standard somatic cell hybridization technique of Kohler and Milstein (1975) Nature 256: 495. Although somatic cell hybridization procedures are preferred, in principle, other techniques for producing monoclonal antibody can be employed e.g., viral or oncogenic transformation of B lymphocytes.

A preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized antibodies according to at least some embodiments of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In a preferred embodiment, the antibodies according to at least some embodiments of the invention are human monoclonal antibodies. Such human monoclonal antibodies directed against TMEM154 can be generated using transgenic or transchromosomic mice carrying parts of the human immune system rather than the mouse system. These transgenic and transchromosomic mice include mice referred to herein as the HuMAb Mouse® and KM Mouse® respectively, and are collectively referred to herein as "human Ig mice." The HuMAb Mouse™. (Medarex. Inc.) contains human immunoglobulin gene miniloci that encode unrearranged human heavy (.mu. and .gamma.) and .kappa. light chain immunoglobulin sequences, together with targeted mutations that inactivate the endogenous .mu. and .kappa. chain loci (see e.g., Lonberg, et al. (1994) Nature 368(6474): 856-859). Accordingly, the mice exhibit reduced expression of mouse IgM or .kappa., and in response to immunization, the introduced human heavy and light chain transgenes undergo class switching and somatic mutation to generate high affinity human IgGkappa. monoclonal (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. 13: 65-93, and Harding, F. and Lonberg, N. (1995) Ann. N.Y. Acad. Sci. 764: 536-546). The preparation and use of the HuMab Mouse®, and the genomic modifications carried by such mice, is further described in Taylor, L. et al. (1992) Nucleic Acids Research 20:6287-6295; Chen, J. et al. (1993) International Immunology 5:647-656; Tuaillon et al. (1993) Proc. Natl. Acad. Sci. USA 90:3720-3724; Choi et al. (1993) Nature Genetics 4:117-123; Chen, J. et al. (1993) EMBO J. 12: 821-830; Tuaillon et al. (1994) J. Immunol. 152:2912-2920; Taylor, L. et al. (1994) International Immunology 6:579-591; and Fishwild, D. et al. (1996) Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789, 650; 5,877,397; 5,661,016; 5,814,318; 5,874,299; and 5,770, 429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies according to at least some embodiments of the invention can be raised using a mouse that carries human immunoglobulin sequences on transgenes and transchomosomes, such as a mouse that carries a human heavy chain transgene and a human light chain transchromosome. Such mice, referred to herein as "KM Mice™.", are described in detail in PCT Publication WO 02/43478 to Ishida et al.

Still further, alternative transgenic animal systems expressing human immunoglobulin genes are available in the art and can be used to raise anti-TMEM154 antibodies according to at least some embodiments of the invention. For example, an alternative transgenic system referred to as the Xenomouse (Abgenix, Inc.) can be used; such mice are described in, for example, U.S. Pat. Nos. 5,939,598; 6,075,181; 6,114,598; 6, 150,584 and 6,162,963 to Kucherlapati et al.

Moreover, alternative transchromosomic animal systems expressing human immunoglobulin genes are available in the art and can be used to raise Anti-TMEM154 antibodies according to at least some embodiments of the invention. For example, mice carrying both a human heavy chain transchromosome and a human light chain transchromosome, referred to as "TC mice" can be used; such mice are described in Tomizuka et al. (2000) Proc. Natl. Acad Sci. USA 97:722-727. Furthermore, cows carrying human heavy and light chain transchromosomes have been described in the art (Kuroiwa et al. (2002) Nature Biotechnology 20:889-894) and can be used to raise Anti-TMEM154 antibodies according to at least some embodiments of the invention.

Human monoclonal antibodies according to at least some embodiments of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies according to at least some embodiments of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Immunization of Human Ig Mice

When human Ig mice are used to raise human antibodies according to at least some embodiments of the invention, such mice can be immunized with a purified or enriched preparation of TMEM154 antigen and/or recombinant TMEM154, or an TMEM154 fusion protein, as described by Lonberg, N. et al. (1994) Nature 368(6474): 856-859; Fishwild, D. et al. (1996) Nature Biotechnology 14: 845-851; and PCT Publication WO 98/24884 and WO 01/14424. Preferably, the mice will be 6-16 weeks of age upon the first infusion. For example, a purified or recombinant preparation (5-50 .mu.g) of TMEM154 antigen can be used to immunize the human Ig mice intraperitoneally.

Prior experience with various antigens by others has shown that the transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA (as described below), and mice with sufficient titers of anti-TMEM154 human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCo 12 strains are used. In addition, both HCo7 and HCo12 transgene can be bred together into a single mouse having two different human heavy chain transgenes (HCo7/HCo 12). Alternatively or additionally, the KM Mouse® strain can be used.

Generation of Hybridomas Producing Human Monoclonal Antibodies

To generate hybridomas producing human monoclonal antibodies according to at least some embodiments of the invention, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3x63-Ag8.653 nonsecreting mouse myeloma cells (ATCC, CRL 1580) with 50% PEG. Cells are plated at approximately 2×10-5 in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1xHAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-Sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80 degrees C.

Generation of Transfectomas Producing Monoclonal Antibodies

Antibodies according to at least some embodiments of the invention also can be produced in a host cell transfectoma using, for example, a combination of recombinant DNA techniques and gene transfection methods as is well known in the art (e.g., Morrison, S. (1985) Science 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the VH segment is operatively linked to the CH segments within the vector and the VK segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors according to at least some embodiments of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or .beta.-globin promoter. Still further, regulatory elements composed of sequences from different sources, such as the SR alpha. promoter system, which contains sequences from the SV40 early promoter and the long terminal repeat of human T cell leukemia virus type 1 (Takebe, Y. et al. (1988) Mol. Cell. Biol. 8:466-472).

In addition to the antibody chain genes and regulatory sequences, the recombinant expression vectors according to at least some embodiments of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vectors encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies according to at least some embodiments of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) Immunology Today 6:12-13).

Preferred mammalian host cells for expressing the recombinant antibodies according to at least some embodiments of the invention include Chinese Hamster Ovary (CHO cells) (including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, preferably, secretion of the antibody into the culture medium in which the host cells are grown. Antibodies can be recovered from the culture medium using standard protein purification methods.

Characterization of Antibody Binding to Antigen

Antibodies according to at least some embodiments of the invention can be tested for binding to TMEM154 by, for example, standard ELISA. Briefly, microtiter plates are coated with purified TMEM154 at 0.25 .mu.g/ml in PBS, and then blocked with 5% bovine serum albumin in PBS. Dilutions of antibody (e.g., dilutions of plasma from TMEM154-immunized mice) are added to each well and incubated for 1-2 hours at 37 degrees C. The plates are washed with PBS/Tween and then incubated with secondary reagent (e.g., for human antibodies, a goat-anti-human IgG Fc-specific polyclonal reagent) conjugated to alkaline phosphatase for 1 hour at 37 degrees C. After washing, the plates are developed with pNPP substrate (1 mg/ml), and analyzed at OD of 405-650. Preferably, mice which develop the highest titers will be used for fusions.

An ELISA assay as described above can also be used to screen for hybridomas that show positive reactivity with TMEM154 immunogen. Hybridomas that bind with high avidity to TMEM154 are subcloned and further characterized. One clone from each hybridoma, which retains the reactivity of the parent cells (by ELISA), can be chosen for making a 5-10 vial cell bank stored at −140 degrees C., and for antibody purification.

To purify anti-TMEM154 antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80 degrees C.

To determine if the selected anti-TMEM154 monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using TMEM154 coated-ELISA plates as described above. Biotinylated mAb binding can be detected with a strep-avidin-alkaline phosphatase probe.

To determine the isotype of purified antibodies, isotype ELISAs can be performed using reagents specific for antibodies of a particular isotype. For example, to determine the isotype of a human monoclonal antibody, wells of microtiter plates can be coated with 1 .mu.g/ml of anti-human immunoglobulin overnight at 4 degrees C. After blocking with 1% BSA, the plates are reacted with 1 mug/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

Anti-TMEM154 human IgGs can be further tested for reactivity with TMEM154 antigen, respectively, by Western blotting. Briefly, TMEM154 antigen can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Conjugates or Immunoconjugates

According to at least some embodiments, the present invention features immunoconjugates comprising anti-TMEM154 antibody, or a fragment thereof, conjugated to a therapeutic moiety, such as a cytotoxin, a drug (e.g., an immunosuppressant) or a radiotoxin. Such conjugates are referred to herein as "immunoconjugates" Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other preferred examples of therapeutic cytotoxins that can be conjugated to an antibody according to at least some embodiments of the invention include duocarmycins, calicheamicins, maytansines and auristatins, and derivatives thereof. An example of a calicheamicin antibody conjugate is commercially available (Mylotarg™; Wyeth).

Cytotoxins can be conjugated to antibodies according to at least some embodiments of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al. (2003) Adv. Drug Deliv. Rev. 55:199-215; Trail, P. A. et al. (2003) Cancer Immunol. Immunother. 52:328-337; Payne, G. (2003) Cancer Cell 3:207-212; Allen, T. M. (2002) Nat. Rev. Cancer 2:750-763; Pastan, I. and Kreitman, R. J. (2002) Curr. Opin. Investig. Drugs 3:1089-1091; Senter, P. D. and Springer, C. J. (2001) Adv. Drug Deliv. Rev. 53:247-264.

Antibodies according to at least some embodiments of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine 131, indium 111, yttrium 90 and lutetium 177. Method for preparing radioimmunconjugates are established in the art. Examples of radioimmunoconjugates are commercially available, including Zevalin™ (IDEC Pharmaceuticals) and Bexxar™ (Corixa Pharmaceuticals), and similar methods can be used to prepare radioimmunoconjugates using the antibodies according to at least some embodiments of the invention.

The antibody conjugates according to at least some embodiments of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-.gamma.; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Bispecific Molecules

In another aspect, the present invention features bispecific molecules comprising an anti-TMEM154 antibody, or a fragment thereof, according to at least some embodiments of the invention. An antibody according to at least some embodiments of the invention, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody according to at least some embodiments of the invention may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule according to at least some embodiments of the invention, an antibody according to at least some embodiments of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for a TMEM154 polypeptide and a second binding specificity for a second target epitope. In a particular embodiment according to at least some embodiments of the invention, the second target epitope is an Fc receptor, e.g., human Fc gamma R1 (CD64) or a human Fc alpha receptor (CD89). Therefore, the invention includes bispecific molecules capable of binding both to Fc gamma. R, Fc alpha R or Fc epsilon R expressing effector cells (e.g., monocytes, macrophages or polymorphonuclear cells (PMNs)), and to target cells expressing a TMEM154 polypeptide, respectively. These bispecific molecules target TMEM154 polypeptide expressing cells to effector cell and trigger Fc receptor-mediated effector cell activities, such as phagocytosis of TMEM154 polypeptide expressing cells, antibody dependent cell-mediated cytotoxicity (ADCC), cytokine release, or generation of superoxide anion.

In an embodiment according to at least some embodiments of the invention in which the bispecific molecule is multispecific, the molecule can further include a third binding specificity, in addition to an anti-Fc binding specificity and an anti-6f binding specificity. In one embodiment, the third binding specificity is an anti-enhancement factor (EF) portion, e.g., a molecule which binds to a surface protein involved in cytotoxic activity and thereby increases the immune response against the target cell.

The "anti-enhancement factor portion" can be an antibody, functional antibody fragment or a ligand that binds to a given molecule, e.g., an antigen or a receptor, and thereby results in an enhancement of the effect of the binding determinants for the Fc receptor or target cell antigen. The "anti-enhancement factor portion" can bind an Fc receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g., via CD2, CD3, CD8, CD28, CD4, CD40, ICAM-1 or other immune cell that results in an increased immune response against the target cell).

In one embodiment, the bispecific molecules according to at least some embodiments of the invention comprise as a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which is expressly incorporated by reference.

The production and characterization of certain preferred anti-Fc gamma. monoclonal antibodies are described by Fanger et al. in PCT Publication WO 88/00052 and in U.S. Pat. No. 4,954,617, the teachings of which are fully incorporated by reference herein. These antibodies bind to an epitope of Fc R1, FcγRII or FcγRIII at a site which is distinct from the Fc binding site of the receptor and, thus, their binding is not blocked substantially by physiological levels of IgG. Specific anti-Fc RI antibodies useful in this invention are mAb 22, mAb 32, mAb 44, mAb 62 and mAb 197. The hybridoma producing mAb 32 is available from the American Type Culture Collection, ATCC Accession No. HB9469. In other embodiments, the anti-Fcγ receptor antibody is a humanized form of monoclonal antibody 22 (H22). The production and characterization of the H22 antibody is described in Graziano, R. F. et al. (1995) J. Immunol. 155 (10): 4996-5002 and PCT Publication WO 94/10332. The H22 antibody producing cell line is deposited at the American Type Culture Collection under the designation HAO22CLI and has the accession no. CRL 11177.

In still other preferred embodiments, the binding specificity for an Fc receptor is provided by an antibody that binds to a human IgA receptor, e.g., an Fc-alpha receptor (Fc alpha RI(CD89)), the binding of which is preferably not blocked by human immunoglobulin A (IgA). The term "IgA receptor" is intended to include the gene product of one alpha.-gene (Fc alpha RI) located on chromosome 19. This gene is known to encode several alternatively spliced transmembrane isoforms of 55 to 10 kDa.

Fc alpha RI (CD89) is constitutively expressed on monocytes/macrophages, eosinophilic and neutrophilic granulocytes, but not on non-effector cell populations. Fc alpha RI has medium affinity (Approximately 5×10-7 M-1) for both IgA1 and IgA2, which is increased upon exposure to cytokines such as G-CSF or GM-CSF (Morton, H. C. et al. (1996) Critical Reviews in Immunology 16:423-440). Four Fcα RI-specific monoclonal antibodies, identified as A3, A59, A62 and A77, which bind Fc alpha I outside the IgA ligand binding domain, have been described (Monteiro, R. C. et al. (1992) J. Immunol. 148:1764).

Fc alpha RI and Fc gamma RI are preferred trigger receptors for use in the bispecific molecules according to at least some embodiments of the invention because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); (4) mediate enhanced antigen presentation of antigens, including self-antigens, targeted to them.

While human monoclonal antibodies are preferred, other antibodies which can be employed in the bispecific molecules according to at least some embodiments of the invention are murine, chimeric and humanized monoclonal antibodies.

The bispecific molecules according to at least some embodiments of the present invention can be prepared by conjugating the constituent binding specificities, e.g., the anti-FcR and anti-TMEM154 polypeptide binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl)cyclohaxane-1-carboxylate (sulfo-SMCC) (see e.g., Karpovsky et al. (1984) J. Exp. Med. 160:1686; Liu, M A et al. (1985) Proc. Natl. Acad. Sci. USA 82:8648). Other methods include those described in Paulus (1985) Behring Ins. Mitt. No. 78, 118-132; Brennan et al. (1985) Science 229:81-83), and Glennie et al. (1987) J. Immunol. 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAbXmAb, mAbXFab, FabXF(ab')2 or ligandXFab fusion protein. A bispecific molecule according to at least some embodiments of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a gamma. counter or a scintillation counter or by autoradiography.

Pharmaceutical Compositions

In another aspect, the present invention provides a composition, e.g., a pharmaceutical composition, containing one or a combination of monoclonal antibodies, or antigen-binding portions thereof, according to at least some embodiments of the present invention, formulated together with a pharmaceutically acceptable carrier. Such compositions may include one or a combination of (e.g., two or more different) antibodies, or immunoconjugates or bispecific molecules according to at least some embodiments of the invention. For example, a pharmaceutical composition according to at least some embodiments of the invention can comprise a combination of antibodies (or immunoconjugates or bispecifics) that bind to different epitopes on the target antigen or that have complementary activities.

As discussed supra, at least some embodiments of the present invention further embrace identifying other molecules such as small organic molecules, peptides, ribozymes, carbohydrates, glycoprotein, siRNAs, antisense RNAs and the like which specifically bind and/or modulate (enhance or inhibit) an activity elicited by the TMEM154 antigen or polypeptides, respectively. These molecules may be identified by known screening methods such as binding assays. Typically these assays will be high throughput and will screen a large library of synthesized or native compounds in order to identify putative drug candidates that bind and/or modulate TMEM154 related activities.

Specifically, the invention embraces the development of drugs containing the ectodomain of the TMEM154 antigen or polypeptide, or a fragment or variant thereof or a corresponding nucleic acid sequence encoding.

Thus, the present invention features a pharmaceutical composition comprising a therapeutically effective amount of a therapeutic agent according to the present invention. According to the present invention the therapeutic agent could be any one of TMEM154 ectodomain, or a fragment or a variant or a conjugate thereof, or a corresponding nucleic acid sequence encoding same.

The pharmaceutical composition according to the present invention is further optionally used for the treatment of multiple myeloma, aggressive and/or drug resistant and/or refractory multiple myeloma conditions or disorders. The pharmaceutical composition may optionally further comprise, in addition to the various embodiments of the present invention, one or more additional treatments for multiple myeloma. Such one or more additional treatments could easily be selected by one of ordinary skill in the art. The one or more additional treatments may optionally be administered concurrently or sequentially, or in combination with the actual pharmaceutical composition.

The therapeutic agents according to at least some embodiments of the present invention can be provided to the subject alone, or as part of a pharmaceutical composition where they are mixed with a pharmaceutically acceptable carrier.

Pharmaceutical compositions according to at least some embodiments of the invention also can be administered in combination therapy, i.e., combined with other agents. For example, the combination therapy can include anti-TMEM154 antibody or TMEM154 modulating agent according to the present invention such as a soluble polypeptide conjugate containing the ectodomain of the TMEM154 polypeptide or a small molecule such as a peptide, ribozyme, siRNA, or other drug that binds a TMEM154 polypeptide, combined with at least one other therapeutic or immune modulatory agent.

A composition according to at least some embodiments of the present invention can be administered via one or more routes of administration using one or more of a variety of methods known in the art. As will be appreciated by the skilled artisan, the route and/or mode of administration will vary depending upon the desired results. Preferred routes of administration for therapeutic agents of the invention include intravascular delivery (e.g. injection or infusion), intravenous, intramuscular, intradermal, intraperitoneal, subcutaneous, spinal, oral, enteral, rectal, pulmonary (e.g. inhalation), nasal, topical (including transdermal, buccal and sublingual), intravesical, intravitreal, intraperitoneal, vaginal, brain delivery (e.g. intra-cerebroventricular, intra-cerebral, and convection enhanced diffusion), CNS delivery (e.g. intrathecal, perispinal, and intra-spinal) or parenteral (including subcutaneous, intramuscular, intravenous and intradermal), transmucosal (e.g., sublingual administration), administration or administration via an implant, or other parenteral routes of administration, for example by injection or infusion, or other delivery routes and/or forms of administration known in the art. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate the compound.

A pharmaceutical composition according to at least some embodiments of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like. Examples of suitable aqueous and nonaqueous carriers that may be employed in the pharmaceutical compositions according to at least some embodiments of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions according to at least some embodiments of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin. Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, optionally from about 0.1 percent to about 70 percent, optionally from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms according to at least some embodiments of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions according to at least some embodiments of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions according to at least some embodiments of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-TMEM154 antibody according to at least some embodiments of the invention preferably results in a decrease in severity of disease symptoms, an increase in frequency and duration of disease symptom-free periods, an increase in lifespan, disease remission, or a prevention of impairment or disability due to the disease affliction. For example, for the treatment of TMEM154 polypeptide positive tumors, e.g., multiple myeloma, aggressive and/or drug resistant and/or refractory multiple myeloma, a "therapeutically effective dosage" optionally inhibits cell growth or tumor growth by at least about 20%, 40%, 60%, 80% relative to untreated subjects. The ability of a compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner. Alternatively or additionally, the suitable amount or dosage may also optionally be at least partially selected according to the administration of one or more additional treatments for multiple myeloma, which may optionally and preferably have a synergistic effect and so which may optionally cause the dosage amount to be adjusted. Such one or more additional treatments could easily be selected by one of ordinary skill in the art.

Alternatively or additionally, a "therapeutically effective dosage" preferably results in at least stable disease, preferably partial response, more preferably complete response, as assessed by the WHO or RECIST criteria for tumor response (Natl Cancer Inst 1999; 91:523-8 and Cancer 1981; 47:207-14).

A therapeutically effective amount of a therapeutic compound can decrease tumor size, or otherwise ameliorate symptoms in a subject, or otherwise support partial or complete stable disease and/or partial or complete response as determined above. One of ordinary skill in the art would be able to determine such amounts based on such factors as the subject's size, the severity of the subject's symptoms, and the particular composition or route of administration selected.

Therapeutic compositions can be administered with medical devices known in the art. For example, in a preferred embodiment, a therapeutic composition according to at least some embodiments of the invention can be administered with a needles hypodermic injection device, such as the devices disclosed in U.S. Pat. No. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the antibodies or other TMEM154 related drugs according to at least some embodiments of the invention can be formulated to ensure proper distribution in vivo. For example, the blood-brain barrier (BBB) excludes many highly hydrophilic compounds. To ensure that the therapeutic compounds according to at least some embodiments of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J Physiol. 1233:134); p120 (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273.

Given the specific binding of the antibodies according to at least some embodiments of the invention for TMEM154 polypeptides, the antibodies can be used to specifically detect TMEM154 expression on the surface of cells and, moreover, can be used to purify or TMEM154 antigen via immunoaffinity purification.

Furthermore, given the expression of TMEM154 polypeptides on various tumor cells, the human antibodies, antibody compositions and methods according to at least some embodiments of the present invention can be used to treat a subject with a tumorigenic disorder, e.g., a disorder characterized by the presence of tumor cells expressing TMEM154 antigen such as multiple myeloma, aggressive and/or drug resistant and/or refractory multiple myeloma, as mentioned.

In one embodiment, the antibodies (e.g., human monoclonal antibodies, multispecific and bispecific molecules and compositions) according to at least some embodiments of the invention can be used to detect levels of a TMEM154 polypeptide or levels of cells which contain a TMEM154 polypeptide, respectively, on their membrane surface, which levels can then be linked to certain disease symptoms.

Alternatively, the antibodies can be used to inhibit or block functioning of TMEM154 polypeptides which, in turn, can be linked to the prevention or amelioration of certain disease symptoms, thereby implicating TMEM154 polypeptides, respectively, as a mediator of the disease. This can be achieved by contacting a sample and a control sample with the anti-TMEM154 antibody under conditions that allow for the formation of a complex between the corresponding antibody and TMEM154 polypeptides, respectively. Any complexes formed between the antibody and TMEM154 polypeptides are detected and compared in the sample and the control.

In another embodiment, the antibodies (e.g., human antibodies, multispecific and bispecific molecules and compositions) according to at least some embodiments of the invention can be initially tested for binding activity associated with therapeutic or diagnostic use in vitro. For example, compositions according to at least some embodiments of the invention can be tested using low cytometric assays.

As previously described, human anti-TMEM154 antibodies according to at least some embodiments of the invention can be co-administered with one or other more therapeutic agents, e.g., an cytotoxic agent, a radiotoxic agent or an immunosuppressive agent. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, and cyclophosphamide hydroxyurea which, by themselves, are only effective at levels which are toxic or subtoxic to a patient. Cisplatin is intravenously administered as a 100 mg/dose once every four weeks and adriamycin is intravenously administered as a 60-75 mg/ml dose once every 21 days. Co-administration of the human anti-TMEM154 antibodies, or antigen binding fragments thereof, according to at least some embodiments of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Also within the scope according to at least some embodiments of the present invention are kits comprising the TMEM154 polypeptide or antibody compositions according to at least some embodiments of the invention (e.g., human antibodies, bispecific or multispecific molecules, or immunoconjugates) and instructions for use. The kit can further contain one ore more additional reagents, such as an immunosuppressive reagent, a cytotoxic agent or a radiotoxic agent, or one or more additional human antibodies according to at least some embodiments of the invention (e.g., a human antibody having a complementary activity which binds to an epitope in the TMEM154 antigen distinct from the first human antibody).

In other embodiments, the subject can be additionally treated with an agent that modulates, e.g., enhances or inhibits, the expression or activity of Fcγ or Fcγ receptors by, for example, treating the subject with a cytokine. Preferred cytokines for administration during treatment with the multispecific molecule include of granulocyte colony-stimulating factor (G-CSF), granulocyte-macrophage colony-stimulating factor (GM-CSF), interferon-.gamma. (IFN-.gamma.), and tumor necrosis factor (TNF).

The compositions (e.g., human antibodies, multispecific and bispecific molecules) according to at least some embodiments of the invention can also be used to target cells expressing Fc gamma R or TMEM154, for example for labeling such cells. For such use, the binding agent can be linked to a molecule that can be detected. Thus, the invention provides methods for localizing ex vivo or in vitro cells expressing Fc receptors, such as FcgammaR, or TMEM154 antigen. The detectable label can be, e.g., a radioisotope, a fluorescent compound, an enzyme, or an enzyme co-factor.

Diagnostic Uses of TMEM154 Polypeptides, Polynucleotides and Antibodies

TMEM154 specific antibodies and/or soluble polypeptides according to at least some embodiments of the present invention may also be modified with a label capable of providing a detectable signal, either directly or indirectly, including, but not limited to, radioisotopes and fluorescent compounds. Such labeled antibodies and/or polypeptides can be used for various uses, including but not limited to, prognosis, prediction, screening, early diagnosis, determination of progression, therapy selection and treatment monitoring of disease and/or an indicative condition, as detailed above, for any suitable type of in vivo and/or in vitro assay as described herein.

In some embodiments, the term "label" includes any moiety or item detectable by spectroscopic, photo chemical, biochemical, immunochemical, or chemical means. For example, useful labels include 32P, 35S, fluorescent dyes, electron-dense reagents, enzymes (e.g., as commonly used in an ELISA), biotin-streptavadin, dioxigenin, haptens and proteins for which antisera or monoclonal antibodies are available, or nucleic acid molecules with a sequence complementary to a target. The label often generates a measurable signal, such as a radioactive, chromogenic, or fluorescent signal, that can be used to quantify the amount of bound label in a sample. The label can be incorporated in or attached to a primer or probe either covalently, or through ionic, van der Waals or hydrogen bonds, e.g., incorporation of radioactive nucleotides, or biotinylated nucleotides that are recognized by streptavadin. The label may be directly or indirectly detectable. Indirect detection can involve the binding of a second label to the first label, directly or indirectly. For example, the label can be the ligand of a binding partner, such as biotin, which is a binding partner for streptavadin, or a nucleotide sequence, which is the binding partner for a complementary sequence, to which it can specifically hybridize. The binding partner may itself be directly detectable, for example, an antibody may be itself labeled with a fluorescent molecule. The binding partner also may be indirectly detectable, for example, a nucleic acid having a complementary nucleotide sequence can be a part of a branched DNA molecule that is in turn detectable through hybridization with other labeled nucleic acid molecules (see, e.g., P. D. Fahrlander and A. Klausner, Bio/Technology 6:1165 (1988)). Quantitation of the signal is achieved by, e.g., scintillation counting, densitometry, or flow cytometry.

Exemplary detectable labels, optionally for use with immunoassays, include but are not limited to magnetic beads, fluorescent dyes, radiolabels, enzymes (e.g., horse radish peroxide, alkaline phosphatase and others commonly used in an ELISA), and calorimetric labels such as colloidal gold or colored glass or plastic beads. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker are incubated simultaneously with the mixture.

Other examples of suitable labels may optionally be used for in vivo imaging and/or labeling. According to at least some embodiments, the present invention provides a method for imaging an organ or tissue, the method comprising: (a) administering to a subject in need of such imaging, a labeled TMEM154 specific antibody and/or polypeptide; and (b) detecting the labeled TMEM154 specific antibody and/or polypeptide to determine where the labeled TMEM154 specific antibody and/or polypeptide is concentrated in the subject. When used in imaging applications, the labeled antibodies and/or polypeptides according to at least some embodiments of the present invention typically have an imaging agent covalently or noncovalently attached thereto. Suitable imaging agents include, but are not limited to, radionuclides, detectable tags, fluorophores, fluorescent proteins, enzymatic proteins, and the like.

One of skill in the art will be familiar with suitable methods for attaching imaging agents to polypeptides. For example, the imaging agent can be attached via site-specific conjugation, e.g., covalent attachment of the imaging agent to a peptide linker such as a polyarginine moiety having five to seven arginines present at the carboxyl-terminus of and Fc fusion molecule. The imaging agent can also be directly attached via non-site specific conjugation, e.g., covalent attachment of the imaging agent to primary amine groups present in the antibody and/or polypeptide. One of skill in the art will appreciate that an imaging agent can also be bound to a protein via noncovalent interactions (e.g., ionic bonds, hydrophobic interactions, hydrogen bonds, Van der Waals forces, dipole-dipole bonds, etc.).

In certain instances, the antibody and/or polypeptide is radiolabeled with a radionuclide by directly attaching the radionuclide to the polypeptide. In certain other instances, the radionuclide is bound to a chelating agent or chelating agent-linker attached to the antibody and/or polypeptide. Suitable radionuclides for direct conjugation include, without limitation, 18 F, 124 I, 125 I, 131 I, and mixtures thereof. Suitable radionuclides for use with a chelating agent include, without limitation, 47 Sc, 64 Cu, 67 Cu, 89 Sr, 86 Y, 87 Y, 90 Y, 105 Rh, 111 Ag, 111 In, 117m Sn, 149 Pm, 153 Sm, 166 Ho, 177 Lu, 186 Re, 188 Re, 211 At, 212 Bi, and mixtures thereof. Preferably, the radionuclide bound to a chelating agent is 64 Cu, 90 Y, 111 In, or mixtures thereof. Suitable chelating agents include, but are not limited to, DOTA, BAD, TETA, DTPA, EDTA, NTA, HDTA, their phosphonate analogs, and mixtures thereof. One of skill in the art will be familiar with methods for attaching radionuclides, chelating agents, and chelating agent-linkers to polypeptides of the present invention. In particular, attachment can be conveniently accomplished using, for example, commercially available bifunctional linking groups (generally heterobifunctional linking groups) that can be attached to a functional group present in a non-interfering position on the antibody and/or polypeptide and then further linked to a radionuclide, chelating agent, or chelating agent-linker.

Non-limiting examples of fluorophores or fluorescent dyes suitable for use as imaging agents include Alexa Fluor® dyes (Invitrogen Corp.; Carlsbad, Calif.), fluorescein, fluorescein isothiocyanate (FITC), Oregon Green™; rhodamine, Texas red, tetrarhodamine isothiocynate (TRITC), CyDye™ fluors (e.g., Cy2, Cy3, Cy5), and the like.

Examples of fluorescent proteins suitable for use as imaging agents include, but are not limited to, green fluorescent protein, red fluorescent protein (e.g., DsRed), yellow fluorescent protein, cyan fluorescent protein, blue fluorescent protein, and variants thereof (see, e.g., U.S. Pat. Nos. 6,403,374, 6,800,733, and 7,157,566). Specific examples of GFP variants include, but are not limited to, enhanced GFP (EGFP), destabilized EGFP, the GFP variants described in Doan et al., Mol. Microbiol., 55:1767-1781 (2005), the GFP variant described in Crameri et al., Nat. Biotechnol., 14:315-319 (1996), the cerulean fluorescent proteins described in Rizzo et al., Nat. Biotechnol, 22:445 (2004) and Tsien, Annu. Rev. Biochem., 67:509 (1998), and the yellow fluorescent protein described in Nagal et al., Nat. Biotechnol., 20:87-90 (2002). DsRed variants are described in, e.g., Shaner et al., Nat. Biotechnol., 22:1567-1572 (2004), and include mStrawberry, mCherry, mOrange, mBanana, mHoneydew, and mTangerine. Additional DsRed variants are described in, e.g., Wang et al., Proc. Natl. Acad. Sci. U.S.A., 101:16745-16749 (2004) and include mRaspberry and mPlum. Further examples of DsRed variants include mRFPmars described in Fischer et al., FEBS Lett., 577:227-232 (2004) and mRFPruby described in Fischer et al., FEBS Lett., 580:2495-2502 (2006).

In other embodiments, the imaging agent that is bound to an antibody and/or polypeptide according to at least some embodiments of the present invention comprises a detectable tag such as, for example, biotin, avidin, streptavidin, or neutravidin. In further embodiments, the imaging agent comprises an enzymatic protein including, but not limited to, luciferase, chloramphenicol acetyltransferase, β-galactosidase, β-glucuronidase, horseradish peroxidase, xylanase, alkaline phosphatase, and the like.

Any device or method known in the art for detecting the radioactive emissions of radionuclides in a subject is suitable for use in the present invention. For example, methods such as Single Photon Emission Computerized Tomography (SPECT), which detects the radiation from a single photon gamma-emitting radionuclide using a rotating gamma camera, and radionuclide scintigraphy, which obtains an image or series of sequential images of the distribution of a radionuclide in tissues, organs, or body systems using a scintillation gamma camera, may be used for detecting the radiation emitted from a radiolabeled polypeptide of the present invention. Positron emission tomography (PET) is another suitable technique for detecting radiation in a subject. Miniature and flexible radiation detectors intended for medical use are produced by Intra-Medical LLC (Santa Monica, Calif.). Magnetic Resonance Imaging (MRI) or any other imaging technique known to one of skill in the art is also suitable for detecting the radioactive emissions of radionuclides. Regardless of the method or device used, such detection is aimed at determining where the labeled polypeptide is concentrated in a subject, with such concentration being an indicator of disease activity.

Non-invasive fluorescence imaging of animals and humans can also provide in vivo diagnostic information and be used in a wide variety of clinical specialties. For instance, techniques have been developed over the years for simple ocular observations following UV excitation to sophisticated spectroscopic imaging using advanced equipment (see, e.g., Andersson-Engels et al., Phys. Med. Biol., 42:815-824 (1997)). Specific devices or methods known in the art for the in vivo detection of fluorescence, e.g., from fluorophores or fluorescent proteins, include, but are not limited to, in vivo near-infrared fluorescence (see, e.g., Frangioni, Curr. Opin. Chem. Biol., 7:626-634 (2003)), the Maestro™ in vivo fluorescence imaging system (Cambridge Research & Instrumentation, Inc.; Woburn, Mass.), in vivo fluorescence imaging using a flying-spot scanner (see, e.g., Ramanujam et al., IEEE Transactions on Biomedical Engineering, 48:1034-1041 (2001), and the like.

Other methods or devices for detecting an optical response include, without limitation, visual inspection, CCD cameras, video cameras, photographic film, laser-scanning devices, fluorometers, photodiodes, quantum counters, epifluorescence microscopes, scanning microscopes, flow cytometers, fluorescence microplate readers, or signal amplification using photomultiplier tubes.

Other suitable assays include without limitation, radioimaging assays, in-vivo imaging, Ultra Sound, Optical Imaging, and/or Computer Tomography.

In certain embodiments the polypeptides and/or polynucleotides according to at least some embodiments of the present invention are used as markers for diagnosis of diseases wherein TMEM154 polypeptides and/or polynucleotides are differentially present. According to at least some embodiments, the diseases are selected from but not limited to multiple myeloma, aggressive and/or drug resistant and/or refractory multiple myeloma (as defined herein).

According to further embodiments markers according to at least some embodiments of the present invention might optionally be used alone or in combination with one or more other compounds described herein, and/or in combination with known markers for hematological cancer, including but not limited to soluble forms of tumor markers like P-Selectin, CD-22, interleukins, cytokines, and/or in combination with the known protein(s) for the variant marker as described herein. For example as previously described, one known marker for multiple myeloma is the secretion of light chain (kappa or gamma). Other markers include but are not limited to the presence of unexplained anemia, kidney dysfunction, a high erythrocyte sedimentation rate (ESR) and a high serum protein (especially raised immunoglobulin). The blood and urine may show the presence of a paraprotein (monoclonal protein, or M protein) band, with or without reduction of the other (normal) immunoglobulins (known as immune paresis); one non-limiting example of a paraprotein is the Bence Jones protein which is a urinary paraprotein composed of free light chains (as described above, these light chains may be kappa or gamma). In the case of a bone marrow biopsy, the percentage of bone marrow occupied by plasma cells is used in the diagnostic criteria for myeloma. Immunohistochemistry (staining particular cell types using antibodies against surface proteins) can detect plasma cells which express immunoglobulin in the cytoplasm but usually not on the surface; myeloma cells are typically CD56, CD38, CD138 positive and CD19 and CD45 negative.

According to some embodiments, the sample taken from a subject to perform a diagnostic assay according to at least some embodiments of the present invention is selected from the group consisting of a body fluid or secretion including but not limited to blood, serum, urine, plasma, prostate fluid, seminal fluid, semen, the external secretions of the skin, respiratory, intestinal, and genitourinary tracts, tears, cerebrospinal fluid, sputum, saliva, milk, peritoneal fluid, pleural fluid, cyst fluid, secretions of the breast ductal system (and/or lavage thereof), broncho alveolar lavage, lavage of the reproductive system and lavage of any other part of the body or system in the body; samples of any organ including isolated cells or tissues, wherein the cell or tissue can be obtained from an organ selected from, but not limited to lung, colon, kidney, pancreas, ovary, prostate, liver, skin, bone marrow, lymph node, breast, and/or blood tissue; stool or a tissue sample, or any combination thereof. Prior to be subjected to the diagnostic assay, the sample can optionally be diluted with a suitable diluent. In certain embodiments, cells obtained from the sample are cultured in vitro prior to performing the diagnostic assay.

Numerous well known tissue or fluid collection methods can be utilized to collect the biological sample from a subject in order to determine the level of nucleic acid and/or polypeptide of the marker of interest in the subject.

Examples include, but are not limited to, fine needle biopsy, needle biopsy, core needle biopsy and surgical biopsy (e.g., brain biopsy), and lavage. Regardless of the procedure employed, once a biopsy/sample is obtained the level of the marker can be determined and a diagnosis can thus be made.

In at least some embodiments the present invention provides variant proteins, which may optionally be used as diagnostic markers, optionally as markers for in vivo imaging as described herein. According to at least some embodiments the present invention therefore overcomes the many deficiencies of the background art with regard to the need to obtain tissue samples and subjective interpretations of results. As in vivo imaging markers, the markers according to at least some embodiments of the present invention may also provide different and/or better measurement parameters for various diseases and/or pathological conditions.

In at least some embodiments the present invention further relates to diagnostic assays for detecting a disease, particularly in a sample taken from a subject (patient), optionally a blood sample or a body secretion sample. In at least some embodiments of the present invention, the diagnostic assays are immunoassays, including, for example and without limitation, any of the previously described in vivo assays and/or in vitro assays, immunohistochemical assay, radioimmunoassay (RIA), ELISA, slot blot, competitive binding assays, fluorimetric imaging assays, Western blot, FACS, and the like. According to another embodiments, the diagnostic assays are NAT (nucleic acid amplification technology)-based assays, including, for example, nucleic acid hybridization assays, PCR or variations thereof, e.g. real-time PCR. The diagnostic assays can be qualitative or quantitative.

In some embodiments, the phrase "differentially present" refers to differences in the quantity of a marker present in a sample taken from subjects having one of the herein-described diseases or conditions as compared to a comparable sample taken from subjects who do not have one of the herein-described diseases or conditions. For example, a nucleic acid fragment may optionally be differentially present between the two samples if the amount of the nucleic acid fragment in one sample is significantly different from the amount of the nucleic acid fragment in the other sample, for example as measured by hybridization and/or NAT-based assays. A polypeptide is differentially present between the two samples if the amount of the polypeptide in one sample is significantly different from the amount of the polypeptide in the other sample. It should be noted that if the marker is detectable in one sample and not detectable in the other, then such a marker can be considered to be differentially present. Optionally, a relatively low amount of up-regulation may serve as the marker, as described herein. One of ordinary skill in the art could easily determine such relative levels of the markers; further guidance is provided in the description of each individual marker below.

The term "marker" in the context of the present invention refers to a nucleic acid fragment, a peptide, or a polypeptide, which is differentially present in a sample taken from subjects having one of the herein-described diseases or conditions, as compared to a comparable sample taken from subjects who do not have one the above-described diseases or conditions.

According to at least some embodiments of the present invention, a diagnostic assay can provide qualitative or quantitative information on the level of the markers in the sample.

In some embodiments, the phrase "qualitative" when in reference to differences in expression levels of a polynucleotide or polypeptide as described herein, refers to the presence versus absence of expression, or in some embodiments, the temporal regulation of expression, or in some embodiments, the timing of expression, or in some embodiments, any post-translational modifications to the expressed molecule, and others, as will be appreciated by one skilled in the art. In some embodiments, the phrase "quantitative" when in reference to differences in expression levels of a polynucleotide or polypeptide as described herein, refers to absolute differences in quantity of expression, as determined by any means, known in the art, or in other embodiments, relative differences, which may be statistically significant, or in some embodiments, when viewed as a whole or over a prolonged period of time, etc., indicate a trend in terms of differences in expression.

The term "level" refers to expression levels of nucleic acids (e.g. RNA) and/or polypeptides of the marker according to at least some embodiments of the present invention.

In certain embodiments, the diagnostic markers according to at least some embodiments of the invention are correlated to a condition or disease by their mere presence or absence. In other embodiments, threshold levels of the diagnostic markers can be established, and the level of the markers in a patient's sample can be compared to the threshold levels.

In some embodiments, the term "test amount" of a marker refers to an amount of a marker in a subject's sample that is consistent with a diagnosis of a particular disease or condition. A test amount can be either in absolute amount (e.g., microgram/ml) or a relative amount (e.g., relative intensity of signals).

In some embodiments, the term "control amount" of a marker can be any amount or a range of amounts to be compared against a test amount of a marker. For example, a control amount of a marker can be the amount of a marker in a patient with a particular disease or condition or a person without such a disease or condition. A control amount can be either in absolute amount (e.g., microgram/ml) or a relative amount (e.g., relative intensity of signals).

In some embodiments, the term "detect" refers to identifying the presence, absence or amount of the object to be detected.

The phrase "specifically (or selectively) binds" to an antibody or "specifically (or selectively) immunoreactive with," or "specifically interacts or binds" when referring to a protein or peptide (or other epitope), refers, in some embodiments, to a binding reaction that is determinative of the presence of the protein in a heterogeneous population of proteins and other biologics. Thus, under designated immunoassay conditions, the specified antibodies bind to a particular protein at least two times greater than the background (non-specific signal) and do not substantially bind in a significant amount to other proteins present in the sample. Specific binding to an antibody under such conditions may require an antibody that is selected for its specificity for a particular protein. For example, polyclonal antibodies raised to seminal basic protein from specific species such as rat, mouse, or human can be selected to obtain only those polyclonal antibodies that are specifically immunoreactive with seminal basic protein and not with other proteins, except for polymorphic variants and alleles of seminal basic protein. This selection may be achieved by subtracting out antibodies that cross-react with seminal basic protein molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background. Diagnostic assays according to at least some embodiments of the present invention include, but are not limited to immunoassays and nucleic acid based assays. "Immunoassay" is an assay that uses an antibody to specifically bind an antigen. The immunoassay is characterized by the use of specific binding properties of a particular antibody to isolate, target, and/or quantify the antigen.

According to at least some embodiments, the present invention provides a method for detecting the polypeptides according to at least some embodiments of the invention in a biological sample, comprising: contacting a biological sample with an antibody specifically recognizing a polypeptide according to at least some embodiments of the present invention and detecting said interaction; wherein the presence of an interaction correlates with the presence of a polypeptide in the biological sample.

According to at least some embodiments, the present invention provides a method for detecting a polynucleotide according to at least some embodiments of the invention in a biological sample, using NAT based assays, comprising: hybridizing the isolated nucleic acid molecules or oligonucleotide fragments of at least about a minimum length to a nucleic acid material of a biological sample and detecting a hybridization complex; wherein the presence of a hybridization complex correlates with the presence of the polynucleotide in the biological sample.

Non-limiting examples of methods or assays are described below.

The present invention in at least some embodiments also relates to kits based upon such diagnostic methods or assays.

Immunoassays

Immunological binding assays include, for example, an enzyme immune assay (EIA) such as enzyme-linked immunosorbent assay (ELISA), a radioimmune assay (RIA), a Western blot assay, or a slot blot assay (see, e.g., U.S. Pat. Nos. 4,366,241; 4,376,110; 4,517,288; and 4,837,168). Generally, a subject or a sample obtained from a subject is contacted with an antibody that specifically binds a polypeptide according to at least some embodiments of the invention, or a fragment thereof. Optionally, the antibody can be fixed to a solid support prior to contacting the antibody with a sample. Examples of solid supports include but are not limited to glass or plastic in the form of, e.g., a microtiter plate, a stick, a bead, or a microbead. After incubating the sample with antibodies, the mixture is washed and the antibody-marker complex formed can be detected. This can be accomplished by incubating the washed mixture with a detection reagent. Alternatively, the marker in the sample can be detected using an indirect assay, wherein, for example, a second, labeled antibody is used to detect bound marker-specific antibody. Throughout the assays, incubation and/or washing steps may be required after each combination of reagents. Incubation steps can vary from about 5 seconds to several hours, preferably from about 5 minutes to about 24 hours. However, the incubation time will depend upon the assay format, marker, volume, concentrations and the like. Usually the assays will be carried out at ambient temperature, although they can be conducted over a range of temperatures, such as 10° C. to 40° C.

The amount of an antibody-marker complex can optionally be determined by comparing to a standard or to a control amount and/or signal.

Radio-immunoassay (RIA): According to one embodiment, this method involves contacting the biological sample with a specific antibody followed by a radiolabeled secondary antibody or antibody binding protein (e.g., protein A labeled with I125) immobilized on a precipitable carrier such as agarose beads. The number of counts in the precipitated pellet is proportional to the amount of the marker polypeptide in the sample.

Enzyme linked immunosorbent assay (ELISA): This method involves fixation of a sample containing the target polypeptide to a surface such as a well of a microtiter plate. A substrate specific antibody coupled to an enzyme is applied and allowed to bind to the target polypeptide. Presence of the antibody is then detected and quantitated by a colorimetric reaction employing the enzyme coupled to the antibody. Enzymes commonly employed in this method include horseradish peroxidase and alkaline phosphatase. The amount of substrate present in the sample is proportional to the amount of color produced. A substrate standard is generally employed to improve quantitative accuracy.

Western blot: This method involves separation of a solution containing the target polypeptide by means of an acrylamide gel followed by transfer of the polypeptides to a membrane (e.g., nylon or PVDF). Presence of the target polypeptide is then detected by specific antibodies, which are in turn detected by antibody binding reagents. Antibody binding reagents may be, for example, protein A, or secondary antibodies. Antibody binding reagents may be radiolabeled or enzyme linked as described hereinabove. Detection may be by autoradiography, colorimetric reaction or chemiluminescence. This method allows both quantitative analysis of the amount of target polypeptide and determination of its identity by a relative position on the membrane which is indicative of a migration distance in the acrylamide gel during electrophoresis.

Immunohistochemical analysis: This method involves detection of a substrate in situ in fixed cells by specific antibodies. The antibodies may be enzyme linked or linked to fluorophores. Detection is by microscopy and subjective evaluation. If enzyme linked antibodies are employed, a colorimetric reaction may be required.

Fluorescence activated cell sorting (FACS): This method involves detection of a target polypeptide in situ in cells by specific antibodies. The antibodies are linked to fluorophores. Detection is by means of a cell sorting machine which reads the wavelength of light emitted from each cell as it passes through a light beam. This method may employ two or more antibodies simultaneously.

Nucleic Acid Technology (Nat) Based Assays:

According to at least some embodiments the invention also contemplates nucleic acids which selectively hybridize with the polynucleotides according to at least some embodiments of the invention. The following are non-limiting examples of Nucleic Acid Technology-based assays: polymerase chain reaction (PCR), Real-Time PCR, ligase chain reaction (LCR), Self-Sustained Synthetic Reaction, Q-Beta Replicase, Cycling probe reaction, Branched DNA, RFLP analysis, DGGE/TGGE, Single-Strand Conformation Polymorphism, Dideoxy fingerprinting, microarrays, Fluorescense In Situ Hybridization and Comparative Genomic Hybridization. Detection of a nucleic acid of interest in a biological sample may be effected by assays which involve nucleic acid amplification technology. Amplification of a target nucleic acid sequence may be carried out by a number of suitable methods known in the art. Non-limiting examples of amplification techniques include primer based-PCR, LCR, strand displacement amplification (SDA), transcription-based amplification, the q3 replicase system and NASBA (Kwoh et al., 1989, Proc. NatI. Acad. Sci. USA 86, 1173-1177; Lizardi et al., 1988, BioTechnology 6:1197-1202; Malek et al., 1994, Methods Mol. Biol., 28:253-260; and Sambrook et al., 1989, supra). As used herein, a "primer" refers to an oligonucleotide which is capable of annealing to (hybridizing with) a target sequence, thereby creating a double stranded region which can serve as an initiation point for DNA synthesis under suitable conditions. The terminology "amplification pair" (or "primer pair") refers herein to a pair of oligonucleotides (oligos), which are selected to be used together in amplifying a selected nucleic acid sequence by one of a number of types of amplification processes, preferably a polymerase chain reaction.

Oligonucleotide primers according to at least some embodiments of the present invention may be of any suitable length, depending on the particular assay format and the particular needs and targeted genomes employed. Optionally, the oligonucleotide primers are at least 12 nucleotides in length, preferably between 15 and 24 nucleotides, and they may be adapted to be especially suited to a chosen nucleic acid amplification system. As commonly known in the art, the oligonucleotide primers can be designed by taking into consideration the melting point of hybridization thereof with its targeted sequence (Sambrook et al., 1989, Molecular Cloning—A Laboratory Manual, 2nd Edition, CSH Laboratories; Ausubel et al., 1989, in Current Protocols in Molecular Biology, John Wiley & Sons Inc., N.Y.).

Radio-Imaging Methods

These methods include but are not limited to, positron emission tomography (PET) and single photon emission computed tomography (SPECT). Both of these techniques are non-invasive, and can be used to detect and/or measure a wide variety of tissue events and/or functions, such as detecting cancerous cells for example. Unlike PET, SPECT can optionally be used with two labels simultaneously. SPECT has some other advantages as well, for example with regard to cost and the types of labels that can be used. For example, U.S. Pat. No. 6,696,686 describes the use of SPECT for detection of breast cancer.

According to at least some embodiments the present invention also relates to kits based upon such diagnostic methods or assays.

Theranostics:

According to at least some embodiments the present invention also relates to the ude of markers and antibodies according to at least some embodiments of the invention for theranostics. The term theranostics describes the use of diagnostic testing to diagnose the disease, choose the correct treatment regime according to the results of diagnostic testing and/or monitor the patient response to therapy according to the results of diagnostic testing. Theranostic tests optionally may be used to select patients for treatments that are particularly likely to benefit them and unlikely to produce side-effects. They can also provide an early and objective indication of treatment efficacy in individual patients, so that (if necessary) the treatment can be altered with a minimum of delay. For example: DAKO and Genentech together created HercepTest and Herceptin (trastuzumab) for the treatment of breast cancer, the first theranostic test approved simultaneously with a new therapeutic drug. In addition to HercepTest (which is an immunohistochemical test), other theranostic tests are in development which use traditional clinical chemistry, immunoassay, cell-based technologies and nucleic acid tests. PPGx's recently launched TPMT (thiopurine S-methyltransferase) test, which is enabling doctors to identify patients at risk for potentially fatal adverse reactions to 6-mercaptopurine, an agent used in the treatment of leukemia. Also, Nova Molecular pioneered SNP genotyping of the apolipoprotein E gene to predict Alzheimer's disease patients' responses to cholinomimetic therapies and it is now widely used in clinical trials of new drugs for this indication. Thus, the field of theranostics represents the intersection of diagnostic testing information that predicts the response of a patient to a treatment with the selection of the appropriate treatment for that particular patient.

Surrogate Markers:

According to at least some embodiments the present invention also relates to the ude of markers and antibodies according to at least some embodiments of the invention as Surrogate markers. A surrogate marker is a marker, that is detectable in a laboratory and/or according to a physical sign or symptom on the patient, and that is used in therapeutic trials as a substitute for a clinically meaningful endpoint. The surrogate marker is a direct measure of how a patient feels, functions, or survives which is expected to predict the effect of the therapy. The need for surrogate markers mainly arises when such markers can be measured earlier, more conveniently, or more frequently than the endpoints of interest in terms of the effect of a treatment on a patient, which are referred to as the clinical endpoints. Ideally, a surrogate marker will be biologically plausible, predictive of disease progression and measurable by standardized assays (including but not limited to traditional clinical chemistry, immunoassay, cell-based technologies, nucleic acid tests and imaging modalities).

Surrogate endpoints were used first mainly in the cardiovascular area. For example, antihypertensive drugs have been approved based on their effectiveness in lowering blood pressure. Similarly, in the past, cholesterol-lowering agents have been approved based on their ability to decrease serum cholesterol, not on the direct evidence that they decrease mortality from atherosclerotic heart disease. The measurement of cholesterol levels is now an accepted surrogate marker of atherosclerosis. In addition, currently two commonly used surrogate markers in HIV studies are CD4+ T cell counts and quantitative plasma HIV RNA (viral load). In some embodiments of this invention, the polypeptide/polynucleotide expression pattern may serve as a surrogate marker for a particular disease, as will be appreciated by one skilled in the art.

Small Interfering Nucleic Acids and Antisense Molecules

According to at least some embodiments the present invention further relates to small interfering nucleic acids, in particular siNA comprising complementary sequences capable of specifically hybridizing with the polynucleotides according to at least some embodiments of the invention and specifically silencing these genes. According to at least some embodiments the present invention also relates to sequences and constructs encoding such nucleic acids and to the uses of such nucleic acids or constructs to modify TMEM154 gene expression, particularly to reduce or inhibit gene expression.

Certain single stranded nucleic acid molecules are able to form a self-complementary double stranded region where part of the nucleotide sequence is able to interact with another part of the sequence by Watson-Crick base pairing between inverted repeats of the sequence. Where the repeated regions are adjacent or in close proximity to each other, the double stranded regions may form structures known as hairpin structures. The hairpin structure forms with an unpaired "loop" of nucleotides at one end of the hairpin structure, with the inverted repeat sequence annealed. The loop may also facilitate the folding of the nucleic acid chain.

Hairpin RNA sequences have been used in interfering RNA and gene silencing technologies. Such techniques are described for example in U.S. Pat. No. 6,573,099 and in Grimm D. (Adv. Drug Deliv. Rev. 2009 61 (9): 672-703). According to at least some embodiments the present invention further contemplates antisense RNA molecules complementary to the polynucleotides according to at least some embodiments of the invention, or to any fragment thereof. Antisense RNA may be introduced into a cell to inhibit translation of the complementary mRNA by hybridizing with the polynucleotides of the according to at least some embodiments of the invention and obstructing the translation machinery.

siNA or antisense molecules according to at least some embodiments of the invention may be used as a therapeutic tool to inhibit TMEM154 gene expression in vivo.

The following examples are offered for illustrative purposes only, and are not intended to limit the scope of the present invention in any way.

All patent and literature references cited in the present specification are hereby incorporated by reference in their entirety.

EXAMPLES

Example 1

Methods Used to Analyze the Expression of the RNA

The targets according to at least some embodiments of the present invention were tested with regard to their expression in various cancerous and non-cancerous tissue samples and/or with regard to its expression in a wide panel of human samples which contains various types of immune cells, and hematological malignancies samples and cell lines, as well as several samples of normal tissues. The list of the blood specific RNA samples used for the qRT-PCR analysis is provided in Table 1 below. A description of the multiple myeloma samples from the blood panel described in Table 1, is provided in Table 1_1. A description of the samples used in the normal tissue panels are provided in Table 2. Tests were then performed as described in the "Materials and Experimental Procedures" section below.

TABLE 1

| Blood panel sample | Description | Organ/Cell type | Tumor Type |
|---|---|---|---|
| 1_PBMC2 | PBMCs | blood-derived cells | |
| 2_PBMC3 | PBMCs | blood-derived cells | |
| 3_Bcell1 | B cells | blood-derived cells | |
| 4_Bcell2 | B cells | blood-derived cells | |
| 5_J_Bcell | B cells | blood-derived cells | |
| 6_K_Bcells_act | Bcells activated | blood-derived cells | |
| 7_Tcell1 | T cells | blood-derived cells | |
| 8_Tcell2 | T cells | blood-derived cells | |
| 9_M_CD8 | CD4+ T cells | blood-derived cells | |
| 10_G_CD4_unt | CD8+ T cells | blood-derived cells | |
| 11_H_CD4_Beads | CD4+ w Activation beads | blood-derived cells | |
| 12_I_CD4_Beads_IL12 | CD4 w act. Beads + IL12 | blood-derived cells | |
| 13_95_CD4+CD25− | CD4+CD25− | blood-derived cells | |
| 15_NK | NK cells | blood-derived cells | |
| 16_CD34+_1548 | CD34+(PCBM1548) | blood-derived cells | |
| 17_CD34+_1028 | CD34+(PCBM1028) | blood-derived cells | |
| 18_PMN | PMNs | blood-derived cells | |
| 19_A_Mono | Monocytes | blood-derived cells | |
| 20_B_Macro_imma | Macrophages immature | blood-derived cells | |
| 21_C_Macro_mat | Macrophages mature | blood-derived cells | |
| 22_D_DCs_immat | DCs immature | blood-derived cells | |
| 23_E_DCs_mat_LPS | DCs mature LPS | blood-derived cells | |
| 24_F_DCs_mat_CK | DCs mature CK | blood-derived cells | |
| 25_L_DCs + T | DCs + T cells | blood-derived cells | |
| 26_Lym1 | 13987A1 | Lymph Node | Lymphoma |
| 27_Lym2 | 43594B1 | Muscle | lymphoma |
| 28_Lym3 | 65493A1 | Testis | Lymphoma |
| 29_MalLym3 | 75894A1 | Brain | Lymphoma |
| 30_NonHod_SCLym | 83325A1 | Lymph Node | NHL Small Cell |
| 31_NonHod_FolLym | 76943A1(5 tubes) | Lymph Node | NHL Follicular |
| 32_Lym_Fol_GI | CN_4_ASRBNA35 | | NHL Follicular Grade I (Small Cell) |
| 33_Lym_Fol_GII | CN_1_113GHA8J | | NHL Follicular Grade II (mixed Small & Large Cell) |
| 34_Lym_Fol_GIII | CN_8_VXML6AXI | | NHL Follicular Grade III (Large Cell) |
| 35_MalLym1 | 76218B1 | Testis | NHL Large Cell |
| 36_MalLym2 | 76102A1 | Lymph Node | NHL Large Cell |
| 37_Lym_DifBCell1 | CN_2_4HDLNA2R | | NHL Diffuse Large B-Cell |
| 38_Lym_DifBCell2 | CN_3_4M4S7AAM | | NHL Diffuse Large B-Cell |
| 39_Lym_DifBCell3 | CN_5_HEODOAR2 | | NHL Diffuse Large B-Cell |
| 40_NonHod_Lym1 | 77332A1(5 tubes) | Colon | NHL Diffuse Large B-Cell |
| 41_MalLym4 | 76161A1 | Spleen | NHL Diffuse Large B-Cell |
| 42_Lym_MantleCell1 | CN_6_MAE47AOY | | NHL Mantle Cell |
| 43_Lym_MantleCell2 | CN_7_VJU9OAO9 | | NHL Mantle Cell |
| 44_NonHod_Lym2 | 95377A1(5 tubes) | Spleen | NHL |
| 45_THP_1 | THP-1 | monocytes | AML cell line |
| 77-MM_Patient1 | multiple myeloma Patient | See Table 1_1 | |
| 78-MM_Patient2 | multiple myeloma Patient | See Table 1_1 | |
| 79-MM_Patient3 | multiple myeloma Patient | See Table 1_1 | |
| 80-MM_Patient4 | multiple myeloma Patient | See Table 1_1 | |
| 81-MM_Patient5 | multiple myeloma Patient | See Table 1_1 | |
| 82-MM_Patient6 | multiple myeloma Patient | See Table 1_1 | |
| 83-MM_Patient7 | multiple myeloma Patient | See Table 1_1 | |
| 84-MM_Tumor1 | multiple myeloma Tumor | See Table 1_1 | |
| 85-MM_Tumor2 | multiple myeloma Tumor | See Table 1_1 | |

TABLE 1-continued

| Blood panel sample | Description | Organ/Cell type | Tumor Type |
|---|---|---|---|
| 87-MM_Tumor4 | multiple myeloma Tumor | See Table 1_1 | |
| 59_NCI_H929 | NCI-H929 | B lymphoblasts | multiple myeloma cell line |
| 60_MC/CAR | MC/CAR | B lymphoblasts | multiple myeloma cell line |
| 61_U266 | U266 | B lymphoblasts | multiple myeloma cell line |
| 62_RPMI8226 | RPMI8226 | B lymphoblasts | multiple myeloma cell line |
| 63_IM_9 | IM-9 | B lymphoblasts | multiple myeloma cell line |
| 64_cereN | cerebellum normal | cerebellum normal | |
| 65_kidneyN1 | kidney normal | kidney normal | |
| 66_kidneyN2 | kidney normal | kidney normal | |
| 67_KidneyN3 | kidney normal | kidney normal | |
| 68_colonN1 | colon normal | colon normal | |
| 69_colonN2 | colon normal | colon normal | |
| 70_stomN | stomach normal | stomach normal | |
| 71_liverN | liver normal | liver normal | |
| 72_lungN1 | lung normal | lung normal | |
| 73_lungN2 | lung normal | lung normal | |
| 74_small intestineN | small intestine | small intestine | |
| 75_brainN | brain normal mix | brain normal mix | |
| 76_heartN | heart normal mix | heart normal mix | |

TABLE 1_1 multiple myeloma samples details

| | patient ID | tumor ID | Diagnosis | Bone disease | Heavy chain isotype | Light chain isotype | ISS | Sex |
|---|---|---|---|---|---|---|---|---|
| 77-MM_Patient1 | 1289 | | Amyloidosis | UD | IgG | kappa | | |
| 78-MM_Patient2 | 1441 | | myeloma | No | IgG | — | satge 2 | |
| 79-MM_Patient3 | 1647 | | myeloma | UD | IgG | kappa | stage 3 | |
| 80-MM_Patient4 | 1434 | | myeloma | UD | IgG | kappa | satge 3 | |
| 81-MM_Patient5 | 1650 | | Undetermained (myeloma vs. MGUS) | UD | IgG | lambda | stage 2 | |
| 82-MM_Patient6 | 1661 | | myeloma | Yes | urine secretor | lambda | stage 1 | |
| 83-MM_Patient7 | 1058 | | myeloma | Yes | IgG | lambda | | |
| 84-MM_Tumor1 | 1016 | LAPCLκ-1 | Plasma cell leukemia | UD | IgG | kappa | | — |
| 85-MM_Tumor2 | 1065 | LAGκ-1A | myeloma | Yes | IgG | kappa | | F |
| 87-MM_Tumor4 | 1178 | LAGκ-2 | myeloma | Yes | IgG | kappa | | M |

TABLE 2

Tissue samples in normal panel:

| sample name | tissue | Source | Sample id |
|---|---|---|---|
| 1-(7)-Bc-Rectum | Rectum | Biochain | A610297 |
| 2-(8)-Bc-Rectum | Rectum | Biochain | A610298 |
| 3-GC-Colon | Colon | GCI | CDSUV |
| 4-As-Colon | Colon | Asterand | 31802 |
| 5-As-Colon | Colon | Asterand | 74446 |
| 6-GC-Small bowel | Small bowel | GCI | V9L7D |
| 7-GC-Small bowel | Small bowel | GCI | M3GVT |
| 8-GC-Small bowel | Small bowel | GCI | 196S2 |
| 9-(9)-Am-Stomach | Stomach | Ambion | 110P04A |
| 11-(11)-Bc-Esoph | Esophagus | Biochain | A603814 |
| 12-(12)-Bc-Esoph | Esophagus | Biochain | A603813 |
| 13-As-Panc | Panc | Asterand | 9442 |
| 14-As-Panc | Panc | Asterand | 11134 |
| 16-As-Liver | Liver | Asterand | 7203 |
| 17-(28)-Am-Bladder | Bladder | Ambion | 071P02C |
| 18-(29)-Bc-Bladder | Bladder | Biochain | A504088 |

TABLE 2-continued

Tissue samples in normal panel:

| sample name | tissue | Source | Sample id |
|---|---|---|---|
| 19-(64)-Am-Kidney | Kidney | Ambion | 111P0101B |
| 20-(65)-Cl-Kidney | Kidney | Clontech | 1110970 |
| 21-(66)-Bc-Kidney | Kidney | Biochain | A411080 |
| 22-GC-Kidney | Kidney | GCI | N1EVZ |
| 23-GC-Kidney | Kidney | GCI | BMI6W |
| 25-(43)-Bc-Adrenal | Adrenal gland | Biochain | A610374 |
| 26-(16)-Am-Lung | Lung | Ambion | 111P0103A |
| 28-As-Lung | Lung | Asterand | 9275 |
| 29-As-Lung | Lung | Asterand | 6161 |
| 30-As-Lung | Lung | Asterand | 7180 |
| 31-(75)-GC-Ovary | Ovary | GCI | L629FRV1 |
| 32-(76)-GC-Ovary | Ovary | GCI | DWHTZRQX |
| 33-(77)-GC-Ovary | Ovary | GCI | FDPL9NJ6 |
| 34-(78)-GC-Ovary | Ovary | GCI | GWXUZN5M |
| 36-GC-cervix | Cervix | GCI | E2P2N |
| 34-(78)-GC-Ovary | Ovary | GCI | GWXUZN5M |
| 36-GC-cervix | Cervix | GCI | E2P2N |
| 38-(26)-Bc-Uterus | Uterus | Biochain | A504090 |
| 39-(30)-Am-Placen | Placenta | Ambion | 021P33A |
| 40-(32)-Bc-Placen | Placenta | Biochain | A411073 |
| 41-GC-Breast | Breast | GCI | DHLR1 |
| 42-GC-Breast | Breast | GCI | TG6J6 |
| 43-GC-Breast | Breast | GCI | E6UDD |
| 44-(38)-Am-Prostate | Prostate | Ambion | 25955 |
| 45-Bc-Prostate | Prostate | Biochain | A609258 |
| 46-As-Testis | Testis | Asterand | 19567 |
| 47-As-Testis | Testis | Asterand | 42120 |
| 49-GC-Artery | Artery | GCI | YGTVY |
| 51-TH-Blood-PBMC | PBMC | Tel-Hashomer | 31055 |
| 52-TH-Blood-PBMC | PBMC | Tel-Hashomer | 31058 |
| 53-(54)-Ic-Spleen | Spleen | Ichilov | CG-267 |
| 56-(58)-Am-Thymus | Thymus | Ambion | 101P0101A |
| 57-(60)-Bc-Thyroid | Thyroid | Biochain | A610287 |
| 58-(62)-Ic-Thyroid | Thyroid | Ichilov | CG-119-2 |
| 59-Gc-Sali gland | Salivary gland | GCI | NNSMV |
| 60-(67)-Ic-Cerebellum | Cerebellum | Ichilov | CG-183-5 |
| 61-(68)-Ic-Cerebellum | Cerebellum | Ichilov | CG-212-5 |
| 62-(69)-Bc-Brain | Brain | Biochain | A411322 |
| 63-(71)-Bc-Brain | Brain | Biochain | A411079 |
| 64-(72)-Ic-Brain | Brain | Ichilov | CG-151-1 |
| 65-(44)-Bc-Heart | Heart | Biochain | A411077 |
| 66-(46)-Ic-Heart | Heart | Ichilov | CG-227-1 |
| 67-(45)-Ic-Heart (Fibrotic) | Heart | Ichilov | CG-255-9 |
| 71-As-Skel Mus | Skeletal muscle | Asterand | 8244 |
| 72-As-Skel Mus | Skeletal muscle | Asterand | 12648 |
| 73-As-Skel Mus | Skeletal muscle | Asterand | 6166 |

Materials and Experimental Procedures Used to Obtain Expression Data

RNA Preparation—

RNA was obtained from ABS (Wilmington, Del. 19801, USA, http://www.absbioreagents.com), BioChain Inst. Inc. (Hayward, Calif. 94545 USA www.biochain.com), GOG for ovary samples—Pediatic Cooperative Human Tissue Network, Gynecologic Oncology Group Tissue Bank, Children Hospital of Columbus (Columbus Ohio 43205 USA), Clontech (Franklin Lakes, N.J. USA 07417, www.clontech.com), Ambion (Austin, Tex. 78744 USA, http://www.ambion.com), Asternad (Detroit, Mich. 48202-3420, USA, www.asterand.com), AllCells, LLC. (Emeryville, Calif. 94608 USA, www,allcells,co,), IMBCR—Institute for Myeloma and Bone cancer research (West Hollywood, Calif. 90069, USA, www.imbcr.org) and from Genomics Collaborative Inc. a Division of Seracare (Cambridge, Mass. 02139, USA, www.genomicsinc.com). Alternatively, RNA was generated from blood cells, cell lines or tissue samples using TRI-Reagent (Molecular Research Center), according to Manufacturer's instructions. Tissue and RNA samples were obtained from patients or from postmortem. Most total RNA samples were treated with DNaseI (Ambion).

RT PCR—Purified RNA (2-10 μg) was mixed with 300-1500 ng Random Hexamer primers (Invitrogen) and 500 μM dNTP in a total volume of 31.2 to 156 μl. The mixture was incubated for 5 min at 65° C. and then quickly chilled on ice. Thereafter, 10-50 μl of 5× SuperscriptII first strand buffer (Invitrogen), 4.8 to 24 μl 0.1M DTT and 80-400 units RNasin (Promega) were added, and the mixture was incubated for 10 min at 25° C., followed by further incubation at 42° C. for 2 min. Then, 2-10 μl (400-2000 units) of SuperscriptII (Invitrogen) was added and the reaction (final volume of 50-250 μl) was incubated for 50 min at 42° C. and then inactivated at 70° C. for 15 min. The resulting cDNA was diluted 1:20 in TE buffer (10 mM Tris pH=8, 1 mM EDTA pH=8).

Real-Time RT-PCR analysis carried out as described below—cDNA (5 μl), prepared as described above, was used as a template in Real-Time PCR reactions (final volume of 20 μl) using the SYBR Green I assay (PE Applied Biosystem) with specific primers and UNG Enzyme (Eurogentech or ABI or Roche). The amplification was effected as follows: 50° C. for 2 min, 95° C. for 10 min, and then 40 cycles of 95° C. for 15 sec, followed by 60° C. for 1 min, following by dissociation step. Detection was performed by using the PE Applied Biosystem SDS 7000. The cycle in which the reactions achieved a threshold level of fluorescence (Ct=Threshold Cycle, described in detail below) was registered and was used to calculate the relative transcript quantity in the RT reactions. The relative quantity was calculated using the equation Q=efficiency^−Ct. The efficiency of the PCR reaction was calculated from a standard curve, created by using different dilutions of several reverse transcription (RT) reactions. To minimize inherent differences in the RT reaction, the resulting relative quantities were normalized using a normalization factor calculated in the following way:

The expression of several housekeeping (HSKP) genes was checked on every panel. The relative quantity (Q) of each housekeeping gene in each sample, calculated as described above, was divided by the median quantity of this gene in all panel samples to obtain the "relative Q rel to MED". Then, for each sample the median of the "relative Q rel to MED" of the selected housekeeping genes was calculated and served as normalization factor of this sample for further calculations. It should be noted that this type of analysis provides relative quantification.

For each RT sample, the expression of the specific amplicon was normalized to the normalization factor calculated from the expression of different house keeping genes as described in section above.

These house keeping genes are different for each panel.

The sequences of the housekeeping genes measured in all the examples on normal tissue samples panel were as follows:

SDHA (GenBank Accession No. NM_004168 (SEQ ID NO:45); amplicon-SDHA-amplicon (SEQ ID NO:32)), Forward primer (SEQ ID NO:30), SDHA Reverse primer (SEQ ID NO:31).

Ubiquitin (GenBank Accession No. BC000449 (SEQ ID NO:48); amplicon-Ubiquitin-amplicon (SEQ ID NO: 29)), Ubiquitn Forward primer (SEQ ID NO:27), Ubiquitin Reverse primer (SEQ ID NO:28).

TATA box (GenBank Accession No. NM_003194 (SEQ ID NO:49); TATA amplicon (SEQ ID NO: 26)), TATA box Forward primer (SEQ ID NO:24), TATA box Reverse primer (SEQ ID NO:25).

The sequences of the housekeeping genes measured in all the examples of blood panel were as follows:

HSB1L_HUMAN (Accession No. Q9Y450 (SEQ ID NO:50)), T05337_seg30-34F1—Forward primer (SEQ ID NO:15), T05337_seg30-34R1 Reverse primer (SEQ ID NO:16), T05337_seg30-34Amplicon (SEQ ID NO:17).

DHSA_HUMAN (Accession No P31040 (SEQ ID NO:51)), M78124_seg45-48F1 Forward primer (SEQ ID NO:18), M78124_seg45-48R1—Reverse primer (SEQ ID NO:19), M78124_seg45-48Amplicon (SEQ ID NO:20).

SLC25A3 (Accession No Q7Z7N7 (SEQ ID NO:53)), SSMPCPseg24-25-29F1—Forward primer (SEQ ID NO:21), SSMPCPseg24-25-29R1—Reverse primer (SEQ ID NO:22), SSMPCPseg24-25-29Amplicon (SEQ ID NO:23).

SFRS4_HUMSRP75A (Accession NO Q08170 (SEQ ID NO:52)), HUMSRP75Aseg30-33F1 Forward primer (SEQ ID NO:12), HUMSRP75Aseg30-33R1 Reverse primer (SEQ ID NO:13), HUMSRP75Aseg30-33Amplicon (SEQ ID NO:14).

TBP—TATA Box binding protein (Accession NO P20226 (SEQ ID NO:54)), HSTFIIDXseg7-9F1—forward primer (SEQ ID NO:42), HSTFIIDXseg7-9R1—reverse primer (SEQ ID NO:43), HSTFIIDXseg7-9 Amplicon (SEQ ID NO:44).

Example 2

Description for Cluster W38346

Cluster W38346, corresponding to variants of the known hypothetical protein LOC201799 (SEQ ID NO:5) (SwissProt accession identifier NP_689893; synonims: TMEM154). features 4 transcripts and proteins of interest, the names for which are given in Table 3.

TABLE 3

| Proteins of interest | |
|---|---|
| Protein Name | Corresponding Transcript(s) |
| W38346_P3 (SEQ ID NO: 5) | W38346_T0 (SEQ ID NO: 1); W38346_T1 (SEQ ID NO: 2) |
| W38346_P4 (SEQ ID NO: 8) | W38346_T2 (SEQ ID NO: 3) |
| W38346_P7 (SEQ ID NO: 9) | W38346_T5 (SEQ ID NO: 4) |

TMEM154 (transmembrane protein 154) was identified in 2 full length cDNA projects (Strausberg et al. 2002, PNAS 99(26): 16899-903; Ota et al. 2004, Nat Genet 36(1): 40-5). However no research was published about TMEM154 specifically.

TMEM154 proteins and discrete portions thereof were originally disclosed in PCT Application No. WO 2010/067308, owned in common with the present application and having at least one inventor in common with the present application, which is hereby incorporated by reference as if fully set forth herein.

The background art does not teach or suggest the efficacy of any protein and/or antibody and/or polynucleotide and/or conjugate and/or fragment in combination with another treatment, such as another drug, particularly for a synergistic effect.

In particular this invention uses TMEM154 antigen and discrete portions thereof as a drug target for therapeutic small molecules, peptides, antibodies, antisense RNAs, siRNAs, ribozymes, and the like. More particularly the invention relates to diagnostic and therapeutic polyclonal and monoclonal antibodies and fragments thereof that bind TMEM154, and portions and variants thereof. According to at least some embodiments of the invention there is a use antibodies and antibody fragments against TMEM154 antigen, its secreted or soluble form or ECD and/or variants, conjugates, or fragments thereof and fragments and variants thereof for treating and diagnosing multiple myeloma, aggressive and/or drug resistant and/or refractory multiple myeloma, wherein this antigen is differentially expressed.

Example 2_1

Expression Analysis of TMEM154 Transcripts

Expression of TMEM154 W38346 Transcripts which are Detectable by Amplicon as Depicted in Sequence Name W38346_seg6-20F1R1 (SEQ ID NO:41) in Different Normal Tissues and Blood Specific Panel Expression of TMEM154 transcripts detectable by or according to seg6-20F1R1-W38346_seg6-20F1R1 (SEQ ID NO:41) amplicon and primers W38346_seg6-20F (SEQ ID NO: 39) and W38346_seg6-20R (SEQ ID NO: 40) was measured by real time PCR in blood panel and normal panel. The samples used for blood panel are detailed in Tables 2 and 2_1. The samples used for normal panel are detailed in Table 2.

Normal Panel—

Figures 1, 9A:
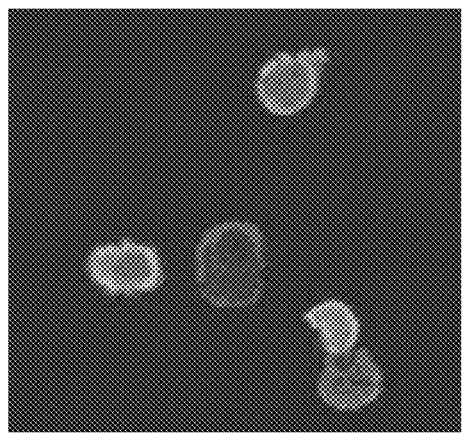

For each RT sample, the expression of the above amplicon was normalized to the normalization factor calculated from the expression of several house keeping genes as described in example 1. The normalized quantity of each RT sample was then divided by the median of the quantities of the kidney samples (sample numbers 19-23, Table 2 above), to obtain a value of relative expression of each sample relative to median of the kidney samples, as shown in FIG. 1. High expression was observed in normal PBMCs, spleen and esophagus.

For blood panel—For each RT sample, the expression of the above amplicon was normalized to the normalization factor calculated from the expression of several house keeping genes as described in example 1. The normalized quantity of each RT sample was then divided by the median of the quantities of the kidney normal samples (sample numbers 65-67, Table 1 above), to obtain a value of relative expression of each sample relative to median of the kidney normal samples.

Figures 2, 9A:
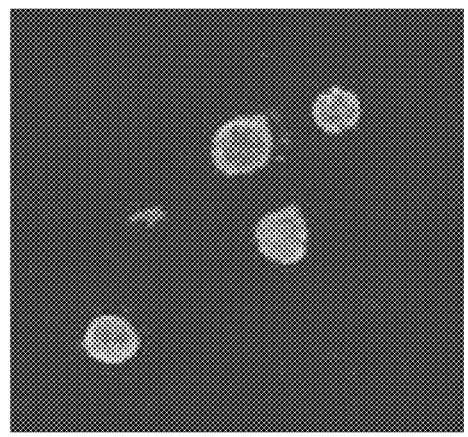

The results of this analysis are depicted in the histogram in FIG. 2. Expression of the above-indicated TMEM154 transcripts is high in PMN, monocytes, multiple myeloma patients and several lymphomas samples.

```
Forward Primer (W38346_seg6-20F) (SEQ ID NO: 39):
CCTTCTAGCCAAGGATCTCAGAGTG

Reverse Primer (W38346_seg6-20R) (SEQ ID NO: 40):
CTTGGGTTGTGATTTGATTCCTTCTC

Amplicon (W38346_seg6-20F1R1 (SEQ ID NO: 41)):
CCTTCTAGCCAAGGATCTCAGAGTGCTTTACAGACATATGAACTGGGAA

GTGAAAACGTGAAAGTCCCTATTTTTGAGGAAGATACACCCTCTGTTAT

GGAAATTGAAATGGAAGAGCTTGATAAATGGATGAACAGCATGAATAGA

AATGCCGACTTTGAATGTTTACCTACCTTGAAGGAAGAGAAGGAATCAA

ATCACAACCCAAG
```

Example 2_2

Cloning of TMEM154_T0P3 ORF Fused to Flag Tag

Cloning of TMEM154_T0_P3 open reading frame (ORF) fused to FLAG was carried out by RT PCR as described below.

RT18 PMNs (RT-PCR product resulted from sample 18, Table 1) and RT19 monocytes (RT-PCR product resulted from sample 19, Table 1) from the blood panel were diluted 1:20 in TE buffer (10 mM Tris, 1 mM EDTA pH 8) and served as a template for PCR.

PCR was done using GoTaq ReadyMix (Promega, catalog number M122) under the following conditions: 10 μl—cDNA described above; 1.5 μl—H2O; and 0.5 μl (10 μM)—of each primer #100-952 (SEQ ID NO:58) and #100-953 (SEQ ID NO:59) in a total reaction volume of 25 μl; with a reaction program of 2 minutes in 94° C.; 35 cycles of: 30 seconds at 94° C., 30 seconds at 55° C., 1 minute at 72° C.; then 10 minutes at 72° C. Primers which were used include gene specific sequences; restriction enzyme sites; Kozak sequence and FLAG tag.

5 μl of PCR product were loaded onto a 1.2% agarose gel stained with ethidium bromide, electrophoresed in 1×TAE solution at 100V, and visualized with UV light. After verification of expected band size, PCR product was purified using QiaQuick™ PCR Purification kit (Qiagen, catalog number: 28004). The purified PCR product was digested with NheI and AgeI restriction enzymes (New England Biolabs, Beverly, Mass., U.S.A.). After digestion, DNA was loaded onto a 1.2% agarose gel as described above. The expected band size was excised and extracted from the gel using QiaQuick™ Gel Extraction kit (Qiagen, catalog number: 28707). The digested DNA was then ligated into pIRESpuro3 vector, previously digested with the above restriction enzymes, using LigaFast™ Rapid DNA Ligation System (Promega, catalog number: M8221). The resulting DNA was transformed into competent E. Coli bacteria DH5α (RBC Bioscience, Taipei, Taiwan, catalog number: RH816) according to manufacturer's instructions, then plated on LB-ampicillin agar plates for selection of recombinant plasmids, and incubated overnight at 37° C. The following day, positive colonies were screened by PCR using pIRESpuro3 vector specific primer and gene specific primer (data not shown). The PCR product was analyzed using 1.2% agarose gel as described above. After verification of expected band size, positive colonies were grown in 5 ml Terrific Broth supplemented with 100 μg/ml ampicillin, with shaking overnight at 37° C. Plasmid DNA was isolated from bacterial cultures using Qiaprep™ Spin Miniprep Kit (Qiagen, catalog number: 27106). Accurate cloning was verified by sequencing the inserts (Weizmann Institute, Rehovot, Israel). Upon verification of an error-free colony (i.e. no mutations within the ORF), recombinant plasmids were processed for further analyses.

Figures 3, 9A:
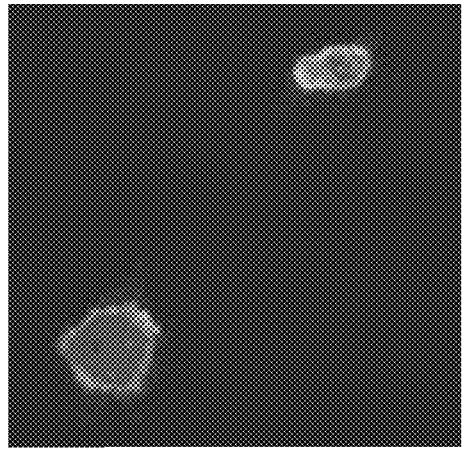
FIG. 3 presents the DNA sequence of the TMEM154_T0_FLAG (SEQ ID NO:60); FLAG sequence is in underlined.
FIGS. 9A-9C present specific cell staining localized to the cell membrane, observed using purified TM21 and TM101 antibodies on three different cell lines.

The DNA sequence of the resulting TMEM154_T0_FLAG (SEQ ID NO:60) is shown in FIG. 3; FLAG sequence is in underlined.

Figures 4, 9A:
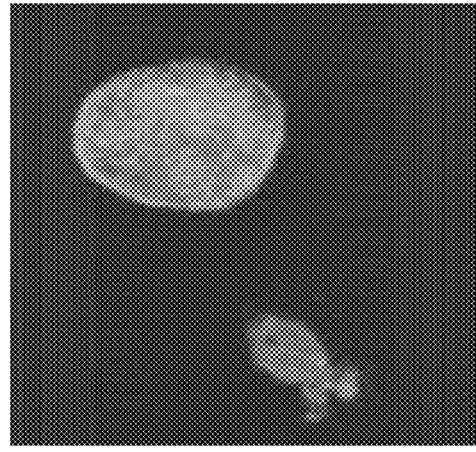
FIG. 4 presents the amino acid sequence of TMEM154_P3_FLAG (SEQ ID NO:61); FLAG sequence is in underlined.
Figures 1, 9B:
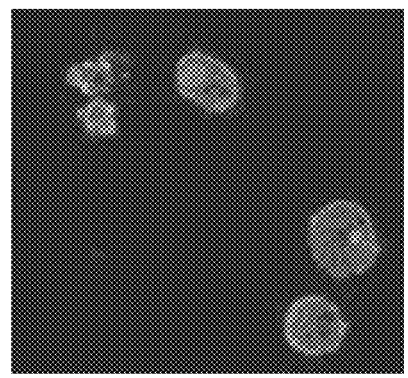
Figures 2, 9B:
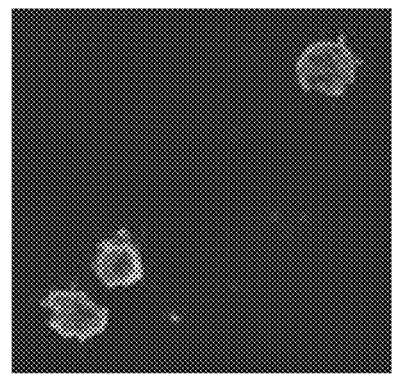
Figures 3, 9B:
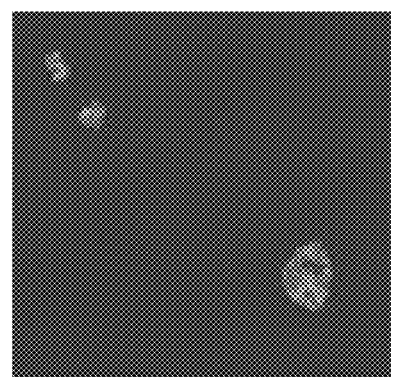
Figures 1, 9C:
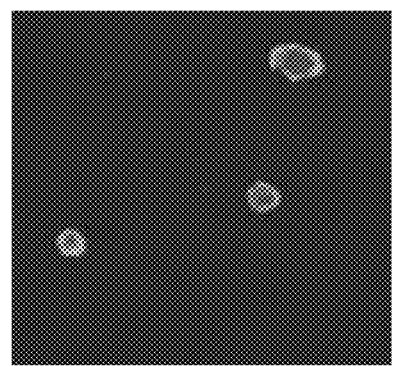
Figures 2, 9C:
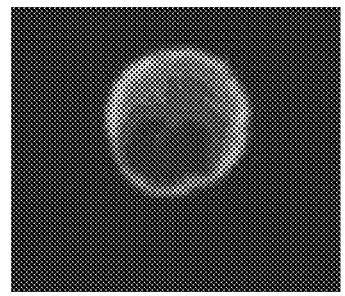
Figures 3, 9C:
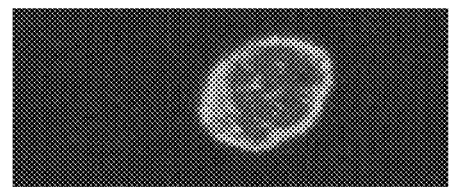

The amino acid sequence of TMEM154_P3_FLAG (SEQ ID NO:61) is shown in FIG. 4; FLAG sequence is in underlined.

Example 2_3

Determining Cell Localization of TMEM154_P3

In order to determine TMEM154_P3 cellular localization, TMEM154_T0_P3 was cloned in frame to FLAG tag, as described above. Protein localization was observed upon transient transfection (Chen et al., Molecular Vision 2002; 8; 372-388) using confocal microscopy. 48 hours following transfection, the cells were stained with anti FLAG antibodies conjugated to Cy-3 fluorophore and were observed for the presence of fluorescent signal.

TMEM154_T0_P3_FLAG (SEQ ID NO:60) pIRESpuro3 construct was transiently transfected into HEK-293T cells as described above. 48 hours post transient transfection, cells on coverslip were further processed for immunostaining and analysis by confocal microscopy. The cover slip was washed in phosphate buffered saline (PBS), then fixed for 15 minutes with a solution of 3.7% paraformaldehyde (PFA) (Sigma, catalog number: P-6148)/3% glucose (Sigma, catalog number: G5767) (diluted in PBS). Quenching of PFA was done by a 5 minute incubation in 3 mM glycine (Sigma, catalog number: G7126) (diluted in PBS). After two 5-minute washes in PBS, cells were permeabilized with 0.1% triton-X100 (diluted in PBS) for 5 minutes. After two 5-minute washes in PBS, blocking of non-specific regions was done with 5% bovine serum albumin (BSA) (Sigma, catalog number: A4503) (diluted in PBS) for 20 minutes. The coverslip was then incubated, in a humid chamber for 1 hour, with mouse anti FLAG-Cy3 antibodies (Sigma, catalog number: A9594), diluted 1:100 in 5% BSA in PBS, followed by three 5-minute washes in PBS. The coverslip was then mounted on a slide with Gel Mount Aqueous medium (Sigma, catalog number:

G0918) and cells were observed for the presence of fluorescent product using confocal microscopy.

Figure 5A:
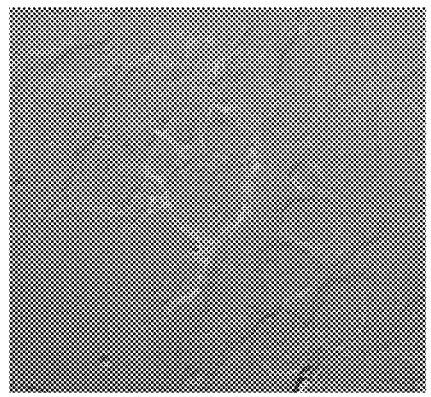
FIGS. 5A and 5B present the localization results for TMEM154_P3.
Figure 5B:
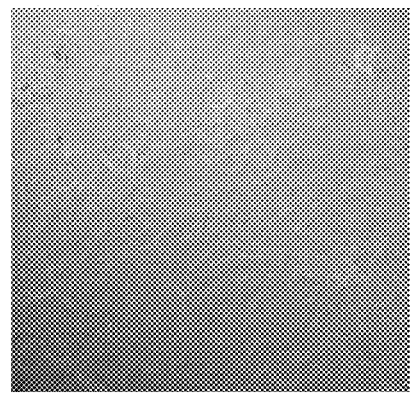

Cell localization is shown in FIG. 5. TMEM154_P3 is localized to the cell membrane.

Example 2_4

Production of Polyclonal Antibodies Specific to TMEM154_P3 Protein

All polyclonal Abs production procedure, including peptides synthesis, peptides conjugation, animal immunizations, bleeding and antibodies purification were performed at Sigma-Aldrich (Israel). Two pairs of rabbits (one pair per epitope) were injected to prepare antibodies for TMEM154_P3 (rabbit numbers 6285 and 6286, 6248 and 6249 respectively). All animal care, handling and injections were performed by Sigma (Israel).

Peptides which were used for rabbit immunization were as follows: RGNYEELENSGDTTVESER designated TM21 (SEQ ID NO:62) a sequence taken from the N' terminus corresponding to amino acids 21-39 of TMEM154_P3 protein (SEQ ID NO:5). The second peptide sequence to be used was: YKRKRTKQEPSSQGSQS designated TM101 (SEQ ID NO:63), a sequence taken from the C' terminus, corresponding to amino acids 101-117 of TMEM154_P3 protein (SEQ ID NO:5). 25 mg of each peptide were synthesized with 95% purity of which 10 mg were conjugated to KLH carrier. Each pair of rabbits was immunized with the corresponding conjugated peptide as follows: rabbits 6285 and 6286 were immunized with TM21 peptide (SEQ ID NO:62), and rabbits 6248 and 6249 were immunized with TM101 peptide (SEQ ID NO:63). Animals were immunized every two weeks. 60 ml production bleeds from each rabbit were collected and affinity purification was performed with the peptide against which the respective antibodies were raised.

Example 2_5

Characterization of Purified TMEM154_P3 Antibodies by Immunostaining of TMEM154 Transfected Cells In order to further characterize the affinity purified antibodies raised against TMEM154_P3, antibody-protein interaction was studied using immunostaining of TMEM154_P3 stable transfected HEK293T cells.

Generation of Stable Pool Expressing TMEM154_P3 Protein:

Two stably transfected pool were generated, TMEM154_P3 pIRESpuro3 and the negative control empty pIRESpuro3. Both constructs were transfected into HEK-293T cells as previously described.

Immunostaining of TMEM154 Transfected Cells 500,000 cells per well of HEK-293T (ATCC, CRL-11268) stably expressing TMEM154 or the empty vector pIRES puro3, described above, were plated on sterile glass coverslips, 13 mm diameter (Marienfeld, catalog number: 01 115 30), which were placed in a 6 well plate, using 2 ml prewarmed DMEM [Dulbecco's modified Eagle's Media, Biological Industries (Beit Ha'Emek, Israel), catalog number: 01-055-1A]+10% FBS [Fetal Bovine Serum, Biological Industries (Beit Ha'Emek, Israel), catalog number: 04-001-1A]+4 mM L-Glutamine [Biological Industries (Beit Ha'Emek, Israel), catalog number: 03-020-1A].

48 hours post plating the cells on coverslips they were further processed for immunostaining and analysis by confocal microscopy. The cover slips were washed in phosphate buffered saline (PBS), then fixed for 25 minutes with a 3.7% paraformaldehyde (PFA) (Sigma, catalog number: P-6148)/3% glucose (Sigma, catalog number: G5767). After 2 5-minute washes in PBS, cells were permeabilized with 0.1% triton-X100 (diluted in PBS) for 5 minutes. After two 5-minute washes in PBS, blocking of non-specific regions was done with 5% bovine serum albumin (BSA) (Sigma, catalog number: A4503) (diluted in PBS) for 20 minutes. The coverslips were then incubated, in a humid chamber for 1 hour, with purified rabbit anti-TMEM154 antibodies described above: TM21 (Rabbit 6285, 6286 1 mg/ml) was diluted 1:1000 in 5% BSA in PBS and TM101 (Rabbit 6248 6249, 1 mg/ml) was diluted 1:1000 in 5% BSA. The antibodies were washed 3 times for 5-minutes in PBS. The coverslips were then incubated, in a humid chamber for 1 hour, with secondary antibody: donkey anti-rabbit conjugated to Cy-3 fluorophore (Jackson ImmunoResearch, catalog number: 711-165-152), diluted 1:200 in 3% BSA in PBS. After 3 5-minute washes in PBS, the fixed coverslips were mounted on slides with Gel Mount Aqueous medium (Sigma, catalog number: G0918) and cells were observed for the presence of fluorescent product using confocal microscopy.

Figure 6A:
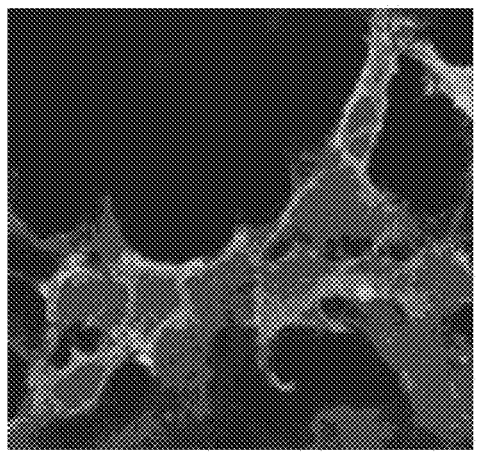
FIGS. 6A and 6B present the specific cell staining localized to the cell membrane, observed using purified TM21 antibodies on TMEM154 transfected cells.
Figure 6B:
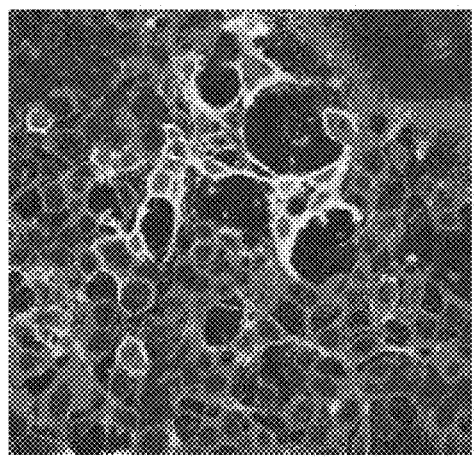
Figure 7A:
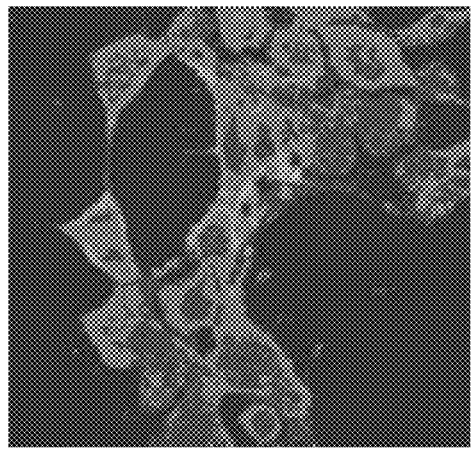
FIGS. 7A and 7B present the specific cell staining localized to the cell membrane, observed using purified TM101 antibodies on TMEM154 transfected cells.
Figure 7B:
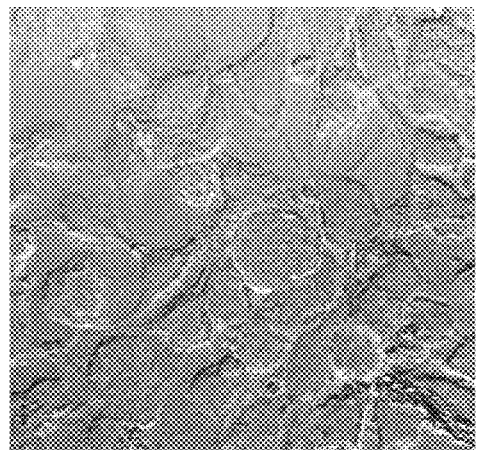
Figure 8A:
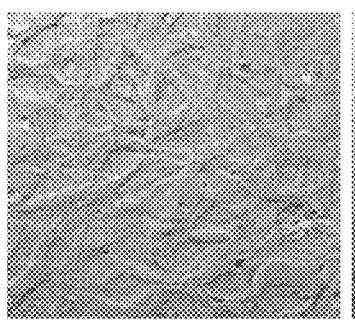
FIGS. 8A-8C present results of cell staining, observed using purified TM21 and TM101 antibodies on the negative control pIRESpuro3 HEK-293T transfected cells.
Figure 8B:
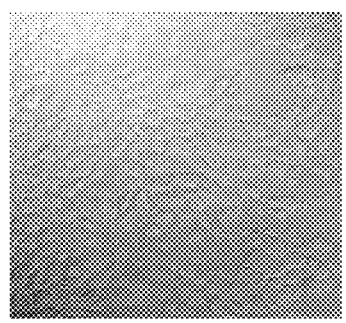
Figure 8C:
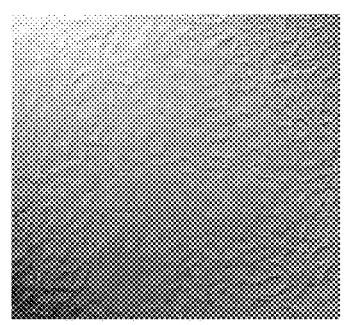

Specific cell staining localized to the cell membrane was observed using purified TM21 and TM101 antibodies on TMEM154 transfected cells (FIG. 6 and FIG. 7 respectively), while, no staining was observed using these antibodies on the negative control pIRESpuro3 HEK-293T transfected cells (FIG. 8). The red fluorescence obtained in FIGS. 6 and 7 as opposed to the absence of signal in FIG. 8 demonstrates the specificity of TM21 and TM101 antibodies to TMEM154_P3 (SEQ ID NO:5).

Example 2_6

Demonstration of Endogenous Expression of TMEM154_P3 by Immunostaining of Lymphoblast Cell Lines In order to determine endogenous expression of TMEM154, three cell lines were selected for immustaining using specific antibodies against TMEM154_P3 protein described above.

500000 cells from each cell line: Ramos (ATCC cat no CRL-1923), CESS (ATCC cat no TIB-190), Daudi (ATCC cat no CCL-213) were fixed with 3.7% PFA containing 3% Glucose and plated on coverslips previously treated with poly-L-Lysin 0.01% (Sigma cat no P4832). Cells were further processed for immunostaining as describe above and analyzed by confocal microscopy.

Specific cell staining localized to the cell membrane was observed using purified TM21 and TM101 antibodies on all three cell lines as shown in FIG. 9.

Example 3

Expression of TMEM154 on Both CD138 Positive and on CD138 Negative Multiple Myeloma Cells In order to evaluate if TMEM154 is expressed in fresh bone marrow (BM) aspirates derived from MM patients using flow cytometric analysis and immunohistochemical staining with the anti-TMEM154 TM21 polyclonal antibody, as described in M&M sections 1 and 2 below. For this assay MM1s (Exp Hematol. 2003 April; 31(4):271-82.) were used.

Figure 10:
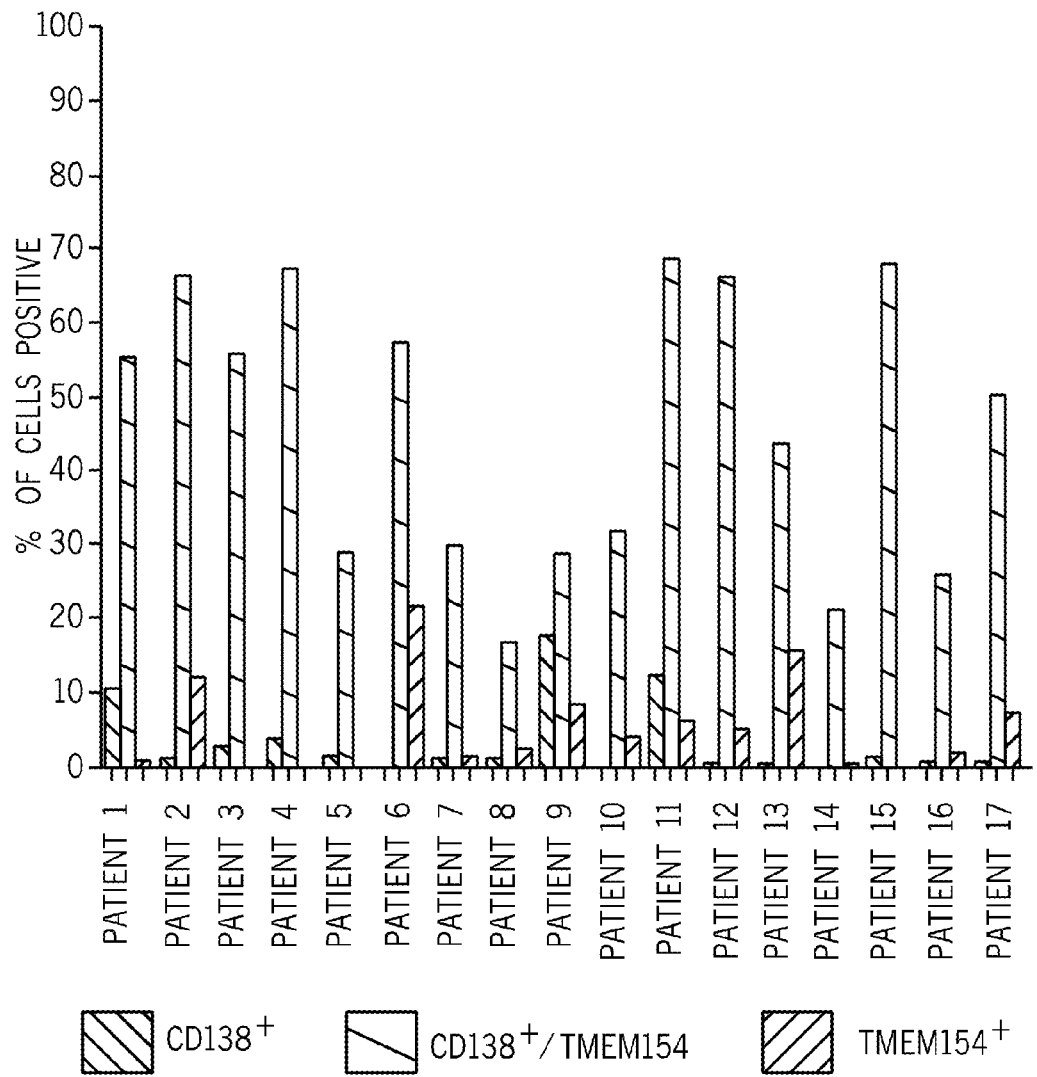
FIG. 10 presents FACS analysis of 17 MM bone marrow patients.

TMEM154 was shown to be highly expressed in MM cell line MM1s cells using TM21 antibody. Next, TMEM154 antigen expression was examined in fresh tumor cells from BM aspirates from 17 MM patients. The results, presented in FIG. 10, show high expression of TMEM154. Notably, as shown in FIG. 10, TMEM154 expression was not only found on CD138+ MM cells but also on MM tumor cells lacking CD138 expression. FIG. 10 presents FACS analysis of 17 MM bone marrow patients, the majority of the cells are positive for both CD138 and TMEM154 (black column), however there is a substantial population ranging from 5 to 30% of CD138 negative cells that are positive to TMEM154.

Table 10 represents the actual FACS cell count of TMEM154 abd CD138 against the disease stage of the patients. Greyed cells represent samples in which the TMEM154 population is larger then the CD138 only positive population.

These results demonstrates the superiority of TMEM154 in both identification/diagnosis and potential treatment using targeted therapy directed at TMEM154, as it can cover a broader range of malignant cells.

Example 4

Figure 11:
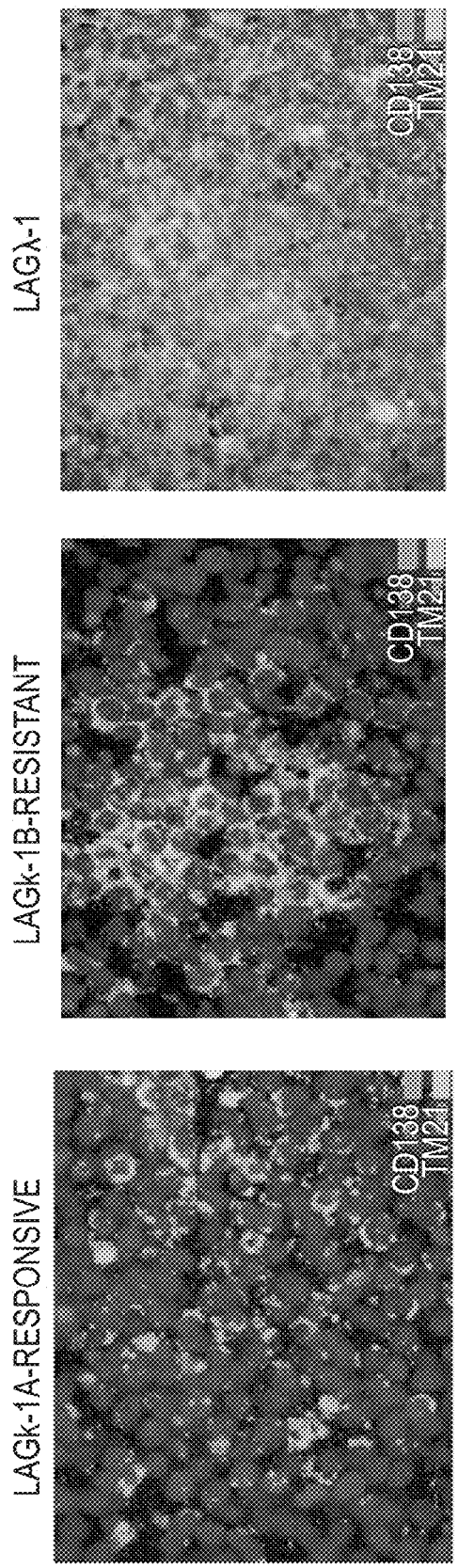
FIG. 11 presents LAGκ-1A, LAGκ-1B and LAGλ-1 cells staining with TM21 pAb as well as anti-CD138 mAb. TMEM154 is shown in light gray; CD138 is shown in dark gray.

TMEM154 Expression in Both Sensitive and Resistant Multiple Myeloma Primary Cells Examination of the expression of TMEM154 antigen using human MM xenograft models LAGκ-1A (bortezomib sensitive), LAGκ-1B (bortezomib resistant) and LAGλ-1 (melphalan resistant) was carried out as described in M&M section 6 below. The bortezomib-sensitive MM tumor LAGκ-1A expresses CD138 whereas the bortezomib-resistant tumor LAGκ-1B developed from the same patient does not express CD138. Cells from all three tumor types were positive for staining with the TM21 antibody. Similar to the fresh MM BM samples, TMEM154 expression was not only found on CD138+ MM cells but also on CD138-tumor cells derived from human MM xenografts primary cell lines (FIG. 11). FIG. 11 presents LAGκ-1A, LAGκ-1B and LAGλ-1 cells staining with TM21 pAb as well as anti-CD138 mAb. TMEM154 is shown in light gray; CD138 is shown in dark gray. Both LAGκ-1A and LAGλ-1 primary cell lines were positive to both CD138 and TMEM154, while the most resistant cell line LAGκ-1B was positive only to TMEM154. These results indicate that the boarder population of tumor

TABLE 10

| Patient ID | Double (%) | CD138 Only (%) | TM21 Only (%) | Stage | Bone damage | M-protein | Diagnosis |
|---|---|---|---|---|---|---|---|
| 1123 | 21.2 | 0 | 0 | I | No | 0.45 g/dl | Waldenstrom's |
| 1419 | 28.9 | 1.3 | 0 | I | No | 0.58 g/dl | Myeloma |
| 1088 | 55.3 | 2.6 | 0 | I | Yes | 1.63 g/dl | Myeloma |
| 1234 | 67.6 | 1 | 0 | I | Yes | 2.46 g/dl | Myeloma |
| 1397 | 66.9 | 3.5 | 0.2 | I | No | 5.27 g/dl | Myeloma |
| 1702 | 31.5 | 0 | 3.9 | I | No | 0.51 g/dl | Myeloma |
| 1723 | 29.7 | 1.4 | 1 | I | Yes | 0 g/dl | Myeloma |
| 1060 | 68.4 | 12 | 6 | IA | No | 0 g/dl | Myeloma |
| 1655 | 16.6 | 1.4 | 2.5 | II | Yes | 0.41 g.dk | Myeloma |
| 1008 | 55.2 | 10.5 | 0.7 | II | Yes | 2.16 g/dl | Myeloma |
| 1022 | 28.4 | 17.5 | 8.3 | II | Yes | 3.42 g/dl | Myeloma |
| 1030 | 25.5 | 0.5 | 1.7 | II | No | 0 g/dl | Myeloma |
| 1434 | 57.1 | 0 | 21.4 | III | No | 4.72 g/dl | Myeloma |
| 1179 | 43.3 | 0.4 | 15.4 | III | No | 5.41 g/dl | Myeloma |
| 1080 | 50 | 0.7 | 7 | III | Yes | 6.15 g/dl | Myeloma |
| 1050 | 66.1 | 1.1 | 11.9 | IIIA | Yes | 0.51 g/dl | Myeloma |
| 1701 | 65.8 | 0.3 | 4.9 | IIIB | Yes | 7.77 g/dl | Myeloma | cells identified by TMEM154 may be also the more aggressive cell population, for which currently no treatment is available Therefore specific targeting of TMEM154 (i.e. using a mAb), may confer a therapeutic solution for border and resistant patient population, for which no current remedy is available.

Example 5

Figure 12A:
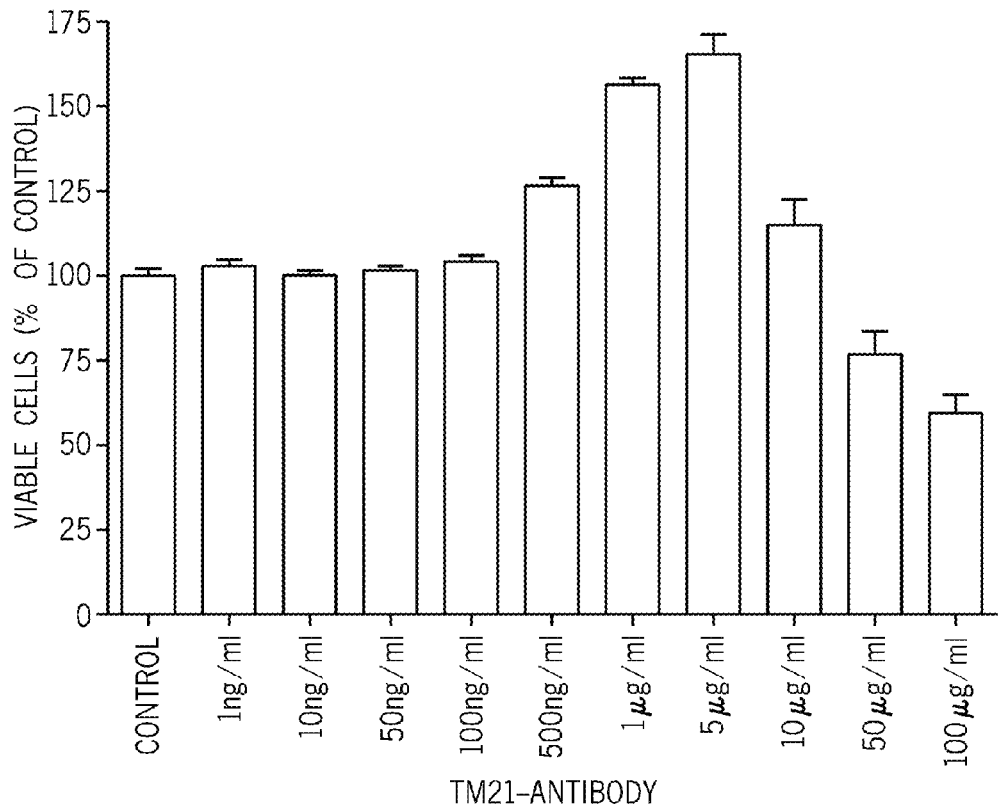
FIG. 12A demonstrates a dose response effect in viability assay (MTS) 48 h post incubation of the MM1s cell line with the TM21 antibody at growing concentration.
Figure 12B:
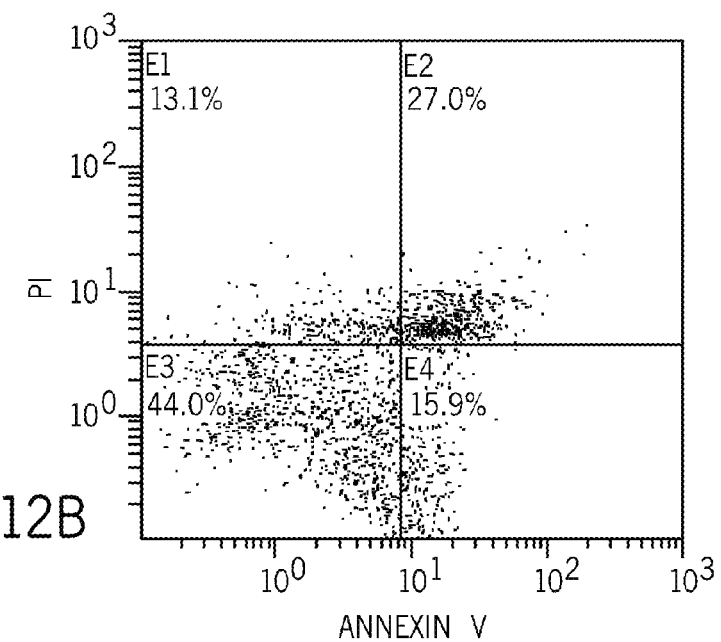
FIG. 12B presents a marked apoptosis detected at the 100 μg dose.

Anti Proliferative Effects of Direct Targeting of TMEM154 Alone or in Synergism with 4 Standard of Care Drugs Examination of the effect of TM21 antibody alone and in combination with dexamethasone (dexamethasone sodium phosphate, American Regent, INC Shirley, N.Y. 11967), melphalan (SIGMA Cat#M-2011), doxorubicin (Doxorubicin hydrochloride, SIGMA, BioChemika 44583 3050 spruce street. St. Louis, M063103) and bortezomib (Velcade, Millennium Pharmaceuticals, Inc Cambridge, Mass. 02139) in vitro was carried out using cell proliferation MTT assays (for protocols used see M&M sections 3 and 4). FIG. 12A demonstrates a dose response effect in viability assay (MTS) 48 h post incubation of the MM1s cell line with the TM21 antibody at growing concentration. FIG. 12B presents a marked apoptosis detected at the 100 μg dose. As shown in FIGS. 12A-12B, Anti-TM21 polyclonal antibody (100 μg/ml) decreased MM tumor cell proliferation and increased apoptosis in the MM cell lines MM1s, RPMI8226 and U266 (data shown for the MM1s cell line, FIGS. 12A-12B. Data not shown for RPMI8226 and U266).

Figure 13A:
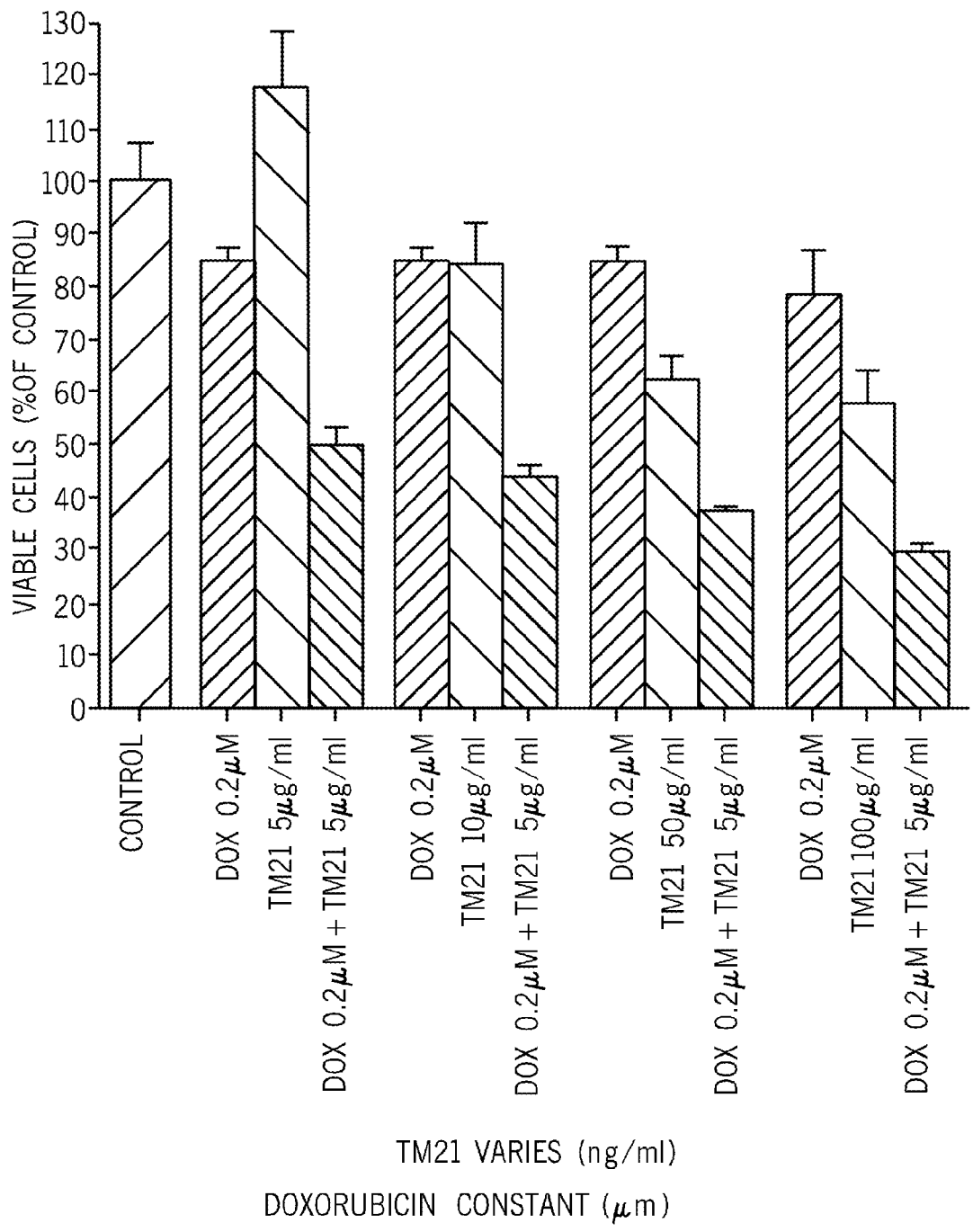
FIG. 13 presents cell viability assay (MTS) using a combination of TM21 with doxorubicin (FIG. 13A), bortezomib (FIG. 13B), dexamethasone (FIG. 13C) and melphalan (FIG. 13D).
Figure 13B:
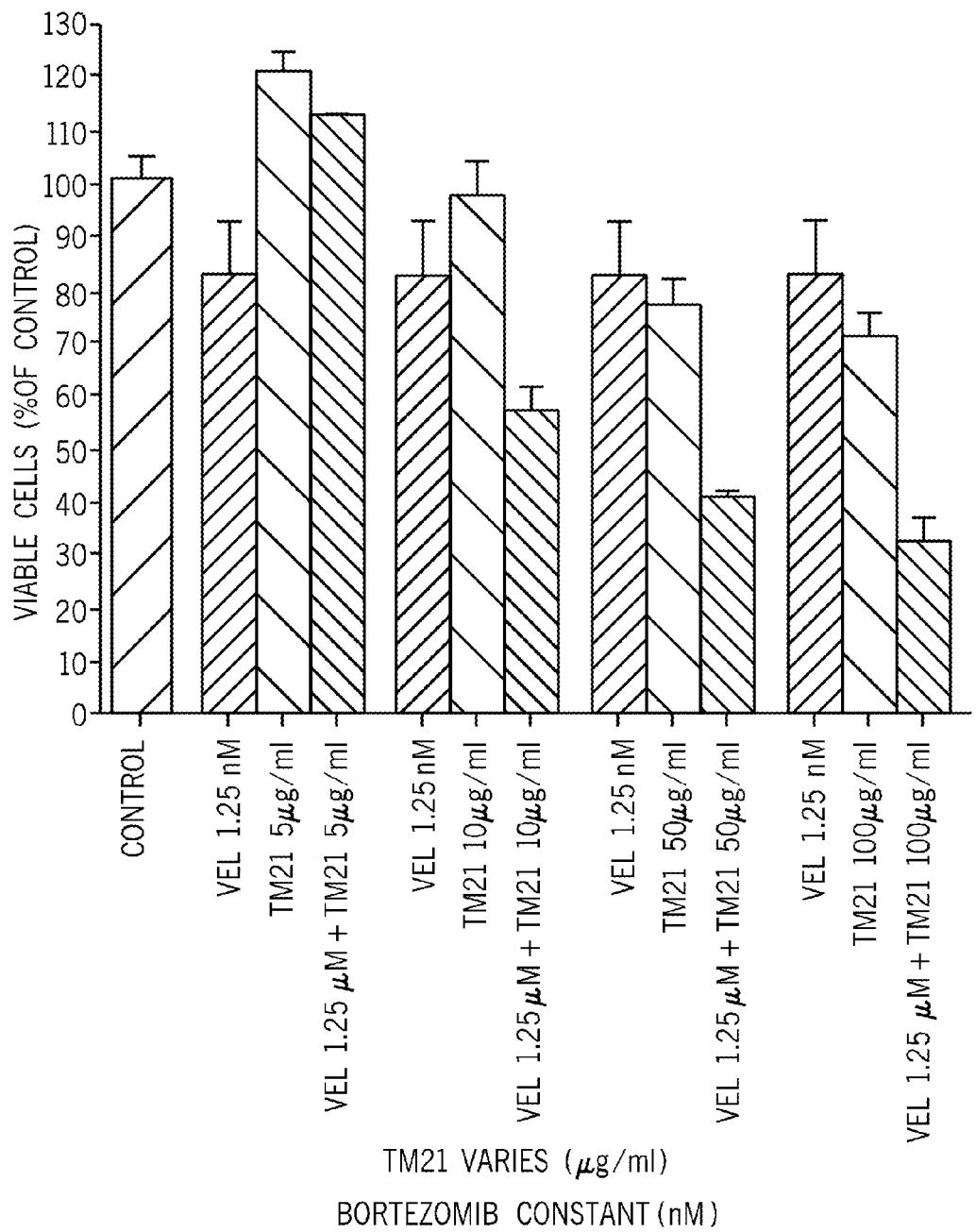
Figure 13C:
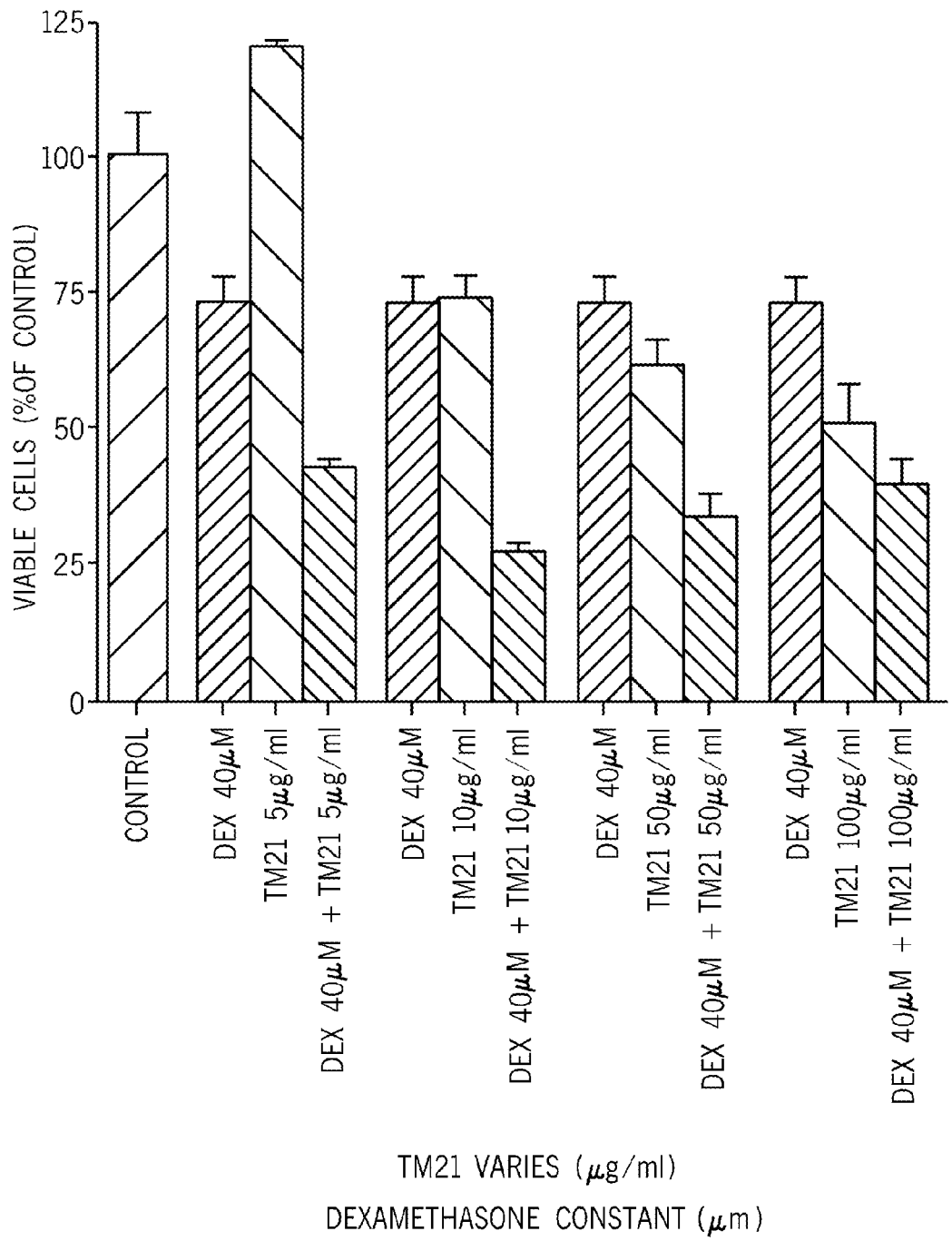
Figure 13D:
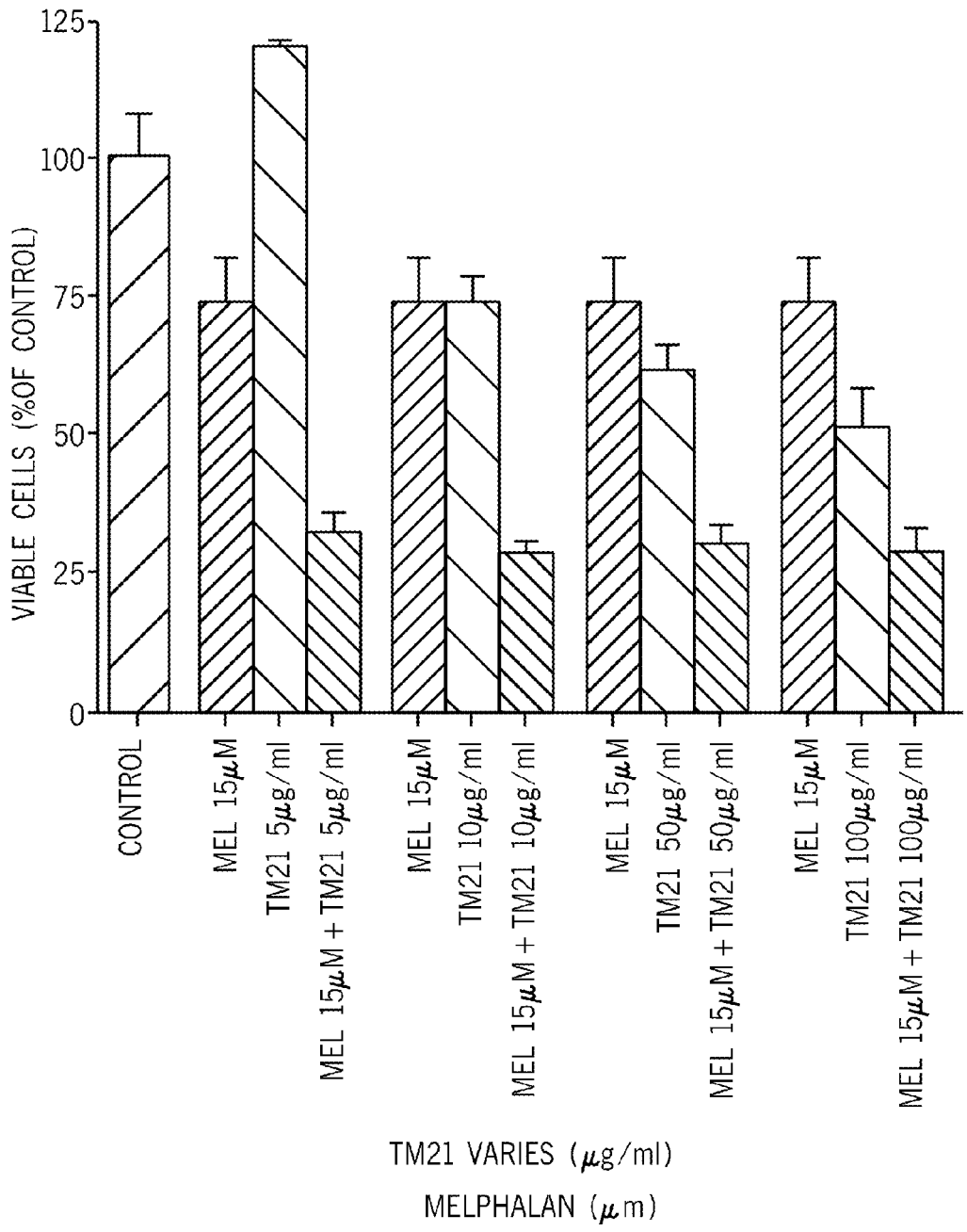

Determination of the effects of combining TM21 antibody with other drugs known for treatment of MM, such as bortezomib, melphalan, doxorubicin or dexamethasone, was demonstrated on the MM1s cell line (for protocol used see M&M section 6 below). FIG. 13 presents cell viability assay (MTS) using a combination of TM21 with doxorubicin (FIG. 13A), bortezomib (FIG. 13B), dexamethasone (FIG. 13C) and melphalan (FIG. 13D). The 4 drugs were held at a constant concentration of IC20-30, while TM21 was used in growing concentrations. A marked synergistic effect was observed in all combinations. As shown in FIGS. 13A-13D, cell proliferation assays demonstrated marked enhanced anti-proliferative effects when TMEM154 antibody at concentrations ranging of 5, 10, 50, and 100 μg/ml was combined with bortezomib, melphalan, doxorubicin or dexamethasone. The data supports the combinations of TEME154 targeted therapy with standard of care protocols in multiple myeloma treatment such as UMYBORTEZ protocol which includes dexamethasone and bortezomib; or the UMYMPBOR protocol which includes Melphalan, Prednisone (a less potent glucocorticoid then dexamethasone) and Weekly Bortezomib; or the MYMP protocol which includes Melphalan and Prednisone. (http://www.bccancer.bc.ca/HPI/Chemotherapgrotocols/Lymphoma/default.htm)

In cases of advanced multiple myeloma the protocol of Bortezomib, Doxorubicin and Dexamethasone (Annals of Oncology. 2008; 19(6):1160-1165.) can be the basis for the combination.

Moreover as synergistic effects were demonstrated, in all standard of care protocols in multiple myeloma treatment the chemotherapy dosage could be lowered, once combined with TMEM154 targeted therapy, in order to avoid side effects of resulting from the toxic effects of the drugs.

Figure 14:
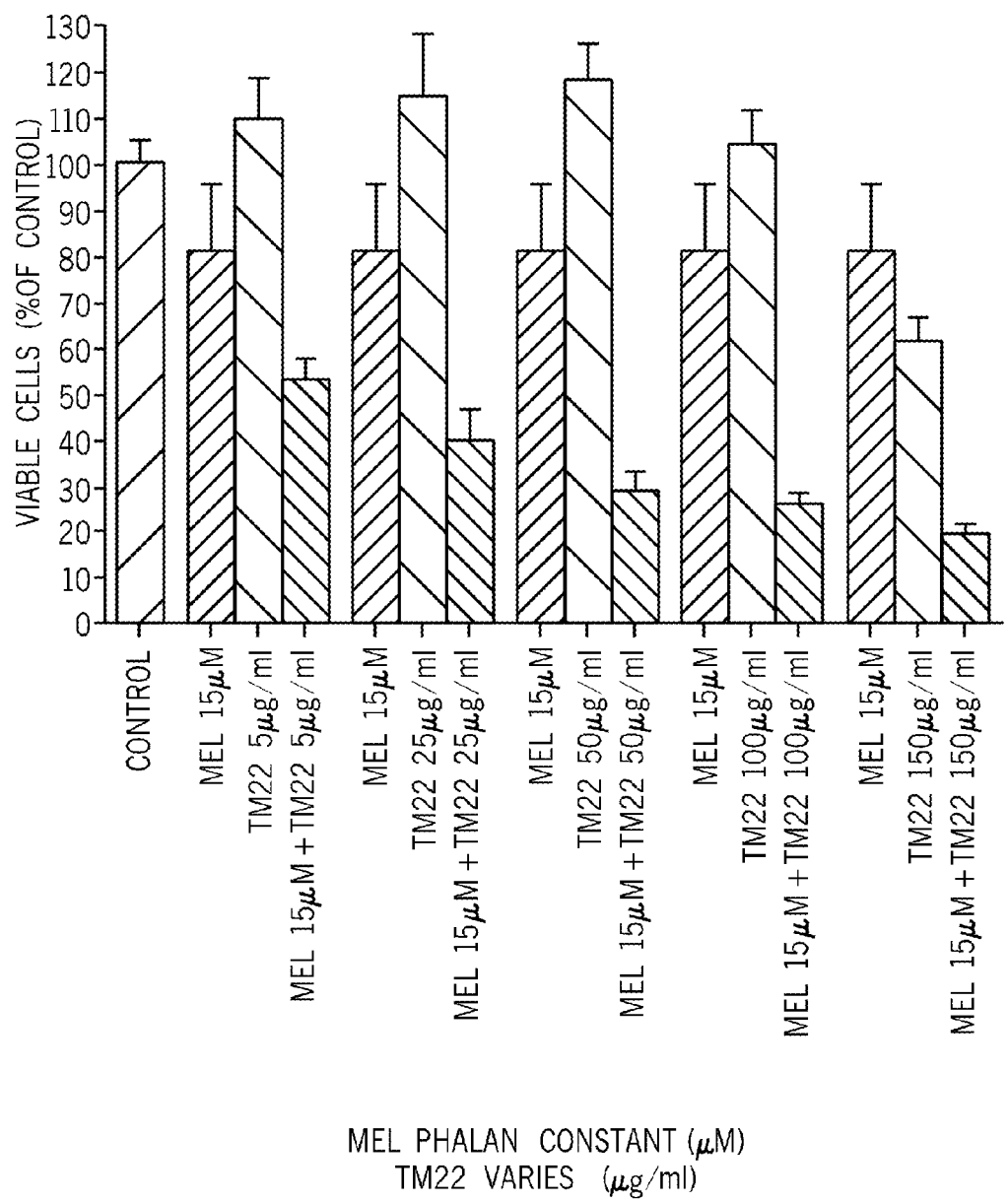
FIG. 14—presents cell viability assay (MTS) using a combination of TM22 pAb with melphalan on a fresh bone aspirate from a multiple myeloma patient.

These results were recapitulated for a combination of TM22 antibody and melphalan in fresh bone marrow derived multiple myeloma samples (FIG. 14).

Material and Methods for Examples 3-5:
Preparation of MM Patient's Bone Marrow Mononuclear Cells (BMMCs)

MM BM cells were isolated using density-gradient centrifugation using Histopaque-1077 (Sigma, St Louis).
Quantification of TM21-Expressing MM Cells Using Flow Cytometric Analysis To measure the TM21 antibody positive cells in MM tumor cells, BM MM cells from 15 MM patients (tumor cells >85%) were double stained with TM21 antibody and anti-CD138 antibody (PE anti-human CD138, Cat#550805, BD Pharmingen) and analyzed using flow cytometric analysis. At least three independent experiments were carried out for each sample.
Determination of Anti-Proliferative Effects of TM21 Antibody on MM Cells In Vitro Using the MTS Assay MM cell lines (n=3) were maintained in RPMI 1640 medium supplemented with 10% fetal bovine serum, 2 mmol/l L-Glutamine, 100 IU/ml penicillin, 100 ug/ml streptomycin, and essential amino acids in an atmosphere of 5% carbon dioxide at 37° C. Cells were plated in 96 well plates at a concentration of $6\times10^4$ cells/100 ul in each well. Cells were incubated for 24 hours prior to drug treatment, after which time the drugs were added in replicates of six for 48 hours. After the 48 hour drug incubation, cell viability was assessed utilizing an MTS assay. The MTS assay also known as the CellTiter 96® AQueous Non-Radioactive Cell Proliferation Assay (a) is a homogeneous, colorimetric method for determining the number of viable cells in proliferation, cytotoxicity or chemosensitivity assays. Fifteen ul of the MTS reagent were added to each well and allowed to incubate for 1-2 hours. The 96 well plate was analyzed in a 96 well-plate reader, and the absorbance of each well was recorded at 490 nM. In this manner, each well recording was quantified into a numeric value, which can be normalized to the control (non-treatment) cells.
Determination of Apoptotic Effects of the TM21 Antibody on MM Cells In Vitro Using the Annexin V Assay The effects of the TM21 antibody on apoptosis in MM cells was assessed using the Annexin V assay. The anti-MM effects observed in the MTS assay could result from decreased cell proliferation due to cell cycle arrest or increased cell death. Since MTS assay measures the integrated consequence of cell cycle arrest and cell death, the apoptotic effects of this antibody on cell lines (n=3) was further determined using this assay. Briefly, MM cells ($5\times10^5$/ml) were treated with TM21 for 24 hrs. After being washed with PBS containing 1% FBS, cells were stained with 0.5 μl FITC-conjugated Annexin V (Biovision, Mountain View, Calif.) in 300 μl Annexin V binding buffer (Biovision, Mountain View, Calif.) for 5 minutes at room temperature. Cell death was determined using flow cytometric analysis with a Cytomics FC500 and software CXP (Beckman Coulter, Miami, Fla.).
Determination of TM21 Expression in Human MM Xenograft Models Five micron sections were cut after fixation of three tumors from three of our SCID-hu MM models (LAGκ-1A, LAGκ-1B and LAGλ-1 cells) in 4% paraformaldehyde. The slides were blocked with 0.05% Tween-20 (TBST) and 3% BSA for 1 hour at room temperature (RT). The samples were exposed to the following antibodies: TM21 antibody, and anti-CD138, Slides were washed three times with TB ST and treated with ARH-conjugated with either anti-mouse, anti-rabbit or anti-goat antibodies (KPL, Gaithersburg, Md.) diluted 1:500 in TBST at RT for 2 hours. The slides were washed three times in TBST, placed in 3-amino-9-ethylcarbazole (AEC) buffer for 5 minutes and color was detected using an AEC kit (Vector, Burlingame, Calif.). For IFA, the slides were blocked with 0.05% Tween-20 (TBST) and 3% BSA for 1 hour at RT and were incubated with anti-mouse IgG conjugated to phycoerythrin (PE) (1:100; BD Biosciences, San Jose, Calif.) at 4° C. overnight. The slides were washed three times with PBS for 15 minutes at RT and incubated with FITC-conjugated swine anti-goat or anti-mouse antibody (Biosource, Camarillo, Calif.) for 2 hours at RT. Anti-DAPI antibody was added to slides as a nuclear marker. The slides were washed as before and mount with aqueous mounting media (Biomeda, Foster City, Calif.). The positive cells were identified under the microscope (Olympus BX51, San Diego, Calif.) and merged cells were analyzed by Microsuite Biological Suite program (Olympus BX51, San Diego, Calif.) or scanned using a Zeiss LSM 510 META confocal microscope (Carl Zeiss Microimaging Inc., Thornwood, N.Y.).

Cell Proliferation Combination Experiment (MTS Assay)

MM tumors MM1s cell line, was maintained in RPMI 1640 medium supplemented with 10% fetal bovine serum, 2 mmol/l L-Glutamine, 100 IU/ml penicillin, 100 ug/ml streptomycin, and essential amino acids in an atmosphere of 5% carbon dioxide at 37° C. Cells were plated in 96 well plates at a concentration of 6×10^4 cells/100 ul in each well. Cells were incubated for 24 hours prior to drug treatment, after which time the drugs were added in replicates of six for 48 hours. After the 48 hour drug incubation, cell viability was assessed utilizing an MTS assay. The MTS assay also known as the CellTiter 96® AQueous Non-Radioactive Cell Proliferation Assay (a) is a homogeneous, colorimetric method for determining the number of viable cells in proliferation, cytotoxicity or chemosensitivity assays. 15 ul of the MTS reagent was added to each well and allowed to incubate for 1-2 hours. The 96 well plates were analyzed in a 96 well-plate reader, recording the absorbance of each well at 490 nM. In this manner each well recording was quantified into a numeric value, which can be normalized to the control (non-treatment) cells Combination Drugs Doxorubicin, Bortezomib (Velcade), Melphalan, Dexamethasone Experiment Group Total combination group: 4 hold the concentration of doxorubicin ($IC_{20-30}$) constant and vary the TM21 (4 different concentrations)

hold the concentration of bortezomib ($IC_{20-30}$) constant and vary the TM21 (4 different concentrations)

hold the concentration of melphalan ($IC_{20-30}$) constant and vary the TM21 (4 different concentrations)

hold the concentration of dexamethasone ($IC_{20-30}$) constant and vary the TM21 (4 different concentrations).

Example 6

Determination of the Mechanism of Anti-Myeloma Effect of TMEM154

Figure 15:
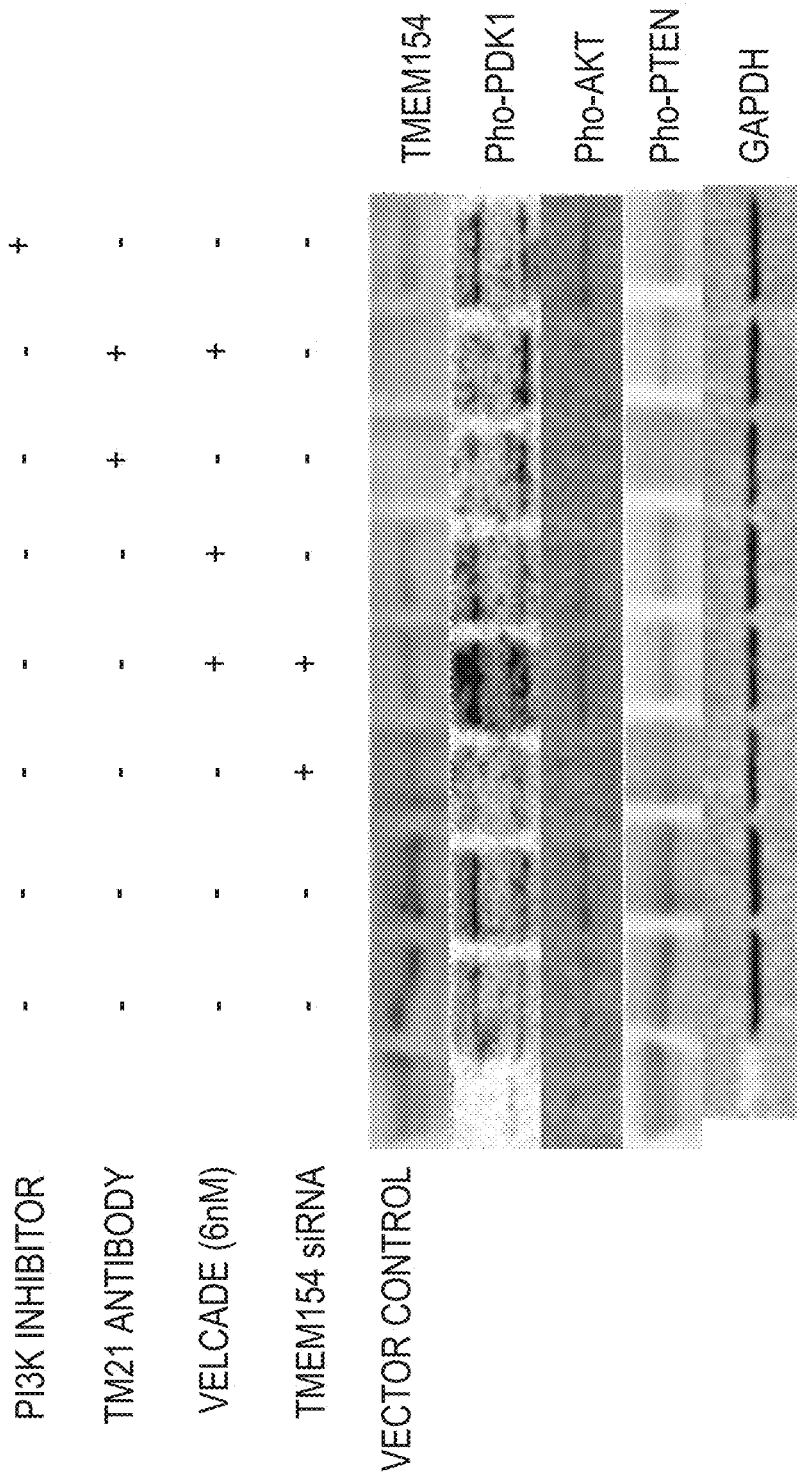
FIG. 15 presents the efficacy of TMEM154 shRNA on the MM 1s cell line, using western blot analysis. The figure also presents the protein levels of phosphorylated PDK1, AKT and PTEN following TMEM154 silencing or treatment with the TM21 antibody.

In this experiment the AKT-related upstream and downstream signaling pathways were examined when TMEM154 expression is silenced with TMEM154 siRNA or the anti-TMEM154 antibody. AKT, also known as PKB, plays a major role in regulating cell survival and apoptosis. This protein kinase is stimulated by insulin and various growth and survival factors to function in a wortmannin-sensitive pathway involving P13 kinase (Burgering, B. M. and Coffer, P. J. Nature 376, 599-602, 1995). AKT is activated by phospholipid binding and activation loop phosphorylation at Thr308 by PDK1 and by phosphorylation within the carboxy terminus at Ser473. The previously elusive PDK2 responsible for phosphorylation of AKT at Ser473 has been identified as mammalian target of rapamycin (mTOR) in a rapamycin-insensitive complex with rictor and Sin1 (Jacinto, E. et al Cell 81, 125-37, 2006). By inhibiting apoptosis, AKT promotes cell survival via phosphorylation and inactivation of several targets, including Bad, forkhead transcription factors, c-Raf, and caspase-9. PTEN phosphatase is a major negative regulator of the PI3 kinase/Akt signaling pathway. LY294002 is a specific PI3 kinase inhibitor. Another essential Akt function is the regulation of glycogen synthesis through phosphorylation and inactivation of GSK-3α and β. Akt may also play a role in insulin stimulation of glucose transport. As demonstrated in FIG. 15, siRNA silencing of TMEM154 resulted in a substantial reduction in TMEM154 protein level, and treatment with the antibody resulted in complete abolishment of TMEM154 protein expression. Of the tested phosphorylated proteins AKT, PDK1 and PTEN were effected by TMEM154 siRNA or antibody treatment, with reduction in phosphorylation levels in all 3 proteins indicating a positive role for TEMEM154 in eliciting survival signals in MM cells.

Material and Methods for Examples 6:

Cells: MM1s myeloma cell line and Fresh MM bone marrow tumor cells were used.

TMEM154 shRNA (Santa Cruz Biotechnology; Cat. No.: sc-88911-V)

Antibodies:

Anti-TMEM154 antibody developed as described herein

Anti-Ohospho-AKT (ser473) (Cell Signaling; Cat. No.: 4060L)

Anti-Ohospho-AKT (Thr308) (Cell Signaling; Cat. No.: 2965L)

Anti-AKT (pan) (Cell Signaling; Cat. No.: 4691L)

Anti-phospho-c-Raf (Ser259) (Cell Signaling; Cat. No.: 94215)

Anti-phospho-GSK3β (Ser9) (Santa Cruz Biotechnology; Cat No.: sc-11757)

Anti-phospho-PTEN (Ser380) (Santa Cruz Biotechnology; Cat No.: sc-31714)

Anti-phospho-PDK1 (Ser241) (Cell Signaling; Cat No.: 3438S)

PI3 kinase inhibitor: Ly294002 (Sigma; Cat No.:L9908)

Transfection of TMEM154 siRNA into tumor cells was carried out as follows: the cultured cells were washed twice with 2 ml shRNA Transfection Medium (SantaCruz catalog number sc-36868). After the medium was aspirated, 800 ul shRNA Plasmid Transfection Medium (SantaCruz catalog number sc-36868) were added to each transfection. Then 200 ul shRNA Plasmid DNA/shRNA Plasmid transfection Reagent Complex (Santa Cruz Biotechnology; Cat No.: sc-108080) was be added to the mixture. It was incubated for 5-7 hours at 37° C. in a CO2 incubator. Following the incubation, 1 ml of normal growth medium (including 2 times the normal serum and antibiotic concentration) were added to the mixture. The cells were incubated for another 18-24 hours under conditions normally used to culture the cells. Following 48 hours post-transfection, the medium were aspirated and fresh medium containing puromycin at the appropriate concentration were added to the cells. The same procedure of aspiration and medium replacement was carried out every 2-3 days.

Western blot analysis to assess protein phosphorylation in MM tumor cells treated or non treated with TMEM154 siRNA as well as Anti-TMEM154 antibody Expression of AKT and phosphor-AKT and related signaling phosphor-proteins was determined in tumor cells treated with TMEM154 siRNA. To determine protein expression, whole tumor cell lysate were prepared. Twenty μg of protein lysates from lysate were electrophoresed on a 4-15% SDS-polyacrylamide gel, 100 V for 3 hours at 4° C. and then proteins were transferred to polyvinylidene difluoride membranes (Bio-Rad, Hercules, Calif.) overnight at 50 mA, 4° C. The membranes were incubated with 5% BSA in overnight at 4° C. Protein expression was visualized using an enhanced chemilluminescence detection system (Amersham, Buckinghamshire, UK) and quantified using a TBST for 1 hour at RT. The primary antibodies (see above) or anti-GAPDH antibodies were added, incubated and analyzed Vesa-Doc gel documentation system (Bio-Rad, Hercules, Calif.).

Example 7

TMEM154 Internalization

Figure 16:
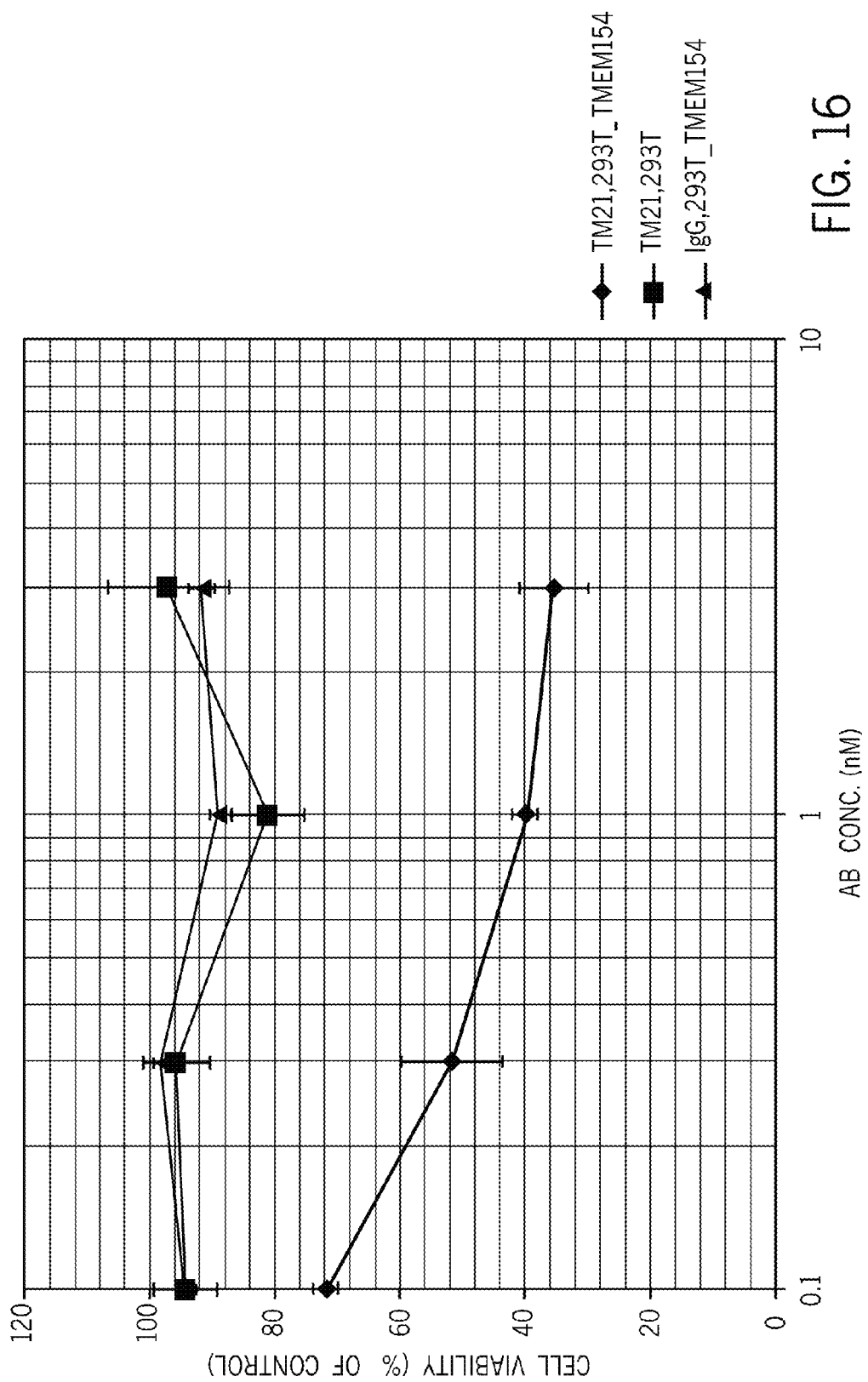
FIG. 16 presents TMEM154 internalization, using the Rab-Zap-based assay on ectopically-expressed TMEM154 in recombinant HEK293T cells upon treatment with the TMEM154 pAb, TM21.

Using the Rab-Zap-based cytotoxicity internalization assay, the internalization of ectopically-expressed TMEM154 was determined in recombinant HEK293T cells upon treatment with the TMEM154 pAb, TM21. As a readout, cell proliferation assay (MTS) was used. An IgG pAb and TM21 on HEK293 (not expressing TMEM154) were used as internal control. The data is presented as % of untreated cells for each cell type (FIG. 16). TM21 pAb induced inhibition in cell proliferation in a dose-dependent manner. A reduction of 65% to 30% in cell proliferation was observed, indicating internalization effect of TM21 upon binding to TMEM154.
Material and Methods for Examples 7:

Recombinant and empty vector transfected HEK293T cells were plated in 96-well plates, 3000 cells per well in 100 μl complete medium, supplemented with Puromycin dihydrochloride (Sigma-Aldrich, P8833, 5 μg/ml) and Penicillin (100 μg/ml)-Streptomycin (100 U/ml) (Biological Industries, 03-031-1B), unless otherwise indicated. The plates were incubated at 37° C., humidifying 5% $CO_2$ incubator.

On day 2, the tested antibodies were pre-incubated with or without Rab-Zap (Saporin conjugate affinity purified goat anti-rabbit IgG polyclonal antibody, Advanced Targeting Systems, cat#IT-05, Lot #69-30; 1.12 mg/ml), at the indicated concentrations in complete medium for 1 hour at RT. 25 μl of each antibody mix were added to each well. Each experiment was performed in triplicates. The plates were incubated for 72 hours at 37° C., humidifying 5% $CO_2$ incubator.

On day 5, 72 hours after applying the antibody mix on the cells, cytotoxicity assay was performed using CellTiter 96® Aqueous Non-Radioactive Cell Proliferation Assay (Promega, G5421). 25 μl of combined MTS+PMS reagents, according to manufacturer's instructions, were added to each well of the 96-well plate. The plates were incubated for the indicated times at 37° C., humidifying 5% $CO_2$ incubator, after which Absorbance at 492 nm was read using GENios microplate reader (TECAN).
Antibody Concentration Calculations
Rab-Zap-Saporin conjugate
Conversion of mg/ml to molarity was performed according to manufacturers' specifications. Generally, for Rab-Zap lot#69-30 calculations were performed as follows:
Concentration=1.12 mg/ml
MW=210 kDa (1.12 mg/ml)/(2.1×10^5 mg/mmole)=5.33×10^−6 mmole/ml=5.33 μM Rabbit Polyclonal Antibodies
Conversion of mg/ml to molarity was based on the general assumption that the molecular weight of IG is 150 kDa. Since the affinity purified antibody might include other serum proteins, this is only an estimation of the molarity and is not definite. The conversion of mg/ml to molarity for the primary antibodies is detailed in table 11 below.
Concentration=1 mg/ml
MW=150 kDa (1 mg/ml)/(1.5×10^5 mg/mmole)=6.66×10^−6 mmole/ml=6.66 μM

TABLE 11 conversion of primary antibody concentration from ng/ml to nM

| Antibody concentration (nM) | Antibody concentration (ng/ml) |
|---|---|
| 3 | 450.5 |
| 1 | 150.2 |
| 0.3 | 50.1 |
| 0.1 | 16.7 |

Example 8

Development of Fully Human Anti-TMEM154 Antibodies

Generation of Human Monoclonal Antibodies Against TMEM154 Antigen

Fusion proteins composed of the extracellular domain of the TMEM154 linked to an IgG2 Fc polypeptide are generated by standard recombinant methods and used as antigen for immunization.
Transgenic HuMab Mouse.

Fully human monoclonal antibodies to TMEM154 are prepared using mice from the HCo7 strain of the transgenic HuMab Mouse®, which expresses human antibody genes. In this mouse strain, the endogenous mouse kappa light chain gene has been homozygously disrupted as described in Chen et al. (1993) EMBO J. 12:811-820 and the endogenous mouse heavy chain gene has been homozygously disrupted as described in Example 1 of PCT Publication WO 01/09187. Furthermore, this mouse strain carries a human kappa light chain transgene, KCo5, as described in Fishwild et al. (1996) Nature Biotechnology 14:845-851, and a human heavy chain transgene, HCo7, as described in U.S. Pat. Nos. 5,545,806; 5,625,825; and 5,545,807.
HuMab Immunizations:

To generate fully human monoclonal antibodies to TMEM154 polypeptides, mice of the HCo7 HuMab Mouse® strain can be immunized with purified recombinant TMEM154 fusion protein derived from mammalian cells that are transfected with an expression vector containing the gene encoding the fusion protein. General immunization schemes for the HuMab Mouse® are described in Lonberg, N. et al (1994) Nature 368(6474): 856-859; Fishwild, D. et al. (1996) Nature Biotechnology 14: 845-851 and PCT Publication WO 98/24884. The mice are 6-16 weeks of age upon the first infusion of antigen. A purified recombinant TMEM154 antigen preparation (5-50 micro-grams, purified from transfected mammalian cells expressing TMEM154 fusion protein) is used to immunize the HuMab mice intraperitoneally.

Transgenic mice are immunized twice with antigen in complete Freund's adjuvant or Ribi adjuvant IP, followed by 3-21 days IP (up to a total of 11 immunizations) with the antigen in incomplete Freund's or Ribi adjuvant. The immune response is monitored by retroorbital bleeds. The plasma is screened by ELISA (as described below), and mice with sufficient titers of anti-TMEM154 human immunoglobulin are used for fusions.

Mice are boosted intravenously with antigen 3 days before sacrifice and removal of the spleen.

Selection of HuMab Mice® Producing Anti-TMEM154 Antibodies:

To select HuMab Mice® producing antibodies that bind TMEM154 polypeptides, sera from immunized mice is tested by a modified ELISA as originally described by Fishwild, D. et al. (1996). Briefly, microtiter plates are coated with purified recombinant TMEM154 fusion protein at 1-2 .mu.g/ml in PBS, 50 .mu.l/wells incubated 4 degrees C. overnight then blocked with 200 .mu.l/well of 5% BSA in PBS. Dilutions of plasma from TMEM154-immunized mice are added to each well and incubated for 1-2 hours at ambient temperature. The plates are washed with PBS/Tween and then incubated with a goat-anti-human kappa light chain polyclonal antibody conjugated with alkaline phosphatase for 1 hour at room temperature. After washing, the plates are developed with pNPP substrate and analyzed by spectrophotometer at OD 415-650. Mice that developed the highest titers of anti-TMEM154 antibodies are used for fusions. Fusions are performed as described below and hybridoma supernatants are tested for anti-TMEM154 activity by ELISA.

Generation Of Hybridomas Producing Human Monoclonal Antibodies to TMEM154 Polypeptides The mouse splenocytes, isolated from the HuMab mice, are fused with PEG to a mouse myeloma cell line based upon standard protocols. The resulting hybridomas are then screened for the production of antigen-specific antibodies. Single cell suspensions of splenic lymphocytes from immunized mice are fused to one-fourth the number of P3X63 Ag8.6.53 (ATCC CRL 1580) nonsecreting mouse myeloma cells with 50% PEG (Sigma). Cells are plated at approximately 1×10-5/well in flat bottom microtiter plate, followed by about two week incubation in selective medium containing 10% fetal calf serum, supplemented with origen (IGEN) in RPMI, L-glutamine, sodium pyruvate, HEPES, penicillin, streptamycin, gentamycin, 1×HAT, and beta-mercaptoethanol. After 1-2 weeks, cells are cultured in medium in which the HAT is replaced with HT. Individual wells are then screened by ELISA (described above) for human anti-TMEM154 monoclonal IgG antibodies. Once extensive hybridoma growth occurred, medium is monitored usually after 10-14 days. The antibody secreting hybridomas are replated, screened again and, if still positive for human IgG, anti-TMEM154 monoclonal antibodies are subcloned at least twice by limiting dilution. The stable subclones are then cultured in vitro to generate small amounts of antibody in tissue culture medium for further characterization.

Hybridoma clones are selected for further analysis.

Structural Characterization Of Desired Anti-TMEM154 Human Monoclonal Antibodies

The cDNA sequences encoding the heavy and light chain variable regions of the obtained anti-TMEM154 monoclonal antibodies are obtained from the resultant hybridomas, respectively, using standard PCR techniques and are sequenced using standard DNA sequencing techniques.

The nucleotide and amino acid sequences of the heavy chain variable region and of the light chain variable region are identified. These sequences may be compared to known human germline immunoglobulin light and heavy chain sequences and the CDRs of each heavy and light of the obtained anti-TMEM154 sequences identified.

Characterization of Binding Specificity and Binding Kinetics of Anti-TMEM154 Human Monoclonal Antibodies The binding affinity, binding kinetics, binding specificity, and cross-competition of anti-TMEM154 antibodies are examined by Biacore analysis. Also, binding specificity is examined by flow cytometry.

Binding Affinity and Kinetics anti-TMEM154 antibodies produced according to the invention are characterized for affinities and binding kinetics by Biacore analysis (Biacore AB, Uppsala, Sweden). Purified recombinant human TMEM154 fusion protein is covalently linked to a CM5 chip (carboxy methyl dextran coated chip) via primary amines, using standard amine coupling chemistry and kit provided by Biacore. Binding is measured by providing the antibodies in HBS EP buffer (provided by BIAcore AB) at a concentration of 267 nM and a flow rate of 50 .mu.l/min. The antigen-antibody association kinetics are followed for 3 minutes and the dissociation kinetics are followed for 7 minutes. The association and dissociation curves are fit to a 1:1 Langmuir binding model using BIAevaluation software (Biacore AB). To minimize the effects of avidity in the estimation of the binding constants, only the initial segments of data corresponding to association and dissociation phases are used for fitting.

Epitope Mapping of Obtained anti-TMEM154 Antibodies

Biacore is used to determine epitope grouping of anti-TMEM154 antibodies are used to map their epitopes on the TMEM154 antigen, respectively. These different antibodies are coated on three different surfaces of the same chip to 8000 RUs each. Dilutions of each of the mAbs are made, starting at 10 mu.g/mL and is incubated with Fc fused TMEM154 (50 nM) for one hour. The incubated complex is injected over all the three surfaces (and a blank surface) at the same time for 1.5 minutes at a flow rate of 20 .mu.L/min. Signal from each surface at end of 1.5 minutes, after subtraction of appropriate blanks, has been plotted against concentration of mAb in the complex. Upon analysis of the data, the anti-TMEM154 antibodies are categorized into different epitope groups depending on the epitope mapping results. The functional properties thereof are also compared.

Chinese hamster ovary (CHO) cell lines that express TMEM154 protein at the cell surface are developed and used to determine the specificity of the TMEM154 HuMAbs by flow cytometry. CHO cells are transfected with expression plasmids containing full length cDNA encoding transmembrane forms of TMEM154 antigen or a variant thereof. The transfected proteins contained an epitope tag at the N-terminus are used for detection by an antibody specific for the epitope. Binding of an anti-TMEM154 MAb is assessed by incubating the transfected cells with each of the TMEM154 antibodies at a concentration of 10 micro-grams/ml. The cells are washed and binding is detected with a FITC-labeled anti-human IgG Ab. A murine anti-epitope tag Ab, followed by labeled anti-murine IgG, is used as the positive control. Non-specific human and murine Abs are used as negative controls. The obtained data is used to assess the specificity of the HuMAbs for the TMEM154 antigen target.

These antibodies and other antibodies specific to TMEM154 polypeptides may be used in the afore-described anti-anti-TMEM154 related therapies such as treatment of cancers wherein TMEM154 antigen is differentially expressed, such as ovarian cancer, lung cancer, breast cancer, kidney cancer, liver cancer, pancreatic cancer, prostate cancer, melanoma and hematological malignancies such as multiple myeloma, lymphoma, Non-Hodgkin's lymphoma, anti CD20 (i.e. Rituximab) resistant lymphoma, leukemia and T cell leukemia, involving the TMEM154 antigen, such as in the treatment of cancers and inflammatory or autoimmune diseases wherein such antibodies will e.g., prevent negative stimulation of T cell activity against desired target cancer cells or prevent the positive stimulation of T cell activity thereby eliciting a desired anti-autoimmune effect.

Example 7

Clinical Trial of an Antibody or Therapeutic Agent According to any of the Above Embodiments A phase I trial of a therapeutic agent as described herein to subjects with active plasma cell disorder, e.g. multiple myeloma, light-chain amyloidosis, or plasma cell leukemia may be designed to evaluate both effect on disease progression and possible toxicity. Subjects with a suspected plasma cell disorder may be enrolled after positive diagnosis of plasma cell disorder as is well known in the art.

Treatment may be provided as a single therapeutic or in combination with accepted treatments. For example, treatment strategies for multiple myeloma are reviewed in Rajkumar et al., 2002, Mayo Clin. Proc. 77:814, hereby incorporated by reference in its entirety). Recognition of acute or unusual progression of the disease may halt administration of therapeutic agent.

Initial subjects receive a suitable dosage of therapeutic agent, administered for example as a 1 hour intravenous infusion or as appropriate, alone or in combination with one or more other known agents as could be selected by one of ordinary skill in the art. Given adequate tolerance, the dose will be increased stepwise in subsequent subjects. Additionally, the method for administration may be changed to bolus injection.

Toxicity of therapeutic agent is evaluated in subjects according to the World Health Organization Toxicity Criteria: blood pressure, temperature and heart rate are monitored every 10 minutes during infusion, then every hour for 3 hours and finally every 3 hours for 24 hours. Hematologic, renal and liver function tests are conducted every other day for one week and on day 15, 30, 60 and 120 post injection.

Serum and/or tissue samples are obtained once a week for two months so that the effects of the therapeutic agent may be determined by methods known in the art, e.g., change serum concentration of M protein, change in hemoglobin value, presence/regression of lytic bone lesions etc. Pathologic studies will assess treatment effect on tissue damage associated with the plasma cell disorder.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention is now further described by the claims which follow.

What is claimed is:

1. A method of treating a subject in need of treatment thereof for multiple myeloma, comprising administering to the subject a pharmaceutical composition comprising a polyclonal or monoclonal antibody, or antibody binding fragment, that specifically binds to a TMEM154 polypeptide comprising at least one of SEQ ID NOS: 10, 5, 62 or 63, or a fragment thereof, in a pharmaceutically acceptable carrier, and a second medicament, wherein said second medicament is suitable for treatment of multiple myeloma, wherein said antibody and said second medicament are provided in a single dosage form or separately, and wherein said second medicament is selected for a synergistic effect between said antibody and said second medicament; wherein said multiple myeloma is selected from the group consisting of aggressive multiple myeloma; refractory multiple myeloma, and drug resistant multiple myeloma.

2. The method of claim 1, wherein said aggressive multiple myeloma comprises primary plasma cell leukemia (PCL).

3. The method of claim 1, wherein said polyclonal or monoclonal antibody, or antibody binding fragment specifically binds to a TMEM154 polypeptide comprising SEQ ID NO: 10 or a fragment thereof.

4. The method of claim 3, wherein said polyclonal or monoclonal antibody, or antibody binding fragment specifically binds to a TMEM154 polypeptide consisting essentially of SEQ ID NO: 10.

5. The method of claim 1 wherein the antibody or fragment specifically binds to a polypeptide consisting essentially of an amino acid sequence of SEQ ID NO:5.

6. The method of claim 1, wherein the antibody or fragment specifically binds to a peptide consisting essentially of at least one SEQ ID NOS: 62 or 63.

7. The method of claim 1, wherein the antibody or fragment is selected from the group consisting of: a fully human antibody, a humanized or primatized antibody, a chimeric antibody, Fab, Fab', F(ab')2, F(ab'), F(ab), Fv or scFv fragment and minimal recognition unit.

8. The method of claim 1, wherein the antibody or fragment is coupled to a detectable marker, or to an effector moiety.

9. The method of claim 8, wherein: the effector moiety is one or more of a radionuclide, fluorophore, an enzyme, a toxin, a therapeutic agent, a chemotherapeutic agent, a cytokine antibody, a cytokine receptor, or an immunomodulatory agent; or the detectable marker is one or more of a radioisotope, a metal chelator, an enzyme, a fluorescent compound, a bioluminescent compound or a chemiluminescent compound.

10. The method of claim 1, wherein said multiple myeloma comprises a precursor form of the disease and wherein said precursor form of the disease is selected from the group consisting of MGUS (monoclonal gammopathy of undetermined significance), Waldenstrom's macroglobulinemia (WM, also known as lymphoplasmacytic lymphoma) which may proceed to multiple myeloma; smoldering multiple myeloma (SMM), indolent multiple myeloma, and premalignant forms of multiple myeloma which may also proceed to multiple myeloma.

11. A method of treating a subject in need of treatment thereof for multiple myeloma, comprising administering to the subject a pharmaceutical composition comprising a polyclonal or monoclonal antibody, or antibody binding fragment, that specifically binds to a TMEM154 polypeptide comprising at least one of SEQ ID NOS: 10, 5, 62 or 63, or a fragment thereof, in a pharmaceutically acceptable carrier, and a second medicament, wherein said second medicament is suitable for treatment of multiple myeloma, wherein said antibody and said second medicament are provided in a single dosage form or separately, and wherein said second medicament is selected for a synergistic effect between said antibody and said second medicament; wherein said multiple myeloma is selected from the group consisting of precursor to myeloma, multiple myeloma cancers which produce light chains of kappa-type and/or light chains of lambda-type.

* * * * *

SEQUENCE LISTING

<160> NUMBER OF SEQ ID NOS: 72

<210> SEQ ID NO 1
<211> LENGTH: 3349
<212> TYPE: DNA
<213> ORGANISM: Homo sapiens

<400> SEQUENCE: 1

```
ggctggagag gcgtgataat agaaccagtg cttcaacagc aacttctctt ttgcaatcct      60
tgctggtctg acaggctcct gcagaattac atcacttcct aaaaaacagg cacacacctc     120
tccttcaagt cagcaccgac ccaaacaagc aggaaacagg aaatgttcac gtttcagaga     180
ggctgcagcc cggcgcagca tcctgagcgc gcctctgccg aggcgagcgg acatgcaggc     240
tccccgcgca gccctagtct tcgccctggt gatcgcgctc gttcccgtcg gccggggtaa     300
ttatgaggaa ttagaaaact caggagatac aactgtggaa tctgaaagac caaataaagt     360
gactattcca agcacatttg ctgcagtgac catcaaagaa acattaaatg caaatataaa     420
ttctaccaac tttgctccgg atgaaaatca gttagagttt atactgatgg tgttaatccc     480
attgatttta ttggtcctct tacttttatc cgtggtattc cttgcaacat actataaaag     540
aaaaagaact aaacaagaac cttctagcca aggatctcag agtgctttac agacatatga     600
actgggaagt gaaaacgtga aagtccctat ttttgaggaa gatacaccct ctgttatgga     660
aattgaaatg gaagagcttg ataaatggat gaacagcatg aatagaaatg ccgactttga     720
```

```
atgtttacct accttgaagg aagagaagga atcaaatcac aacccaagtg acagtgaatc    780
ctaaacctga atggcgctca tgttttccaa gagaagcagc ccctgaggga gtctgctgag    840
gctgccaaca gaggatgaag aggatacaaa tttaattaat ttcaaatcaa catagacaca    900
agaaccttt gctgtttctt ccaacgccca ctcttcctaa tgatggcatc acttgcactt    960
ggaagaatgt gcaattgaga agtactagga aaaggcctgg ctgccatcca tcgctgcctc   1020
tgagggtgga gaaggaggcg ggtgatgtgc tcacttctga tcaacatgtg ttgcctcctc   1080
tcagccaact tctagctcac tgcactcact ctggtcatga taaatgttcg tcacctttct   1140
gcttcattcc ttagggccta aatcaggaag ctgttttatc gatggtttcc ttttgggtca   1200
gtaaccagct ttggataatt tcctctgatt attcaagtcg tgggacaggt aaactacatt   1260
cagcaggaac ttttctcgag gagtgttatg tcatggaaaa gacaccaaac acagcaagta   1320
ttttaatgaa tacaccatcc caggggggtca gtaagctctg cctgccaaga agacacagtg   1380
agaggggtcc acagtcctga tgaggtggcg tttggtaact tgtagaccct agcatggcca   1440
ggtctggtca cccttaagaa cttctcagag aaactaggaa tcttcagtga aagaactaat   1500
gttctcctca gctgaaattc ccttgcttgt cagcattct gcaaagctca cacttgtttc   1560
accataccct ccttggatgt gacatgtagg taggaagtat gtgcaggtgg gagtcatctg   1620
tcagccttct atgtttcaga tcctgaag gtggtttgaa acaaacagaa gaggagcagg   1680
aaatatccgt gcctgtggca gatctcactc atcatgctta gcattctctc ccgccaagct   1740
gggataagcc tcatgtccta acacagcaca acaggaggtc tctgtcagtc catcagagat   1800
gacattctat gtgatatttt tgacatcctt gtgctaaaag caatggcaca aaatggaaaa   1860
gggcctattg accacaccta ctccagtaaa attgttcttc atttattcct taattttcta   1920
aatctgaccc ctttaaagca atctagcaaa ttgagaatcc tcagctctcc ttggatacct   1980
gatattttat ttcaagaaag agacaaagaa ggaaaatttt atttattta ctacccacat   2040
ataaaccgaa gggagatggg actacccaaa catttgctgc tcaattttgt gtcttgtgct   2100
tgaaagtctg ccctaatgca taacaaaaac tacttgtctc ctacctttg ggatcccttt   2160
aacaagtatt tgccttctga actacgtgga taatttcaaa ggcagagttc cagaccagag   2220
aggtctttcc atacaatgaa agctataact agctggttgt gtttaaccac tgctatcacg   2280
ctatcctggg actgcataga actttgacaa agacagact tcatggtaca aacttcaac   2340
agattttctg tcatattctc accagcacat ctgaatgagg ctttgtgttt tccttgctct   2400
cttgcatgtt ccttttcaac tcatggccca cagtgactct cagagattta tgccaaaatt   2460
gcatacaatt gttttctgaa tcataacttg tctattttc tgcctatgtg tgctactttc   2520
agtttgttt tcatcaacat tttgactctc agaagagcct ccatttgccc ctttctctct   2580
ttaggtatct aagatctttg aacacctgga cctttacatt tgatccaacc ctatcaaata   2640
atgaacttct cagagaggca tctgggtcc tggaacttca tgttgatgaa gtcatatttat   2700
ataatatgat aaaaatattc tcatgcagta ttttaaataa tttcaaattc tagaagaagc   2760
aaatttcagc gacatgtcat tgagttttta tttggtaaag ctataattgt gcagtgtaca   2820
aagcactttt taaaaagata gtttattctg tcagggtata tgaagttagt atacagccag   2880
aacagccaag cctcaattct tgtaccttgt gtcttttta tactgtttaa tcaatagata   2940
tcatatgttt atgacagttt caagaattgt ttttaaaccc aaacttaatt ttatgtttca   3000
gactattgtt agaaaaacaa aacaaaaaac aaaaaaccc tcactaattt gccctaattg   3060
```

| | |
|---|---|
| gatagggcaa tcagaacaaa atctgacttt cgaatattta aaagatatgt aagtttgatt | 3120 |
| gcattttcgt acatttttaag caaactaggt taacaacaac atagcctagt caaacttctc | 3180 |
| aggaaacttg ttttaataaa tatgtaaaaa tacccattca tgactcttga cccaatggtg | 3240 |
| tgactcctcc ctctgggaag ggctttgtta cccaatgcaa gaccacagcc tggatccacc | 3300 |
| ttgatgtagg tggctcctgg ataacccaca tcaaacaaat gtgataaag | 3349 |

<210> SEQ ID NO 2
<211> LENGTH: 2767
<212> TYPE: DNA
<213> ORGANISM: Homo sapiens

<400> SEQUENCE: 2

| | |
|---|---|
| ggctggagag gcgtgataat agaaccagtg cttcaacagc aacttctctt ttgcaatcct | 60 |
| tgctggtctg acaggctcct gcagaattac atcacttcct aaaaaacagg cacacacctc | 120 |
| tccttcaagt cagcaccgac ccaaacaagc aggaaacagg aaatgttcac gtttcagaga | 180 |
| ggctgcagcc cggcgcagca tcctgagcgc gcctctgccg aggcgagcgg acatgcaggc | 240 |
| tccccgcgca gccctagtct tcgccctggt gatcgcgctc gttcccgtcg gccggggtaa | 300 |
| ttatgaggaa ttagaaaact caggagatac aactgtggaa tctgaaagac caaataaagt | 360 |
| gactattcca agcacatttg ctgcagtgac catcaaagaa acattaaatg caaatataaa | 420 |
| ttctaccaac tttgctccgg atgaaaatca gttagagttt atactgatgg tgttaatccc | 480 |
| attgatttta ttggtcctct tacttttatc cgtggtattc cttgcaacat actataaaag | 540 |
| aaaaagaact aaacaagaac cttctagcca aggatctcag agtgctttac agacatatga | 600 |
| actgggaagt gaaaacgtga aagtccctat ttttgaggaa gatacaccct ctgttatgga | 660 |
| aattgaaatg gaagagcttg ataaatggat gaacagcatg aatagaaatg ccgactttga | 720 |
| atgtttacct accttgaagg aagagaagga atcaaatcac aacccaagtg acagtgaatc | 780 |
| ctaaacctga atggcgctca tgttttccaa gagaagcagc ccctgaggga gtctgctgag | 840 |
| gctgccaaca gaggatgaag aggatacaaa tttaattaat ttcaaatcaa catagacaca | 900 |
| agaacctttt gctgtttctt ccaacgccca ctcttcctaa tgatggcatc acttgcactt | 960 |
| ggaagaatgt gcaattgaga agtactagga aaaggcctgg ctgccatcca tcgctgcctc | 1020 |
| tgagggtgga gaaggaggcg ggtgatgtgc tcacttctga tcaacatgtg ttgcctcctc | 1080 |
| tcagccaact tctagctcac tgcactcact ctggtcatga taaatgttcg tcacctttct | 1140 |
| gcttcattcc ttagggccta aatcaggaag ctgtttttatc gatggtttcc ttttgggtca | 1200 |
| gtaaccagct ttggataatt tcctctgatt attcaagtcg tgggacaggt aaactacatt | 1260 |
| cagcaggaac ttttctcgag gagtgttatg tcatggaaaa gacaccaaac acagcaagta | 1320 |
| ttttaatgaa tacaccatcc caggggggtca gtaagctctg cctgccaaga agacacagtg | 1380 |
| agagggggtcc acagtcctga tgaggtggcg tttggtaact tgtagaccct agcatggcca | 1440 |
| ggtctggtca cccttaagaa cttctcagag aaactaggaa tcttcagtga agaactaat | 1500 |
| gttctcctca gctgaaattc ccttgcttgt cagcatttct gcaaagctca cacttgtttc | 1560 |
| accatacctc ccttggatgt gacatgtagg taggaagtat gtgcaggtgg gagtcatctg | 1620 |
| tcagccttct atgtttcaga gatcctgaag gtggtttgaa acaaacagaa gaggagcagg | 1680 |
| aaatatccgt gcctgtggca gatctcactc atcatgctta gcattctctc ccgccaagct | 1740 |
| gggataagcc tcatgtccta acacagcaca acaggagggtc tctgtcagtc catcagagat | 1800 |
| gacattctat gtgatatttt tgacatcctt gtgctaaaag caatggcaca aaatggaaaa | 1860 |

```
gggcctattg accacaccta ctccagtaaa attgttcttc atttattcct aattttcta    1920
aatctgaccc ctttaaagca atctagcaaa ttgagaatcc tcagctctcc ttggatacct    1980
gatattttat ttcaagaaag agacaaagaa ggaaaatttt atttatttta ctacccacat    2040
ataaaccgaa gggagatggg actacccaaa catttgctgc tcaattttgt gtcttgtgct    2100
tgaaagtctg ccctaatgca taacaaaaac tacttgtctc ctaccttttg ggatcccttt    2160
aacaagtatt tgccttctga actacgtgga taatttcaaa ggcagagttc agaccagag    2220
aggtctttcc atacaatgaa agctataact agctggttgt gtttaaccac tgctatcacg    2280
ctatcctggg actgcataga actttgacaa aagacagact tcatggtaca caacttcaac    2340
agattttctg tcatattctc accagcacat ctgaatgagg ctttgtgttt tccttgctct    2400
cttgcatgtt cctttcaac tcatggccca cagtgactct cagagattta tgccaaaatt    2460
gcatacaatt gttttctgaa tcataacttg tctatttttc tgcctatgtg tgctactttc    2520
agtttgtttc tcatcaacat tttgactctc agaagagcct ccatttgccc ctttctctct    2580
ttaggtatct aagatctttg aacacctgga cctttacatt tgatccaacc ctatcaaata    2640
atgaacttct cagagaggca tctggggtcc tggaacttca tgttgatgaa gtcatattat    2700
ataatatgat aaaaatattc tcatgcagta ttttaaataa tttcaaattc tagaagaagc    2760
aaatttc                                                              2767

<210> SEQ ID NO 3
<211> LENGTH: 3398
<212> TYPE: DNA
<213> ORGANISM: Homo sapiens

<400> SEQUENCE: 3
ggctggagag gcgtgataat agaaccagtg cttcaacagc aacttctctt ttgcaatcct     60
tgctggtctg acaggctcct gcagaattac atcacttcct aaaaaacagg cacacacctc    120
tccttcaagt cagcaccgac ccaaacaagc aggaaacagg aaatgttcac gtttcagaga    180
ggctgcagcc cggcgcagca tcctgagcgc gcctctgccg aggcgagcgg acatgcaggc    240
tccccgcgca gccctagtct tcgccctggt gatcgcgctc gttcccgtcg gccggggtaa    300
gccgcctcca cttcctactc ctgggaagga ggatcgcaaa agctggtaat tatgaggaat    360
tagaaaactc aggagataca actgtggaat ctgaaagacc aaataaagtg actattccaa    420
gcacatttgc tgcagtgacc atcaaagaaa cattaaatgc aaatataaat tctaccaact    480
ttgctccgga tgaaaatcag ttagagttta tactgatggt gttaatccca ttgatttat    540
tggtcctctt acttttatcc gtggtattcc ttgcaacata ctataaaaga aaaagaacta    600
aacaagaacc ttctagccaa ggatctcaga gtgctttaca gacatatgaa ctgggaagtg    660
aaaacgtgaa agtccctatt tttgaggaag atacaccctc tgttatggaa attgaaatgg    720
aagagcttga taatggatg aacagcatga atagaaatgc cgactttgaa tgtttaccta    780
ccttgaagga agagaaggaa tcaaatcaca acccaagtga cagtgaatcc taaacctgaa    840
tggcgctcat gttttccaag agaagcagcc cctgagggag tctgctgagg ctgccaacag    900
aggatgaaga ggatacaaat ttaattaatt tcaaatcaac atagacacaa gaacctttg     960
ctgtttcttc aacgcccac tcttcctaat gatggcatca cttgcacttg aagaatgtg    1020
caattgagaa gtactaggaa aaggcctggc tgccatccat cgctgcctct gagggtggag    1080
aaggaggcgg gtgatgtgct cacttctgat caacatgtgt tgcctcctct cagccaactt    1140
```

```
ctagctcact gcactcactc tggtcatgat aaatgttcgt cacctttctg cttcattcct    1200
tagggcctaa atcaggaagc tgttttatcg atggtttcct tttgggtcag taaccagctt    1260
tggataattt cctctgatta ttcaagtcgt gggacaggta aactacattc agcaggaact    1320
tttctcgagg agtgttatgt catggaaaag acaccaaaca cagcaagtat tttaatgaat    1380
acaccatccc aggggggtcag taagctctgc ctgccaagaa gacacagtga gagggtcca    1440 cagtcctgat gaggtggcgt ttggtaactt gtagaccta gcatggccag gtctggtcac    1500
ccttaagaac ttctcagaga aactaggaat cttcagtgaa agaactaatg ttctcctcag    1560
ctgaaattcc cttgcttgtc agcatttctg caaagctcac acttgtttca ccatacctcc    1620
cttggatgtg acatgtaggt aggaagtatg tgcaggtggg agtcatctgt cagccttcta    1680
tgtttcagag atcctgaagg tggttttgaaa caaacagaag aggagcagga aatatccgtg    1740
cctgtggcag atctcactca tcatgcttag cattctctcc cgccaagctg ggataagcct    1800
catgtcctaa cacagcacaa caggaggtct ctgtcagtcc atcagagatg acattctatg    1860
tgatattttt gacatccttg tgctaaaagc aatggcacaa aatggaaaag ggctattga    1920 ccacacctac tccagtaaaa ttgttcttca tttattcctt aattttctaa atctgacccc    1980
tttaaagcaa tctagcaaat tgagaatcct cagctctcct tggatacctg atattttatt    2040
tcaagaaaga gacaaagaag gaaaatttta tttattttac tacccacata taaaccgaag    2100
ggagatggga ctacccaaac atttgctgct caattttgtg tcttgtgctt gaaagtctgc    2160
cctaatgcat aacaaaaact acttgtctcc tacctttggg atccctttta acaagtattt    2220
gccttctgaa ctacgtggat aatttcaaag gcagagttcc agaccagaga ggtctttcca    2280
tacaatgaaa gctataacta gctggttgtg tttaaccact gctatcacgc tatcctggga    2340
ctgcatagaa ctttgacaaa agacagactt catggtacac aacttcaaca gattttctgt    2400
catattctca ccagcacatc tgaatgaggc tttgtgtttt ccttgctctc ttgcatgttc    2460
cttttcaact catggcccac agtgactctc agagattat gccaaaattg catacaattg    2520
ttttctgaat cataacttgt ctattttct gcctatgtgt gctactttca gtttgtttct    2580
catcaacatt tgactctca gaagagcctc catttgcccc tttctctctt taggtatcta    2640
agatctttga acacctggac ctttacattt gatccaaccc tatcaaataa tgaacttctc    2700
agagaggcat ctggggtcct ggaacttcat gttgatgaag tcatattata taatatgata    2760
aaaatattct catgcagtat tttaaataat ttcaaattct agaagaagca aatttcagcg    2820
acatgtcatt gagttttat ttggtaaagc tataattgtg cagtgtacaa agcacttttt    2880
aaaaagatag tttattctgt cagggtatat gaagttagta tacagccaga acagccaagc    2940
ctcaattctt gtaccttgtg tcttttttatt actgtttaat caatagatat catatgttta    3000
tgacagtttc aagaattgtt tttaaaccca aacttaattt tatgtttcag actattgtta    3060
gaaaaacaaa acaaaaaaca aaaaaaccct cactaatttg ccctaattgg atagggcaat    3120
cagaacaaaa tctgactttc gaatatttaa aagatatgta agtttgattg cattttcgta    3180 catttttaagc aaactaggtt aacaacaaca tagcctagtc aaacttctca ggaaacttgt    3240
tttaataaat atgtaaaaat acccattcat gactcttgac ccaatggtgt gactcctccc    3300
tctgggaagg gctttgttac ccaatgcaag accacagcct ggatccacct tgatgtaggt    3360
ggctcctgga taacccacat caaacaaatg tgataaag                            3398
```

<210> SEQ ID NO 4
<211> LENGTH: 776

```
<212> TYPE: DNA
<213> ORGANISM: Homo sapiens

<400> SEQUENCE: 4
ggctggagag gcgtgataat agaaccagtg cttcaacagc aacttctctt ttgcaatcct      60
tgctggtctg acaggctcct gcagaattac atcacttcct aaaaaacagg cacacacctc     120
tccttcaagt cagcaccgac ccaaacaagc aggaaacagg aaatgttcac gtttcagaga     180
ggctgcagcc cggcgcagca tcctgagcgc gcctctgccg aggcgagcgg acatgcaggc     240
tccccgcgca gccctagtct tcgccctggt gatcgcgctc gttcccgtcg gccggggtaa     300
ttatgaggaa ttagaaaact caggagatac aactgtggaa tctgaaagac aaataaagt      360
gactattcca agcacatttg ctgcagtgac catcaaagaa acattaaatg caaatataaa     420
ttctaccaac tttgctccgg atgaaaatca gttagagttt atactgatgg tgttaatccc     480
attgatttta ttggtcctct tacttttatc cgtggtattc cttgcaacat actataaaag     540
aaaaagaact aaacaagaac cttctagcca aggatctcag agtgctttac agacatgtaa     600
aatacaacta tcatggaagg tcataccagc gttttgcttg gaaagctccc acagaaatgc     660
tttataggag agcatggaca cctgcacact atgtcccctg ggaagttaga agcagacata     720
ctgtttctta ctgcacttgg gtagagcctg gtctgttata ctatactagg aaataa         776

<210> SEQ ID NO 5
<211> LENGTH: 183
<212> TYPE: PRT
<213> ORGANISM: Homo sapiens

<400> SEQUENCE: 5

Met Gln Ala Pro Arg Ala Ala Leu Val Phe Ala Leu Val Ile Ala Leu
1               5                   10                  15

Val Pro Val Gly Arg Gly Asn Tyr Glu Glu Leu Glu Asn Ser Gly Asp
            20                  25                  30

Thr Thr Val Glu Ser Glu Arg Pro Asn Lys Val Thr Ile Pro Ser Thr
        35                  40                  45

Phe Ala Ala Val Thr Ile Lys Glu Thr Leu Asn Ala Asn Ile Asn Ser
    50                  55                  60

Thr Asn Phe Ala Pro Asp Glu Asn Gln Leu Glu Phe Ile Leu Met Val
65                  70                  75                  80

Leu Ile Pro Leu Ile Leu Leu Val Leu Leu Leu Ser Val Val Phe
                85                  90                  95

Leu Ala Thr Tyr Tyr Lys Arg Lys Arg Thr Lys Gln Glu Pro Ser Ser
                100                 105                 110

Gln Gly Ser Gln Ser Ala Leu Gln Thr Tyr Glu Leu Gly Ser Glu Asn
            115                 120                 125

Val Lys Val Pro Ile Phe Glu Glu Asp Thr Pro Ser Val Met Glu Ile
        130                 135                 140

Glu Met Glu Glu Leu Asp Lys Trp Met Asn Ser Met Asn Arg Asn Ala
145                 150                 155                 160

Asp Phe Glu Cys Leu Pro Thr Leu Lys Glu Glu Lys Glu Ser Asn His
                165                 170                 175

Asn Pro Ser Asp Ser Glu Ser
            180

<210> SEQ ID NO 6
<211> LENGTH: 128
<212> TYPE: PRT
```

<213> ORGANISM: Homo sapiens

<400> SEQUENCE: 6

Glu Thr Leu Asn Ala Asn Ile Asn Ser Thr Asn Phe Ala Pro Asp Glu
1               5                   10                  15

Asn Gln Leu Glu Phe Ile Leu Met Val Leu Ile Pro Leu Ile Leu Leu
            20                  25                  30

Val Leu Leu Leu Leu Ser Val Val Phe Leu Ala Thr Tyr Tyr Lys Arg
        35                  40                  45

Lys Arg Thr Lys Gln Glu Pro Ser Ser Gln Gly Ser Gln Ser Ala Leu
    50                  55                  60

Gln Thr Tyr Glu Leu Gly Ser Glu Asn Val Lys Val Pro Ile Phe Glu
65                  70                  75                  80

Glu Asp Thr Pro Ser Val Met Glu Ile Glu Met Glu Glu Leu Asp Lys
                85                  90                  95

Trp Met Asn Ser Met Asn Arg Asn Ala Asp Phe Glu Cys Leu Pro Thr
            100                 105                 110

Leu Lys Glu Glu Lys Glu Ser Asn His Asn Pro Ser Asp Ser Glu Ser
        115                 120                 125

<210> SEQ ID NO 7
<211> LENGTH: 183
<212> TYPE: PRT
<213> ORGANISM: Homo sapiens

<400> SEQUENCE: 7

Met Gln Ala Pro Arg Ala Ala Leu Val Phe Ala Leu Val Ile Ala Leu
1               5                   10                  15

Val Pro Val Gly Arg Gly Asn Tyr Glu Glu Leu Glu Asn Ser Gly Asp
            20                  25                  30

Thr Thr Val Glu Ser Glu Arg Pro Asn Lys Val Thr Ile Pro Ser Thr
        35                  40                  45

Phe Ala Ala Val Thr Ile Lys Glu Thr Leu Asn Ala Asn Ile Asn Ser
    50                  55                  60

Thr Asn Phe Ala Pro Asp Glu Asn Gln Leu Glu Phe Ile Leu Met Val
65                  70                  75                  80

Leu Ile Pro Leu Ile Leu Leu Val Leu Leu Leu Phe Val Val Phe
                85                  90                  95

Leu Ala Thr Tyr Tyr Lys Arg Lys Arg Thr Lys Gln Glu Pro Ser Ser
            100                 105                 110

Gln Gly Ser Gln Ser Ala Leu Gln Thr Tyr Glu Leu Gly Ser Glu Asn
        115                 120                 125

Val Lys Val Pro Ile Phe Glu Glu Asp Thr Pro Ser Val Met Glu Ile
    130                 135                 140

Glu Met Glu Glu Leu Asp Lys Trp Met Asn Ser Met Asn Arg Asn Ala
145                 150                 155                 160

Asp Phe Glu Cys Leu Pro Thr Leu Lys Glu Glu Lys Glu Ser Asn His
                165                 170                 175

Asn Pro Ser Asp Ser Glu Ser
            180

<210> SEQ ID NO 8
<211> LENGTH: 105
<212> TYPE: PRT
<213> ORGANISM: Homo sapiens

<400> SEQUENCE: 8

```
Met Val Leu Ile Pro Leu Ile Leu Leu Val Leu Leu Leu Ser Val
1               5                   10                  15

Val Phe Leu Ala Thr Tyr Tyr Lys Arg Lys Arg Thr Lys Gln Glu Pro
            20                  25                  30

Ser Ser Gln Gly Ser Gln Ser Ala Leu Gln Thr Tyr Glu Leu Gly Ser
        35                  40                  45

Glu Asn Val Lys Val Pro Ile Phe Glu Glu Asp Thr Pro Ser Val Met
    50                  55                  60

Glu Ile Glu Met Glu Glu Leu Asp Lys Trp Met Asn Ser Met Asn Arg
65                  70                  75                  80

Asn Ala Asp Phe Glu Cys Leu Pro Thr Leu Lys Glu Glu Lys Glu Ser
            85                  90                  95

Asn His Asn Pro Ser Asp Ser Glu Ser
            100                 105
```

<210> SEQ ID NO 9
<211> LENGTH: 144
<212> TYPE: PRT
<213> ORGANISM: Homo sapiens

<400> SEQUENCE: 9

```
Met Gln Ala Pro Arg Ala Ala Leu Val Phe Ala Leu Val Ile Ala Leu
1               5                   10                  15

Val Pro Val Gly Arg Gly Asn Tyr Glu Leu Glu Asn Ser Gly Asp
            20                  25                  30

Thr Thr Val Glu Ser Glu Arg Pro Asn Lys Val Thr Ile Pro Ser Thr
        35                  40                  45

Phe Ala Ala Val Thr Ile Lys Glu Thr Leu Asn Ala Asn Ile Asn Ser
    50                  55                  60

Thr Asn Phe Ala Pro Asp Glu Asn Gln Leu Glu Phe Ile Leu Met Val
65                  70                  75                  80

Leu Ile Pro Leu Ile Leu Leu Val Leu Leu Leu Ser Val Val Phe
            85                  90                  95

Leu Ala Thr Tyr Tyr Lys Arg Lys Arg Thr Lys Gln Glu Pro Ser Ser
            100                 105                 110

Gln Gly Ser Gln Ser Ala Leu Gln Thr Cys Lys Ile Gln Leu Ser Trp
        115                 120                 125

Lys Val Ile Pro Ala Phe Cys Leu Glu Ser Ser His Arg Asn Ala Leu
    130                 135                 140
```

<210> SEQ ID NO 10
<211> LENGTH: 51
<212> TYPE: PRT
<213> ORGANISM: Artificial sequence
<220> FEATURE:
<223> OTHER INFORMATION: Synthetic construct

<400> SEQUENCE: 10

```
Glu Glu Leu Glu Asn Ser Gly Asp Thr Thr Val Glu Ser Glu Arg Pro
1               5                   10                  15

Asn Lys Val Thr Ile Pro Ser Thr Phe Ala Ala Val Thr Ile Lys Glu
            20                  25                  30

Thr Leu Asn Ala Asn Ile Asn Ser Thr Asn Phe Ala Pro Asp Glu Asn
        35                  40                  45

Gln Leu Glu
    50
```

<210> SEQ ID NO 11
<211> LENGTH: 86
<212> TYPE: PRT
<213> ORGANISM: Artificial sequence
<220> FEATURE:
<223> OTHER INFORMATION: Synthetic construct

<400> SEQUENCE: 11

Ala Thr Tyr Tyr Lys Arg Lys Arg Thr Lys Gln Glu Pro Ser Ser Gln
1               5                   10                  15

Gly Ser Gln Ser Ala Leu Gln Thr Tyr Glu Leu Gly Ser Glu Asn Val
            20                  25                  30

Lys Val Pro Ile Phe Glu Glu Asp Thr Pro Ser Val Met Glu Ile Glu
        35                  40                  45

Met Glu Glu Leu Asp Lys Trp Met Asn Ser Met Asn Arg Asn Ala Asp
    50                  55                  60

Phe Glu Cys Leu Pro Thr Leu Lys Glu Glu Lys Glu Ser Asn His Asn
65                  70                  75                  80

Pro Ser Asp Ser Glu Ser
                85

<210> SEQ ID NO 12
<211> LENGTH: 21
<212> TYPE: DNA
<213> ORGANISM: Artificial sequence
<220> FEATURE:
<223> OTHER INFORMATION: Oligonucleotide

<400> SEQUENCE: 12
aatttgtcaa gtcggtgcag c                                            21

<210> SEQ ID NO 13
<211> LENGTH: 20
<212> TYPE: DNA
<213> ORGANISM: Artificial sequence
<220> FEATURE:
<223> OTHER INFORMATION: Oligonucleotide

<400> SEQUENCE: 13
tcaccccttc attttgcgt                                               20

<210> SEQ ID NO 14
<211> LENGTH: 106
<212> TYPE: DNA
<213> ORGANISM: Homo sapiens

<400> SEQUENCE: 14
aatttgtcaa gtcggtgcag ctggcaagac ctaaaggatt atatgcgtca ggcaggagaa    60
gtgacttatg cagatgctca caagggacgc aaaaatgaag gggtga                 106

<210> SEQ ID NO 15
<211> LENGTH: 21
<212> TYPE: DNA
<213> ORGANISM: Artificial sequence
<220> FEATURE:
<223> OTHER INFORMATION: Oligonucleotide

<400> SEQUENCE: 15
gctccaggcc ataaggactt c                                            21

<210> SEQ ID NO 16
<211> LENGTH: 21

```
<212> TYPE: DNA
<213> ORGANISM: Artificial sequence
<220> FEATURE:
<223> OTHER INFORMATION: Oligonucleotide

<400> SEQUENCE: 16
cagcttcaaa ctctcccctg c                                               21

<210> SEQ ID NO 17
<211> LENGTH: 103
<212> TYPE: DNA
<213> ORGANISM: Homo sapiens

<400> SEQUENCE: 17
gctccaggcc ataaggactt cattccaaat atgattacag gagcagccca ggcggatgta     60
gctgttttag ttgtagatgc cagcagggga gagtttgaag ctg                      103

<210> SEQ ID NO 18
<211> LENGTH: 20
<212> TYPE: DNA
<213> ORGANISM: Artificial sequence
<220> FEATURE:
<223> OTHER INFORMATION: Oligonucleotide

<400> SEQUENCE: 18
ttccttgcca ggacctagag                                                 20

<210> SEQ ID NO 19
<211> LENGTH: 20
<212> TYPE: DNA
<213> ORGANISM: Artificial sequence
<220> FEATURE:
<223> OTHER INFORMATION: Oligonucleotide

<400> SEQUENCE: 19
cataaacctt tcgccttgac                                                 20

<210> SEQ ID NO 20
<211> LENGTH: 128
<212> TYPE: DNA
<213> ORGANISM: Homo sapiens

<400> SEQUENCE: 20
ttccttgcca ggacctagag tttgttcagt tccaccccac aggcatatat ggtgctggtt     60
gtctcattac ggaaggatgt cgtggagagg gaggcattct cattaacagt caaggcgaaa    120
ggtttatg                                                              128

<210> SEQ ID NO 21
<211> LENGTH: 20
<212> TYPE: DNA
<213> ORGANISM: Artificial sequence
<220> FEATURE:
<223> OTHER INFORMATION: Oligonucleotide

<400> SEQUENCE: 21
cagccaggtt atgccaacac                                                 20

<210> SEQ ID NO 22
<211> LENGTH: 21
<212> TYPE: DNA
<213> ORGANISM: Artificial sequence
<220> FEATURE:
<223> OTHER INFORMATION: Oligonucleotide
```

```
<400> SEQUENCE: 22
tcaaagcagg cgaacttcat c                                              21

<210> SEQ ID NO 23
<211> LENGTH: 140
<212> TYPE: DNA
<213> ORGANISM: Homo sapiens

<400> SEQUENCE: 23
cagccaggtt atgccaacac tttgagggat gcagctccca aaatgtataa ggaagaaggc    60
ctaaaagcat tctacaaggg ggttgctcct ctctggatga gacagatacc atacaccatg  120
atgaagttcg cctgctttga                                              140

<210> SEQ ID NO 24
<211> LENGTH: 20
<212> TYPE: DNA
<213> ORGANISM: Artificial sequence
<220> FEATURE:
<223> OTHER INFORMATION: Oligonucleotide

<400> SEQUENCE: 24
cggtttgctg cggtaatcat                                                20

<210> SEQ ID NO 25
<211> LENGTH: 21
<212> TYPE: DNA
<213> ORGANISM: Artificial sequence
<220> FEATURE:
<223> OTHER INFORMATION: Oligonucleotide

<400> SEQUENCE: 25
tttcttgctg ccagtctgga c                                              21

<210> SEQ ID NO 26
<211> LENGTH: 122
<212> TYPE: DNA
<213> ORGANISM: Homo sapiens

<400> SEQUENCE: 26
cggtttgctg cggtaatcat gaggataaga gagccacgaa ccacggcact gattttcagt    60
tctgggaaaa tggtgtgcac aggagccaag agtgaagaac agtccagact ggcagcaaga  120
aa                                                                 122

<210> SEQ ID NO 27
<211> LENGTH: 19
<212> TYPE: DNA
<213> ORGANISM: Artificial sequence
<220> FEATURE:
<223> OTHER INFORMATION: Oligonucleotide

<400> SEQUENCE: 27
atttgggtcg cggttcttg                                                 19

<210> SEQ ID NO 28
<211> LENGTH: 21
<212> TYPE: DNA
<213> ORGANISM: Artificial sequence
<220> FEATURE:
<223> OTHER INFORMATION: Oligonucleotide

<400> SEQUENCE: 28
tgccttgaca ttctcgatgg t                                              21
```

<210> SEQ ID NO 29
<211> LENGTH: 133
<212> TYPE: DNA
<213> ORGANISM: Homo sapiens

<400> SEQUENCE: 29
atttgggtcg cggttcttgt ttgtggatcg ctgtgatcgt cacttgacaa tgcagatctt    60
cgtgaagact ctgactggta agaccatcac cctcgaggtt gagcccagtg acaccatcga   120
gaatgtcaag gca                                                      133

<210> SEQ ID NO 30
<211> LENGTH: 20
<212> TYPE: DNA
<213> ORGANISM: Artificial sequence
<220> FEATURE:
<223> OTHER INFORMATION: Oligonucleotide

<400> SEQUENCE: 30
tgggaacaag agggcatctg                                                20

<210> SEQ ID NO 31
<211> LENGTH: 22
<212> TYPE: DNA
<213> ORGANISM: Artificial sequence
<220> FEATURE:
<223> OTHER INFORMATION: Oligonucleotide

<400> SEQUENCE: 31
ccaccactgc atcaaattca tg                                             22

<210> SEQ ID NO 32
<211> LENGTH: 86
<212> TYPE: DNA
<213> ORGANISM: Homo sapiens

<400> SEQUENCE: 32
tgggaacaag agggcatctg ctaaagtttc agattccatt tctgctcagt atccagtagt    60
ggatcatgaa tttgatgcag tggtgg                                         86

<210> SEQ ID NO 33
<211> LENGTH: 21
<212> TYPE: DNA
<213> ORGANISM: Artificial sequence
<220> FEATURE:
<223> OTHER INFORMATION: Oligonucleotide

<400> SEQUENCE: 33
tgacactggc aaaacaatgc a                                              21

<210> SEQ ID NO 34
<211> LENGTH: 21
<212> TYPE: DNA
<213> ORGANISM: Artificial sequence
<220> FEATURE:
<223> OTHER INFORMATION: Oligonucleotide

<400> SEQUENCE: 34 ggtcctttc accagcaagc t                                               21

<210> SEQ ID NO 35
<211> LENGTH: 94
<212> TYPE: DNA

<213> ORGANISM: Homo sapiens

<400> SEQUENCE: 35
tgacactggc aaaacaatgc agactttgct ttccttggtc aggcagtata atccaaagat    60
ggtcaaggtc gcaagcttgc tggtgaaaag gacc                               94

<210> SEQ ID NO 36
<211> LENGTH: 20
<212> TYPE: DNA
<213> ORGANISM: Artificial sequence
<220> FEATURE:
<223> OTHER INFORMATION: Oligonucleotide

<400> SEQUENCE: 36
gaggccgtca ccaagaacat                                               20

<210> SEQ ID NO 37
<211> LENGTH: 19
<212> TYPE: DNA
<213> ORGANISM: Artificial sequence
<220> FEATURE:
<223> OTHER INFORMATION: Oligonucleotide

<400> SEQUENCE: 37
ggacagccgg tcagagctc                                                19

<210> SEQ ID NO 38
<211> LENGTH: 111
<212> TYPE: DNA
<213> ORGANISM: Homo sapiens

<400> SEQUENCE: 38
gaggccgtca ccaagaacat tcacgagtcc tgcatgagcc agataggctg gaaccgcatc    60
atcgtggaga agcccttcgg gagggacctg cagagctctg accggctgtc c           111

<210> SEQ ID NO 39
<211> LENGTH: 25
<212> TYPE: DNA
<213> ORGANISM: Artificial sequence
<220> FEATURE:
<223> OTHER INFORMATION: Oligonucleotide

<400> SEQUENCE: 39
ccttctagcc aaggatctca gagtg                                         25

<210> SEQ ID NO 40
<211> LENGTH: 26
<212> TYPE: DNA
<213> ORGANISM: Artificial sequence
<220> FEATURE:
<223> OTHER INFORMATION: Oligonucleotide

<400> SEQUENCE: 40
cttgggttgt gatttgattc cttctc                                        26

<210> SEQ ID NO 41
<211> LENGTH: 209
<212> TYPE: DNA
<213> ORGANISM: Homo sapiens

<400> SEQUENCE: 41
ccttctagcc aaggatctca gagtgcttta cagacatatg aactgggaag tgaaaacgtg    60
aaagtcccta ttttgaggaa agatacaccc tctgttatgg aaattgaaat ggaagagctt   120
gataaatgga tgaacagcat gaatagaaat gccgactttg aatgtttacc taccttgaag    180
gaagagaagg aatcaaatca aacccaag                                       209

<210> SEQ ID NO 42
<211> LENGTH: 24
<212> TYPE: DNA
<213> ORGANISM: Artificial sequence
<220> FEATURE:
<223> OTHER INFORMATION: Oligonucleotide

<400> SEQUENCE: 42
aacatcatgg atcagaacaa cagc                                           24

<210> SEQ ID NO 43
<211> LENGTH: 26
<212> TYPE: DNA
<213> ORGANISM: Artificial sequence
<220> FEATURE:
<223> OTHER INFORMATION: Oligonucleotide

<400> SEQUENCE: 43
atcattggac taaagatagg gattcc                                         26

<210> SEQ ID NO 44
<211> LENGTH: 101
<212> TYPE: DNA
<213> ORGANISM: Homo sapiens

<400> SEQUENCE: 44
aacatcatgg atcagaacaa cagcctgcca ccttacgctc agggcttggc ctcccctcag    60
ggtgccatga ctcccggaat ccctatcttt agtccaatga t                        101

<210> SEQ ID NO 45
<211> LENGTH: 2405
<212> TYPE: DNA
<213> ORGANISM: Homo sapiens

<400> SEQUENCE: 45
tccggcgtgg tgcgcaggcg cggtatcccc cctcccccgc cagctcgacc ccggtgtggt    60
gcgcaggcgc agtctgcgca gggactggcg ggactgcgcg gcggcaacag cagacatgtc    120
gggggtccgg ggcctgtcgc ggctgctgag cgctcggcgc ctggcgctgg ccaaggcgtg    180
gccaacagtg ttgcaaacag gaacccgagg ttttcacttc actgttgatg gaacaagag    240 ggcatctgct aaagtttcag attccatttc tgctcagtat ccagtagtgg atcatgaatt    300
tgatgcagtg gtggtaggcg ctggaggggc aggcttgcga gctgcatttg gcctttctga    360
ggcagggttt aatacagcat gtgttaccaa gctgtttcct accaggtcac acactgttgc    420
agcacaggga ggaatcaatg ctgctctggg gaacatggag gaggacaact ggaggtggca    480
tttctacgac accgtgaagg ctccgactg gctgggggac caggatgcca tccactacat    540
gacggagcag gcccccgccg ccgtggtcga gctagaaaat tatggcatgc cgtttagcag    600
aactgaagat gggaagattt atcagcgtgc atttggtgga cagagcctca gtttggaaa    660 gggcgggcag gcccatcggt gctgctgtgt ggctgatcgg actggccact cgctattgca    720
caccttatat ggaaggtctc tgcgatatga taccagctat tttgtggagt attttgcctt    780
ggatctcctg atgagaatg gggagtgccg tggtgtcatc gcactgtgca tagaggacgg    840
gtccatccat cgcataagag caaagaacac tgttgttgcc acaggaggct acgggcgcac    900

```
ctacttcagc tgcacgtctg cccacaccag cactggcgac ggcacggcca tgatcaccag    960
ggcaggcctt ccttgccagg acctagagtt tgttcagttc caccctacag gcatatatgg   1020
tgctggttgt ctcattacgg aaggatgtcg tggagaggga ggcattctca ttaacagtca   1080
aggcgaaagg tttatggagc gatacgcccc tgtcgcgaag gacctggcgt ctagagatgt   1140
ggtgtctcgg tccatgactc tggagatccg agaaggaaga ggctgtggcc ctgagaaaga   1200
tcacgtctac ctgcagctgc accacctacc tccagagcag ctggccacgc gcctgcctgg   1260
catttcagag acagccatga tcttcgctgg cgtggacgtc acgaaggagc cgatccctgt   1320
cctccccacc gtgcattata acatgggcgg cattcccacc aactacaagg ggcaggtcct   1380
gaggcacgtg aatggccagg atcagattgt gcccggcctg tacgcctgtg gggaggccgc   1440
ctgtgcctcg gtacatggtg ccaaccgcct cggggcaaac tcgctcttgg acctggttgt   1500
ctttggtcgg gcatgtgccc tgagcatcga agagtcatgc aggcctggag ataaagtccc   1560
tccaattaaa ccaaacgctg ggaagaatc tgtcatgaat cttgacaaat tgagatttgc   1620
tgatggaagc ataagaacat cggaactgcg actcagcatg cagaagtcaa tgcaaaatca   1680
tgctgccgtg ttccgtgtgg gaagcgtgtt gcaagaaggt tgtgggaaaa tcagcaagct   1740
ctatggagac ctaaagcacc tgaagacgtt cgaccgggga atggtctgga cacggacct   1800 ggtggagacc ctggagctgc agaacctgat gctgtgtgcg ctgcagacca tctacggagc   1860
agaggcacgg aaggagtcac ggggcgcgca tgccagggaa gactacaagg tgcggattga   1920
tgagtacgat tactccaagc ccatccaggg gcaacagaag aagcccttg aggagcactg   1980 gaggaagcac accctgtcct atgtggacgt tggcactggg aaggtcactc tggaatatag   2040
acccgtgatc gacaaaactt tgaacgaggc tgactgtgcc accgtcccgc cagccattcg   2100
ctcctactga tgagacaaga tgtggtgatg acagaatcag cttttgtaat tatgtataat   2160
agctcatgca tgtgtccatg tcataactgt cttcatacgc ttctgcactc tggggaagaa   2220
ggagtacatt gaagggagat tggcacctag tggctgggag cttgccagga acccagtggc   2280
cagggagcgt ggcacttacc tttgtccctt gcttcattct tgtgagatga taaaactggg   2340
cacagctctt aaataaaata taaatgaaca aactttcttt tatttccaaa aaaaaaaaaa   2400
aaaaa                                                               2405
```

<210> SEQ ID NO 46  
<211> LENGTH: 1435  
<212> TYPE: DNA  
<213> ORGANISM: Homo sapiens

<400> SEQUENCE: 46

```
ggcggggcct gcttctcctc agcttcaggc ggctgcgacg agccctcagg cgaacctctc     60
ggctttcccg cgcggcgccg cctcttgctg cgcctccgcc tcctcctctg ctccgccacc    120
ggcttcctcc tcctgagcag tcagcccgcg cgccggccgg ctccgttatg gcgaccccgca   180 gccctggcgt cgtgattagt gatgatgaac caggttatga ccttgattta ttttgcatac    240
ctaatcatta tgctgaggat ttggaaaggg tgtttattcc tcatggacta attatggaca    300
ggactgaacg tcttgctcga gatgtgatga aggagatggg aggccatcac attgtagccc    360
tctgtgtgct caagggggggc tataaattct ttgctgacct gctggattac atcaaagcac    420
tgaatagaaa tagtgataga tccattccta tgactgtaga ttttatcaga ctgaagagct    480
attgtaatga ccagtcaaca ggggacataa agtaattgg tggagatgat ctctcaactt     540
taactggaaa gaatgtcttg attgtggaag atataattga cactggcaaa acaatgcaga    600
```

```
ctttgctttc cttggtcagg cagtataatc caaagatggt caaggtcgca agcttgctgg      660
tgaaaaggac cccacgaagt gttggatata agccagactt tgttggattt gaaattccag      720
acaagtttgt tgtaggatat gcccttgact ataatgaata cttcagggat ttgaatcatg      780
tttgtgtcat tagtgaaact ggaaaagcaa aatacaaagc ctaagatgag agttcaagtt      840
gagtttggaa acatctggag tcctattgac atcgccagta aaattatcaa tgttctagtt      900
ctgtggccat ctgcttagta gagcttttg catgtatctt ctaagaattt tatctgtttt       960
gtactttaga aatgtcagtt gctgcattcc taaactgttt atttgcacta tgagcctata     1020
gactatcagt tcccttgggc ggattgttg tttaacttgt aaatgaaaaa attctcttaa     1080
accacagcac tattgagtga acattgaac tcatatctgt aagaaataaa gagaagatat      1140
attagttttt taattggtat tttaattttt atatatgcag gaaagaatag aagtgattga     1200
atattgttaa ttataccacc gtgtgttaga aaagtaagaa gcagtcaatt ttcacatcaa     1260
agacagcatc taagaagttt tgttctgtcc tggaattatt ttagtagtgt ttcagtaatg     1320
ttgactgtat tttccaactt gttcaaatta ttaccagtga atctttgtca gcagttccct     1380
tttaaatgca aatcaataaa ttcccaaaaa tttaaaaaaa aaaaaaaaaa aaaaa          1435

<210> SEQ ID NO 47
<211> LENGTH: 2395
<212> TYPE: DNA
<213> ORGANISM: Homo sapiens

<400> SEQUENCE: 47
agaggcaggg gctggcctgg gatgcgcgcg cacctgccct cgccccgccc cgcccgcacg       60
aggggtggtg gccgaggccc cgccccgcac gcctcgcctg aggcgggtcc gctcagccca      120
ggcgcccgcc cccgcccccg ccgattaaat gggccggcgg ggctcagccc ccggaaacgg      180
tcgtacactt cggggctgcg agcgcggagg gcgacgacga cgaagcgcag acagcgtcat      240
ggcagagcag gtggccctga ccggacccca ggtgtgcggg atcctgcggg aagagctttt      300
ccagggcgat gccttccatc agtcggatac acacatattc atcatcatgg gtgcatcggg      360
tgacctggcc aagaagaaga tctacccca catctggtgg ctgttccggg atggcctttct      420 gcccgaaaac accttcatcg tgggctatgc ccgttcccgc ctcacagtgg ctgacatccg      480
caaacagagt gagcccttct tcaaggccac cccagaggag aagctcaagc tggaggactt      540
ctttgcccgc aactcctatg tggctggcca gtacgatgat gcagcctcct accagcgcct      600
caacagccac atgaatgccc tccacctggg gtcacaggcc aaccgcctct tctacctggc      660 cttgccccg accgtctacg aggccgtcac caagaacatt cacgagtcct gcatgagcca      720
gataggctga accgcatca tcgtggagaa gcccttcggg agggacctgc agagctctga      780
ccggctgtcc aaccacatct cctccctgtt ccgtgaggac cagatctacc gcatcgacca      840
ctacctgggc aaggagatgg tgcagaacct catggtgctg agatttgcca acaggatctt      900 cggcccatc tggaaccggg acaacatcgc ctgcgttatc ctcaccttca aggagccctt      960
tggcactgag ggtcgcgggg gctatttcga tgaatttggg atcatccggg acgtgatgca     1020
gaaccaccta ctgcagatgc tgtgtctggt ggccatgag aagcccgcct ccaccaactc     1080
agatgacgtc cgtgatgaga aggtcaaggt gttgaaatgc atctcagagg tgcaggccaa     1140
caatgtggtc ctgggccagt acgtggggaa ccccgatgga gagggcgagg ccaccaaagg     1200
gtacctggac gaccccacgg tgccccgcgg gtccaccacc gccacttttg cagccgtcgt     1260
```

| | |
|---|---|
| cctctatgtg gagaatgaga ggtgggatgg ggtgcccttc atcctgcgct gcggcaaggc | 1320 |
| cctgaacgag cgcaaggccg aggtgaggct gcagttccat gatgtggccg gcgacatctt | 1380 |
| ccaccagcag tgcaagcgca acgagctggt gatccgcgtg cagcccaacg aggccgtgta | 1440 |
| caccaagatg atgaccaaga agccgggcat gttcttcaac cccgaggagt cggagctgga | 1500 |
| cctgacctac ggcaacagat acaagaacgt gaagctccct gacgcctacg agcgcctcat | 1560 |
| cctggacgtc ttctgcggga gccagatgca cttcgtgcgc agcgacgagc tccgtgaggc | 1620 |
| ctggcgtatt ttcacccac tgctgcacca gattgagctg gagaagccca gcccatccc | 1680 |
| ctatatttat ggcagccgag gccccacgga ggcagacgag ctgatgaaga gagtgggttt | 1740 |
| ccagtatgag ggcacctaca agtgggtgaa ccccacaag ctctgagccc tgggcaccca | 1800 |
| cctccacccc cgccacggcc accctccttc ccgccgcccg accccgagtc gggaggactc | 1860 |
| cgggaccatt gacctcagct gcacattcct ggccccgggc tctggccacc ctggcccgcc | 1920 |
| cctcgctgct gctactaccc gagcccagct acattcctca gctgccaagc actcgagacc | 1980 |
| atcctggccc ctccagaccc tgcctgagcc caggagctga gtcacctcct ccactcactc | 2040 |
| cagcccaaca gaaggaagga ggagggcgcc cattcgtctg tcccagagct tattggccac | 2100 |
| tgggtctcac tcctgagtgg ggccaggtg ggagggaggg acaaggggga ggaaaggggc | 2160 |
| gagcacccac gtgagagaat ctgcctgtgg ccttgcccgc cagcctcagt gccacttgac | 2220 |
| attccttgtc accagcaaca tctcgagccc ctggatgtc ccctgtccca ccaactctgc | 2280 |
| actccatggc caccccgtgc cacccgtagg cagcctctct gctataagaa aagcagacgc | 2340 |
| agcagctggg acccctccca acctcaatgc cctgccatta aatccgcaaa cagcc | 2395 |

<210> SEQ ID NO 48
<211> LENGTH: 2201
<212> TYPE: DNA
<213> ORGANISM: Homo sapiens

<400> SEQUENCE: 48

| | |
|---|---|
| cgggatttgg gtcgcggttc ttgtttgtgg atcgctgtga tcgtcacttg acaatgcaga | 60 |
| tcttcgtgaa gactctgact ggtaagacca tcaccctcga ggttgagccc agtgacacca | 120 |
| tcgagaatgt caaggcaaag atccaagata aggaaggcat ccctcctgac cagcagaggc | 180 |
| tgatctttgc tggaaaacag ctggaagatg gcgcaccct gtctgactac aacatccaga | 240 |
| aagagtccac cctgcacctg gtgctccgtc tcagaggtgg gatgcaaatc ttcgtgaaga | 300 |
| cactcactgg caagaccatc cccttgagg tggagcccag tgacaccatc gagaacgtca | 360 |
| aagcaaagat ccaggacaag gaaggcattc ctcctgacca gcagaggttg atctttgccg | 420 |
| gaaagcagct ggaagatggg cgcacccgt ctgactacaa catccagaaa gagtctaccc | 480 |
| tgcacctggt gctccgtctc agaggtggga tgcagatctt cgtgaagacc ctgactggta | 540 |
| agaccatcac cctcgaggtg gagcccagta caccatcga gaatgtcaag gcaaagatcc | 600 |
| aagataagga aggcattcct cctgatcagc agaggttgat ctttgccgga aaacagctgg | 660 |
| aagatggtcg taccctgtct gactacaaca tccagaaaga gtccaccttg cacctggtac | 720 |
| tccgtctcag aggtgggatg caaatcttcg tgaagacact cactggcaag accatcaccc | 780 |
| ttgaggtcga gcccagtgac actatcgaga acgtcaaagc aaagatccaa gacaaggaag | 840 |
| gcattcctcc tgaccagcag aggttgatct ttgccgaaaa gcagctggaa gatgggcgca | 900 |
| ccctgtctga ctacaacatc cagaaagagt ctaccctgca cctggtgctc cgtctcagag | 960 |
| gtgggatgca gatcttcgtg aagaccctga ctggtaagac catcaccctc gaagtggagc | 1020 |

```
cgagtgacac cattgagaat gtcaaggcaa agatccaaga caaggaaggc atccctcctg    1080
accagcagag gttgatcttt gccggaaaac agctggaaga tggtcgtacc ctgtctgact    1140
acaacatcca gaaagagtcc accttgcacc tggtgctccg tctcagaggt gggatgcaga    1200
tcttcgtgaa gaccctgact ggtaagacca tcactctcga ggtggagccg agtgacacca    1260
ttgagaatgt caaggcaaag atccaagaca aggaaggcat ccctcctgat cagcagaggt    1320
tgatctttgc tgggaaacag ctggaagatg gacgcaccct gtctgactac aacatccaga    1380
aagagtccac cctgcacctg gtgctccgtc ttagaggtgg gatgcagatc ttcgtgaaga    1440
ccctgactgg taagaccatc actctcgaag tggagccgag tgacaccatt gagaatgtca    1500
aggcaaagat ccaagacaag gaaggcatcc ctcctgacca gcagaggttg atctttgctg    1560
ggaaacagct ggaagatgga cgcaccctgt ctgactacaa catccagaaa gagtccaccc    1620
tgcacctggt gctccgtctt agaggtggga tgcagatctt cgtgaagacc ctgactggta    1680
agaccatcac tctcgaagtg gagccgagtg acaccattga gaatgtcaag gcaaagatcc    1740
aagacaagga aggcatccct cctgaccagc agaggttgat ctttgctggg aaacagctgg    1800
aagatggacg caccctgtct gactacaaca tccagaaaga gtccaccctg cacctggtgc    1860
tccgtctcag aggtgggatg cagatcttcg tgaagaccct gactggtaag accatcaccc    1920
tcgaggtgga gcccagtgac accatcgaga atgtcaaggc aaagatccaa gataaggaag    1980
gcatccctcc tgatcagcag aggttgatct ttgctgggaa acagctggaa gatggacgca    2040
ccctgtctga ctacaacatc cagaaagagt ccactctgca cttggtcctg cgcttgaggg    2100
ggggtgtcta agtttcccct tttaaggttt caacaaattt cattgcactt tcctttcaat    2160
aaagttgttg cattcccaaa aaaaaaaaaa aaaaaaaaa a    2201
```

<210> SEQ ID NO 49  
<211> LENGTH: 1867  
<212> TYPE: DNA  
<213> ORGANISM: Homo sapiens

<400> SEQUENCE: 49

```
ggttcgctgt ggcgggcgcc tgggccgccg gctgtttaac ttcgcttccg ctggcccata      60
gtgatctttg cagtgaccca gcagcatcac tgtttcttgg cgtgtgaaga taacccaagg     120
aattgaggaa gttgctgaga agagtgtgct ggagatgctc taggaaaaaa ttgaatagtg     180
agacgagttc cagcgcaagg gtttctggtt tgccaagaag aaagtgaaca tcatggatca     240
gaacaacagc ctgccacctt acgctcaggg cttggcctcc cctcagggtg ccatgactcc     300
cggaatccct atctttagtc caatgatgcc ttatggcact ggactgaccc cacagcctat     360
tcagaacacc aatagtctgt ctattttgga agagcaacaa aggcagcagc agcaacaaca     420
acagcagcag cagcagcagc agcagcaaca gcaacagcag cagcagcagc agcagcagca     480
gcagcagcag cagcagcagc agcagcagca gcaacaggt gtggcagctg cagccgttca     540
gcagtcaacg tcccagcagg caacacaggg aacctcaggc caggcaccac agctcttcca     600
ctcacagact ctcacaactg cacccttgcc gggcaccact ccactgtatc cctcccccat     660
gactcccatg accccatca ctcctgccac gccagcttcg gagagttctg ggattgtacc     720
gcagctgcaa aatattgtat ccacagtgaa tcttggttgt aaacttgacc taaagaccat     780
tgcacttcgt gcccgaaacg ccgaatataa tcccaagcgg tttgctgcgg taatcatgag     840
gataagagag ccacgaacca cggcactgat tttcagttct gggaaaatgg tgtgcacagg     900
```

```
agccaagagt gaagaacagt ccagactggc agcaagaaaa tatgctagag ttgtacagaa    960
gttgggtttt ccagctaagt tcttggactt caagattcag aatatggtgg ggagctgtga   1020
tgtgaagttt cctataaggt tagaaggcct tgtgctcacc caccaacaat ttagtagtta   1080
tgagccagag ttatttcctg gtttaatcta cagaatgatc aaacccagaa ttgttctcct   1140
tattttgtt tctggaaaag ttgtattaac aggtgctaaa gtcagagcag aaatttatga   1200
agcatttgaa acatctacc ctattctaaa gggattcagg aagacgacgt aatggctctc   1260
atgtacccct gcctccccca cccccttctt ttttttttt taaacaaatc agtttgtttt   1320
ggtacctta aatggtggtg ttgtgagaag atggatgttg agttgcaggg tgtggcacca   1380
ggtgatgccc ttctgtaagt gcccaccgcg ggatgccggg aagggggcatt atttgtgcac   1440
tgagaacacc gcgcagcgtg actgtgagtt gctcataccg tgctgctatc tgggcagcgc   1500
tgcccattta tttatatgta gattttaaac actgctgttg acaagttggt ttgagggaga   1560
aaactttaag tgttaaagcc acctctataa ttgattggac tttttaattt taatgttttt   1620
ccccatgaac cacagttttt atatttctac cagaaaagta aaaatcttt ttaaaagtgt   1680
tgtttttcta atttataact cctaggggtt atttctgtgc cagacacatt ccacctctcc   1740
agtattgcag gacagaatat atgtgttaat gaaaatgaat ggctgtacat atttttttct   1800
ttcttcagag tactctgtac aataaatgca gtttataaaa gtgttaaaaa aaaaaaaaa   1860
aaaaaaa                                                            1867

<210> SEQ ID NO 50
<211> LENGTH: 684
<212> TYPE: PRT
<213> ORGANISM: Homo sapiens

<400> SEQUENCE: 50

Met Ala Arg His Arg Asn Val Arg Gly Tyr Asn Tyr Asp Glu Asp Phe
1               5                   10                  15

Glu Asp Asp Leu Tyr Gly Gln Ser Val Glu Asp Tyr Cys Ile
            20                  25                  30

Ser Pro Ser Thr Ala Ala Gln Phe Ile Tyr Ser Arg Arg Asp Lys Pro
        35                  40                  45

Ser Val Glu Pro Val Glu Tyr Asp Tyr Glu Asp Leu Lys Glu Ser
    50                  55                  60

Ser Asn Ser Val Ser Asn His Gln Leu Ser Gly Phe Asp Gln Ala Arg
65                  70                  75                  80

Leu Tyr Ser Cys Leu Asp His Met Arg Glu Val Leu Gly Asp Ala Val
                85                  90                  95

Pro Asp Glu Ile Leu Ile Glu Ala Val Leu Lys Asn Lys Phe Asp Val
            100                 105                 110

Gln Lys Ala Leu Ser Gly Val Leu Glu Gln Asp Arg Val Gln Ser Leu
        115                 120                 125

Lys Asp Lys Asn Glu Ala Thr Val Ser Thr Gly Lys Ile Ala Lys Gly
    130                 135                 140

Lys Pro Val Asp Ser Gln Thr Ser Arg Ser Glu Ser Glu Ile Val Pro
145                 150                 155                 160

Lys Val Ala Lys Met Thr Val Ser Gly Lys Lys Gln Thr Met Gly Phe
                165                 170                 175

Glu Val Pro Gly Val Ser Ser Glu Glu Asn Gly His Ser Phe His Thr
            180                 185                 190

Pro Gln Lys Gly Pro Pro Ile Glu Asp Ala Ile Ala Ser Ser Asp Val
```

```
              195                 200                 205
Leu Glu Thr Ala Ser Lys Ser Ala Asn Pro His Thr Ile Gln Ala
210                 215                 220

Ser Glu Glu Gln Ser Ser Thr Pro Ala Pro Val Lys Lys Ser Gly Lys
225                 230                 235                 240

Leu Arg Gln Gln Ile Asp Val Lys Ala Glu Leu Lys Arg Gln Gly
            245                 250                 255

Gly Lys Gln Leu Leu Asn Leu Val Val Ile Gly His Val Asp Ala Gly
                260                 265                 270

Lys Ser Thr Leu Met Gly His Met Leu Tyr Leu Leu Gly Asn Ile Asn
            275                 280                 285

Lys Arg Thr Met His Lys Tyr Glu Gln Glu Ser Lys Lys Ala Gly Lys
    290                 295                 300

Ala Ser Phe Ala Tyr Ala Trp Val Leu Asp Glu Thr Gly Glu Glu Arg
305                 310                 315                 320

Glu Arg Gly Val Thr Met Asp Val Gly Met Thr Lys Phe Glu Thr Thr
                325                 330                 335

Thr Lys Val Ile Thr Leu Met Asp Ala Pro Gly His Lys Asp Phe Ile
                340                 345                 350

Pro Asn Met Ile Thr Gly Ala Ala Gln Ala Asp Val Ala Val Leu Val
            355                 360                 365

Val Asp Ala Ser Arg Gly Glu Phe Glu Ala Gly Phe Glu Thr Gly Gly
370                 375                 380

Gln Thr Arg Glu His Gly Leu Leu Val Arg Ser Leu Gly Val Thr Gln
385                 390                 395                 400

Leu Ala Val Ala Val Asn Lys Met Asp Gln Val Asn Trp Gln Gln Glu
                405                 410                 415

Arg Phe Gln Glu Ile Thr Gly Lys Leu Gly His Phe Leu Lys Gln Ala
                420                 425                 430

Gly Phe Lys Glu Ser Asp Val Gly Phe Ile Pro Thr Ser Gly Leu Ser
            435                 440                 445

Gly Glu Asn Leu Ile Thr Arg Ser Gln Ser Ser Glu Leu Thr Lys Trp
450                 455                 460

Tyr Lys Gly Leu Cys Leu Leu Glu Gln Ile Asp Ser Phe Lys Pro Pro
465                 470                 475                 480

Gln Arg Ser Ile Asp Lys Pro Phe Arg Leu Cys Val Ser Asp Val Phe
                485                 490                 495

Lys Asp Gln Gly Ser Gly Phe Cys Ile Thr Gly Lys Ile Glu Ala Gly
                500                 505                 510

Tyr Ile Gln Thr Gly Asp Arg Leu Leu Ala Met Pro Pro Asn Glu Thr
            515                 520                 525

Cys Thr Val Lys Gly Ile Thr Leu His Asp Glu Pro Val Asp Trp Ala
530                 535                 540

Ala Ala Gly Asp His Val Ser Leu Thr Leu Val Gly Met Asp Ile Ile
545                 550                 555                 560

Lys Ile Asn Val Gly Cys Ile Phe Cys Gly Pro Lys Val Pro Ile Lys
                565                 570                 575

Ala Cys Thr Arg Phe Arg Ala Arg Ile Leu Ile Phe Asn Ile Glu Ile
            580                 585                 590

Pro Ile Thr Lys Gly Phe Pro Val Leu Leu His Tyr Gln Thr Val Ser
            595                 600                 605

Glu Pro Ala Val Ile Lys Arg Leu Ile Ser Val Leu Asn Lys Ser Thr
610                 615                 620
```

Gly Glu Val Thr Lys Lys Pro Lys Phe Leu Thr Lys Gly Gln Asn
625                 630                 635                 640

Ala Leu Val Glu Leu Gln Thr Gln Arg Pro Ile Ala Leu Glu Leu Tyr
            645                 650                 655

Lys Asp Phe Lys Glu Leu Gly Arg Phe Met Leu Arg Tyr Gly Gly Ser
            660                 665                 670

Thr Ile Ala Ala Gly Val Val Thr Glu Ile Lys Glu
        675                 680

<210> SEQ ID NO 51
<211> LENGTH: 664
<212> TYPE: PRT
<213> ORGANISM: Homo sapiens

<400> SEQUENCE: 51

Met Ser Gly Val Arg Gly Leu Ser Arg Leu Ser Ala Arg Arg Leu
1               5                   10                  15

Ala Leu Ala Lys Ala Trp Pro Thr Val Leu Gln Thr Gly Thr Arg Gly
            20                  25                  30

Phe His Phe Thr Val Asp Gly Asn Lys Arg Ala Ser Ala Lys Val Ser
            35                  40                  45

Asp Ser Ile Ser Ala Gln Tyr Pro Val Val Asp His Glu Phe Asp Ala
    50                  55                  60

Val Val Val Gly Ala Gly Gly Ala Gly Leu Arg Ala Ala Phe Gly Leu
65                  70                  75                  80

Ser Glu Ala Gly Phe Asn Thr Ala Cys Val Thr Lys Leu Phe Pro Thr
                85                  90                  95

Arg Ser His Thr Val Ala Ala Gln Gly Gly Ile Asn Ala Ala Leu Gly
                100                 105                 110

Asn Met Glu Glu Asp Asn Trp Arg Trp His Phe Tyr Asp Thr Val Lys
            115                 120                 125

Gly Ser Asp Trp Leu Gly Asp Gln Asp Ala Ile His Tyr Met Thr Glu
    130                 135                 140

Gln Ala Pro Ala Ala Val Val Glu Leu Glu Asn Tyr Gly Met Pro Phe
145                 150                 155                 160

Ser Arg Thr Glu Asp Gly Lys Ile Tyr Gln Arg Ala Phe Gly Gly Gln
                165                 170                 175

Ser Leu Lys Phe Gly Lys Gly Gly Gln Ala His Arg Cys Cys Cys Val
                180                 185                 190

Ala Asp Arg Thr Gly His Ser Leu Leu His Thr Leu Tyr Gly Arg Ser
            195                 200                 205

Leu Arg Tyr Asp Thr Ser Tyr Phe Val Glu Tyr Phe Ala Leu Asp Leu
    210                 215                 220

Leu Met Glu Asn Gly Glu Cys Arg Gly Val Ile Ala Leu Cys Ile Glu
225                 230                 235                 240

Asp Gly Ser Ile His Arg Ile Arg Ala Lys Asn Thr Val Val Ala Thr
                245                 250                 255

Gly Gly Tyr Gly Arg Thr Tyr Phe Ser Cys Thr Ser Ala His Thr Ser
                260                 265                 270

Thr Gly Asp Gly Thr Ala Met Ile Thr Arg Ala Gly Leu Pro Cys Gln
            275                 280                 285

Asp Leu Glu Phe Val Gln Phe His Pro Thr Gly Ile Tyr Gly Ala Gly
    290                 295                 300

Cys Leu Ile Thr Glu Gly Cys Arg Gly Glu Gly Gly Ile Leu Ile Asn

```
                305                 310                 315                 320
        Ser Gln Gly Glu Arg Phe Met Glu Arg Tyr Ala Pro Val Ala Lys Asp
                        325                 330                 335

Leu Ala Ser Arg Asp Val Val Ser Arg Ser Met Thr Leu Glu Ile Arg
                        340                 345                 350

Glu Gly Arg Gly Cys Gly Pro Glu Lys Asp His Val Tyr Leu Gln Leu
                        355                 360                 365

His His Leu Pro Pro Glu Gln Leu Ala Thr Arg Leu Pro Gly Ile Ser
                370                 375                 380

Glu Thr Ala Met Ile Phe Ala Gly Val Asp Val Thr Lys Glu Pro Ile
        385                 390                 395                 400

Pro Val Leu Pro Thr Val His Tyr Asn Met Gly Ile Pro Thr Asn
                        405                 410                 415

Tyr Lys Gly Gln Val Leu Arg His Val Asn Gly Gln Asp Gln Ile Val
                        420                 425                 430

Pro Gly Leu Tyr Ala Cys Gly Glu Ala Ala Cys Ala Ser Val His Gly
                        435                 440                 445

Ala Asn Arg Leu Gly Ala Asn Ser Leu Leu Asp Leu Val Val Phe Gly
                450                 455                 460

Arg Ala Cys Ala Leu Ser Ile Glu Glu Ser Cys Arg Pro Gly Asp Lys
        465                 470                 475                 480

Val Pro Pro Ile Lys Pro Asn Ala Gly Glu Glu Ser Val Met Asn Leu
                        485                 490                 495

Asp Lys Leu Arg Phe Ala Asp Gly Ser Ile Arg Thr Ser Glu Leu Arg
                        500                 505                 510

Leu Ser Met Gln Lys Ser Met Gln Asn His Ala Ala Val Phe Arg Val
                        515                 520                 525

Gly Ser Val Leu Gln Glu Gly Cys Gly Lys Ile Ser Lys Leu Tyr Gly
                        530                 535                 540

Asp Leu Lys His Leu Lys Thr Phe Asp Arg Gly Met Val Trp Asn Thr
        545                 550                 555                 560

Asp Leu Val Glu Thr Leu Glu Leu Gln Asn Leu Met Leu Cys Ala Leu
                        565                 570                 575

Gln Thr Ile Tyr Gly Ala Glu Ala Arg Lys Glu Ser Arg Gly Ala His
                        580                 585                 590

Ala Arg Glu Asp Tyr Lys Val Arg Ile Asp Glu Tyr Asp Tyr Ser Lys
                        595                 600                 605

Pro Ile Gln Gly Gln Gln Lys Lys Pro Phe Glu Glu His Trp Arg Lys
                        610                 615                 620

His Thr Leu Ser Tyr Val Asp Val Gly Thr Gly Lys Val Thr Leu Glu
        625                 630                 635                 640

Tyr Arg Pro Val Ile Asp Lys Thr Leu Asn Glu Ala Asp Cys Ala Thr
                        645                 650                 655

Val Pro Pro Ala Ile Arg Ser Tyr
                        660

<210> SEQ ID NO 52
<211> LENGTH: 494
<212> TYPE: PRT
<213> ORGANISM: Homo sapiens

<400> SEQUENCE: 52

Met Pro Arg Val Tyr Ile Gly Arg Leu Ser Tyr Gln Ala Arg Glu Arg
1               5                   10                  15
```

-continued

```
Asp Val Glu Arg Phe Phe Lys Gly Tyr Gly Lys Ile Leu Glu Val Asp
            20                  25                  30

Leu Lys Asn Gly Tyr Gly Phe Val Glu Phe Asp Asp Leu Arg Asp Ala
        35                  40                  45

Asp Asp Ala Val Tyr Glu Leu Asn Gly Lys Asp Leu Cys Gly Glu Arg
    50                  55                  60

Val Ile Val Glu His Ala Arg Gly Pro Arg Arg Asp Gly Ser Tyr Gly
65                  70                  75                  80

Ser Gly Arg Ser Gly Tyr Gly Tyr Arg Arg Ser Gly Arg Asp Lys Tyr
                85                  90                  95

Gly Pro Pro Thr Arg Thr Glu Tyr Arg Leu Ile Val Glu Asn Leu Ser
            100                 105                 110

Ser Arg Cys Ser Trp Gln Asp Leu Lys Asp Tyr Met Arg Gln Ala Gly
        115                 120                 125

Glu Val Thr Tyr Ala Asp Ala His Lys Gly Arg Lys Asn Glu Gly Val
    130                 135                 140

Ile Glu Phe Val Ser Tyr Ser Asp Met Lys Arg Ala Leu Glu Lys Leu
145                 150                 155                 160

Asp Gly Thr Glu Val Asn Gly Arg Lys Ile Arg Leu Val Glu Asp Lys
                165                 170                 175

Pro Gly Ser Arg Arg Arg Ser Tyr Ser Arg Ser Arg Ser His Ser
            180                 185                 190

Arg Ser Arg Ser Arg Ser His Ser Arg Lys Ser Arg Ser Arg Ser
        195                 200                 205

Gly Ser Ser Lys Ser Ser His Ser Lys Ser Arg Ser Arg Ser Arg Ser
    210                 215                 220

Gly Ser Arg Ser Arg Ser Lys Ser Arg Ser Arg Ser Gln Ser Arg Ser
225                 230                 235                 240

Arg Ser Lys Lys Glu Lys Ser Arg Ser Pro Ser Lys Glu Lys Ser Arg
                245                 250                 255

Ser Arg Ser His Ser Ala Gly Lys Ser Arg Ser Lys Ser Lys Asp Gln
            260                 265                 270

Ala Glu Glu Lys Ile Gln Asn Asn Asp Asn Val Gly Lys Pro Lys Ser
        275                 280                 285

Arg Ser Pro Ser Arg His Lys Ser Lys Ser Lys Ser Arg Ser Arg Ser
    290                 295                 300

Gln Glu Arg Arg Val Glu Glu Lys Arg Gly Ser Val Ser Arg Gly
305                 310                 315                 320

Arg Ser Gln Glu Lys Ser Leu Arg Gln Ser Arg Ser Arg Ser Arg Ser
                325                 330                 335

Lys Gly Gly Ser Arg Ser Arg Ser Arg Ser Lys Ser Lys Asp
            340                 345                 350

Lys Arg Lys Gly Arg Lys Arg Ser Arg Glu Glu Ser Arg Ser Arg Ser
        355                 360                 365

Arg Ser Arg Ser Lys Ser Glu Arg Ser Lys Arg Gly Ser Lys Arg
    370                 375                 380

Asp Ser Lys Ala Gly Ser Ser Lys Lys Lys Lys Glu Asp Thr Asp
385                 390                 395                 400

Arg Ser Gln Ser Arg Ser Pro Ser Arg Ser Val Ser Lys Glu Arg Glu
                405                 410                 415

His Ala Lys Ser Glu Ser Ser Gln Arg Glu Gly Arg Gly Glu Ser Glu
            420                 425                 430

Asn Ala Gly Thr Asn Gln Glu Thr Arg Ser Arg Ser Arg Ser Asn Ser
```

```
                    435                 440                 445
Lys Ser Lys Pro Asn Leu Pro Ser Glu Ser Arg Ser Arg Ser Lys Ser
            450                 455                 460
Ala Ser Lys Thr Arg Ser Arg Ser Lys Ser Arg Ser Arg Ser Ala Ser
465                 470                 475                 480
Arg Ser Pro Ser Arg Ser Arg Ser His Ser Arg Ser
                485                 490

<210> SEQ ID NO 53
<211> LENGTH: 376
<212> TYPE: PRT
<213> ORGANISM: Homo sapiens

<400> SEQUENCE: 53

Thr Phe Pro Arg Glu Trp Leu Cys Asp Arg His Leu Arg Glu Lys Met
1               5                  10                  15
Phe Ser Ser Val Ala His Leu Ala Arg Ala Asn Pro Phe Asn Thr Pro
            20                  25                  30
His Leu Gln Leu Val His Asp Gly Leu Gly Asp Leu Arg Ser Ser Ser
        35                  40                  45
Pro Gly Pro Thr Gly Gln Pro Arg Arg Pro Arg Asn Leu Ala Ala Ala
50                  55                  60
Ala Val Glu Glu Tyr Ser Cys Glu Phe Gly Ser Ala Lys Tyr Tyr Ala
65                  70                  75                  80
Leu Cys Gly Phe Gly Val Leu Ser Cys Gly Leu Thr His Thr Ala
                85                  90                  95
Val Val Pro Leu Asp Leu Val Lys Cys Arg Met Gln Val Asp Pro Gln
            100                 105                 110
Lys Tyr Lys Gly Ile Phe Asn Gly Phe Ser Val Thr Leu Lys Glu Asp
        115                 120                 125
Gly Val Arg Gly Leu Ala Lys Gly Trp Ala Pro Thr Phe Leu Gly Tyr
130                 135                 140
Ser Met Gln Gly Leu Cys Lys Phe Gly Phe Tyr Glu Val Phe Lys Val
145                 150                 155                 160
Leu Tyr Ser Asn Met Leu Gly Glu Glu Asn Thr Tyr Leu Trp Arg Thr
                165                 170                 175
Ser Leu Tyr Leu Ala Ala Ser Ala Ser Ala Glu Phe Phe Ala Asp Ile
            180                 185                 190
Ala Leu Ala Pro Met Glu Ala Ala Lys Val Arg Ile Gln Thr Gln Pro
        195                 200                 205
Gly Tyr Ala Asn Thr Leu Arg Asp Ala Ala Pro Lys Met Tyr Lys Glu
210                 215                 220
Glu Gly Leu Lys Ala Phe Tyr Lys Gly Val Ala Pro Leu Trp Met Arg
225                 230                 235                 240
Gln Ile Pro Tyr Thr Met Met Lys Phe Ala Cys Phe Glu Arg Thr Val
                245                 250                 255
Glu Ala Leu Tyr Lys Phe Val Val Pro Lys Pro Arg Ser Glu Cys Ser
            260                 265                 270
Lys Pro Glu Gln Leu Val Val Thr Phe Val Ala Gly Tyr Ile Ala Gly
        275                 280                 285
Val Phe Cys Ala Ile Val Ser His Pro Ala Asp Ser Val Val Ser Val
290                 295                 300
Leu Asn Lys Glu Lys Gly Ser Ser Ala Ser Leu Val Leu Lys Arg Leu
305                 310                 315                 320
```

```
Gly Phe Lys Gly Val Trp Lys Gly Leu Phe Ala Arg Ile Ile Met Ile
                325                 330                 335
Gly Thr Leu Thr Ala Leu Gln Trp Phe Ile Tyr Asp Ser Val Lys Val
            340                 345                 350
Tyr Phe Arg Leu Pro Arg Pro Pro Pro Glu Met Pro Glu Ser Leu
        355                 360                 365
Lys Lys Lys Leu Gly Leu Thr Gln
370                 375

<210> SEQ ID NO 54
<211> LENGTH: 339
<212> TYPE: PRT
<213> ORGANISM: Homo sapiens

<400> SEQUENCE: 54

Met Asp Gln Asn Asn Ser Leu Pro Pro Tyr Ala Gln Gly Leu Ala Ser
1               5                   10                  15
Pro Gln Gly Ala Met Thr Pro Gly Ile Pro Ile Phe Ser Pro Met Met
            20                  25                  30
Pro Tyr Gly Thr Gly Leu Thr Pro Gln Pro Ile Gln Asn Thr Asn Ser
        35                  40                  45
Leu Ser Ile Leu Glu Glu Gln Gln Arg Gln Gln Gln Gln Gln Gln Gln
    50                  55                  60
Gln Gln Gln Gln Gln Gln Gln Gln Gln Gln Gln Gln Gln Gln Gln Gln
65                  70                  75                  80
Gln Gln Gln Gln Gln Gln Gln Gln Gln Gln Gln Gln Gln Gln Gln Ala
                85                  90                  95
Val Ala Ala Ala Val Gln Gln Ser Thr Ser Gln Gln Ala Thr Gln Gly
            100                 105                 110
Gly Thr Ser Gly Gln Ala Pro Gln Leu Phe His Ser Gln Thr Leu Thr
        115                 120                 125
Thr Ala Pro Leu Pro Gly Thr Thr Pro Leu Tyr Pro Ser Pro Met Thr
    130                 135                 140
Pro Met Thr Pro Ile Thr Pro Ala Thr Pro Ala Ser Glu Ser Ser Gly
145                 150                 155                 160
Ile Val Pro Gln Leu Gln Asn Ile Val Ser Thr Val Asn Leu Gly Cys
                165                 170                 175
Lys Leu Asp Leu Lys Thr Ile Ala Leu Arg Ala Arg Asn Ala Glu Tyr
            180                 185                 190
Asn Pro Lys Arg Phe Ala Ala Val Ile Met Arg Ile Arg Glu Pro Arg
        195                 200                 205
Thr Thr Ala Leu Ile Phe Ser Ser Gly Lys Met Val Cys Thr Gly Ala
    210                 215                 220
Lys Ser Glu Glu Gln Ser Arg Leu Ala Ala Arg Lys Tyr Ala Arg Val
225                 230                 235                 240
Val Gln Lys Leu Gly Phe Pro Ala Lys Phe Leu Asp Phe Lys Ile Gln
                245                 250                 255
Asn Met Val Gly Ser Cys Asp Val Lys Phe Pro Ile Arg Leu Glu Gly
            260                 265                 270
Leu Val Leu Thr His Gln Gln Phe Ser Ser Tyr Glu Pro Glu Leu Phe
        275                 280                 285
Pro Gly Leu Ile Tyr Arg Met Ile Lys Pro Arg Ile Val Leu Leu Ile
    290                 295                 300
Phe Val Ser Gly Lys Val Val Leu Thr Gly Ala Lys Val Arg Ala Glu
305                 310                 315                 320
```

```
Ile Tyr Glu Ala Phe Glu Asn Ile Tyr Pro Ile Leu Lys Gly Phe Arg
                325                 330                 335

Lys Thr Thr

<210> SEQ ID NO 55
<211> LENGTH: 55
<212> TYPE: PRT
<213> ORGANISM: Artificial sequence
<220> FEATURE:
<223> OTHER INFORMATION: Synthetic construct

<400> SEQUENCE: 55

Met Gln Ala Pro Arg Ala Ala Leu Val Phe Ala Leu Val Ile Ala Leu
1               5                   10                  15

Val Pro Val Gly Arg Gly Asn Tyr Glu Glu Leu Glu Asn Ser Gly Asp
                20                  25                  30

Thr Thr Val Glu Ser Glu Arg Pro Asn Lys Val Thr Ile Pro Ser Thr
            35                  40                  45

Phe Ala Ala Val Thr Ile Lys
        50                  55

<210> SEQ ID NO 56
<211> LENGTH: 23
<212> TYPE: PRT
<213> ORGANISM: Artificial sequence
<220> FEATURE:
<223> OTHER INFORMATION: Synthetic construct

<400> SEQUENCE: 56

Cys Lys Ile Gln Leu Ser Trp Lys Val Ile Pro Ala Phe Cys Leu Glu
1               5                   10                  15

Ser Ser His Arg Asn Ala Leu

<210> SEQ ID NO 57
<211> LENGTH: 49
<212> TYPE: DNA
<213> ORGANISM: Homo sapiens

<400> SEQUENCE: 57
gtaagccgcc tccacttcct actcctggga aggaggatcg caaaagctg                49

<210> SEQ ID NO 58
<211> LENGTH: 38
<212> TYPE: DNA
<213> ORGANISM: Artificial sequence
<220> FEATURE:
<223> OTHER INFORMATION: Oligonucleotide

<400> SEQUENCE: 58
ctagctagcc accatgcagg ctccccgcgc agccctag                            38

<210> SEQ ID NO 59
<211> LENGTH: 53
<212> TYPE: DNA
<213> ORGANISM: Artificial sequence
<220> FEATURE:
<223> OTHER INFORMATION: Oligonucleotide

<400> SEQUENCE: 59
ttacttgtcg tcatcgtctt tgtagtcgga ttcactgtca cttgggttgt gat           53

<210> SEQ ID NO 60
```

<211> LENGTH: 576
<212> TYPE: DNA
<213> ORGANISM: Artificial sequence
<220> FEATURE:
<223> OTHER INFORMATION: Synthetic construct

<400> SEQUENCE: 60

```
atgcaggctc cccgcgcagc cctagtcttc gccctggtga tcgcgctcgt tcccgtcggc      60
cggggtaatt atgaggaatt agaaaactca ggagatacaa ctgtggaatc tgaaagacca     120
aataaagtga ctattccaag cacatttgct gcagtgacca tcaagaaac attaaatgca     180
aatataaatt ctaccaactt tgctccggat gaaaatcagt tagagtttat actgatggtg     240
ttaatcccat tgattttatt ggtcctctta cttttatccg tggtattcct tgcaacatac     300
tataaaagaa aagaactaa caagaacct tctagccaag gatctcagag tgctttacag     360
acatatgaac tgggaagtga aaacgtgaaa gtccctattt tgaggaaga tacaccctct     420
gttatggaaa ttgaaatgga agagcttgat aaatggatga acagcatgaa tagaaatgcc     480
gactttgaat gtttacctac cttgaaggaa gagaaggaat caaatcacaa cccaagtgac     540
agtgaatccg actacaaaga cgatgacgac aagtaa                              576
```

<210> SEQ ID NO 61
<211> LENGTH: 191
<212> TYPE: PRT
<213> ORGANISM: Artificial sequence
<220> FEATURE:
<223> OTHER INFORMATION: Synthetic construct

<400> SEQUENCE: 61

```
Met Gln Ala Pro Arg Ala Ala Leu Val Phe Ala Leu Val Ile Ala Leu
1               5                   10                  15
Val Pro Val Gly Arg Gly Asn Tyr Glu Glu Leu Glu Asn Ser Gly Asp
                20                  25                  30
Thr Thr Val Glu Ser Glu Arg Pro Asn Lys Val Thr Ile Pro Ser Thr
            35                  40                  45
Phe Ala Ala Val Thr Ile Lys Glu Thr Leu Asn Ala Asn Ile Asn Ser
        50                  55                  60
Thr Asn Phe Ala Pro Asp Glu Asn Gln Leu Glu Phe Ile Leu Met Val
65                  70                  75                  80
Leu Ile Pro Leu Ile Leu Leu Val Leu Leu Leu Ser Val Val Phe
                85                  90                  95
Leu Ala Thr Tyr Tyr Lys Arg Lys Arg Thr Lys Gln Glu Pro Ser Ser
                100                 105                 110
Gln Gly Ser Gln Ser Ala Leu Gln Thr Tyr Glu Leu Gly Ser Glu Asn
            115                 120                 125
Val Lys Val Pro Ile Phe Glu Glu Asp Thr Pro Ser Val Met Glu Ile
        130                 135                 140
Glu Met Glu Glu Leu Asp Lys Trp Met Asn Ser Met Asn Arg Asn Ala
145                 150                 155                 160
Asp Phe Glu Cys Leu Pro Thr Leu Lys Glu Glu Lys Glu Ser Asn His
                165                 170                 175
Asn Pro Ser Asp Ser Glu Ser Asp Tyr Lys Asp Asp Asp Lys
            180                 185                 190
```

<210> SEQ ID NO 62
<211> LENGTH: 19
<212> TYPE: PRT
<213> ORGANISM: Homo sapiens

<400> SEQUENCE: 62

Arg Gly Asn Tyr Glu Glu Leu Glu Asn Ser Gly Asp Thr Thr Val Glu
1               5                   10                  15

Ser Glu Arg

<210> SEQ ID NO 63
<211> LENGTH: 17
<212> TYPE: PRT
<213> ORGANISM: Homo sapiens

<400> SEQUENCE: 63

Tyr Lys Arg Lys Arg Thr Lys Gln Glu Pro Ser Ser Gln Gly Ser Gln
1               5                   10                  15

Ser

<210> SEQ ID NO 64
<211> LENGTH: 232
<212> TYPE: PRT
<213> ORGANISM: Homo sapiens

<400> SEQUENCE: 64

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 65
<211> LENGTH: 217
<212> TYPE: PRT
<213> ORGANISM: Homo sapiens

<400> SEQUENCE: 65

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 66
<211> LENGTH: 233
<212> TYPE: PRT
<213> ORGANISM: Mus musculus

<400> SEQUENCE: 66

```
Glu Pro Arg Gly Pro Thr Ile Lys Pro Cys Pro Pro Cys Lys Cys Pro
1               5                   10                  15

Ala Pro Asn Leu Leu Gly Gly Pro Ser Val Phe Ile Phe Pro Pro Lys
            20                  25                  30

Ile Lys Asp Val Leu Met Ile Ser Leu Ser Pro Ile Val Thr Cys Val
        35                  40                  45

Val Val Asp Val Ser Glu Asp Asp Pro Asp Val Gln Ile Ser Trp Phe
50                  55                  60

Val Asn Asn Val Glu Val His Thr Ala Gln Thr Gln Thr His Arg Glu
65                  70                  75                  80

Asp Tyr Asn Ser Thr Leu Arg Val Val Ser Ala Leu Pro Ile Gln His
                85                  90                  95

Gln Asp Trp Met Ser Gly Lys Glu Phe Lys Cys Lys Val Asn Asn Lys
            100                 105                 110

Asp Leu Pro Ala Pro Ile Glu Arg Thr Ile Ser Lys Pro Lys Gly Ser
        115                 120                 125

Val Arg Ala Pro Gln Val Tyr Val Leu Pro Pro Pro Glu Glu Glu Met
130                 135                 140
```

```
Thr Lys Lys Gln Val Thr Leu Thr Cys Met Val Asp Phe Met Pro
145                 150                 155                 160

Glu Asp Ile Tyr Val Glu Trp Thr Asn Asn Gly Lys Thr Glu Leu Asn
            165                 170                 175

Tyr Lys Asn Thr Glu Pro Val Leu Asp Ser Asp Gly Ser Tyr Phe Met
        180                 185                 190

Tyr Ser Lys Leu Arg Val Glu Lys Lys Asn Trp Val Glu Arg Asn Ser
            195                 200                 205

Tyr Ser Cys Ser Val Val His Glu Gly Leu His Asn His His Thr Thr
        210                 215                 220

Lys Ser Phe Ser Arg Thr Pro Gly Lys
225                 230

<210> SEQ ID NO 67
<211> LENGTH: 2
<212> TYPE: PRT
<213> ORGANISM: Homo sapiens

<400> SEQUENCE: 67

Gly Ser
1

<210> SEQ ID NO 68
<211> LENGTH: 4
<212> TYPE: PRT
<213> ORGANISM: Homo sapiens

<400> SEQUENCE: 68

Gly Ser Gly Ser
1

<210> SEQ ID NO 69
<211> LENGTH: 2
<212> TYPE: PRT
<213> ORGANISM: Homo sapiens

<400> SEQUENCE: 69

Ala Ser
1

<210> SEQ ID NO 70
<211> LENGTH: 4
<212> TYPE: PRT
<213> ORGANISM: Homo sapiens

<400> SEQUENCE: 70

Gly Gly Gly Ser
1

<210> SEQ ID NO 71
<211> LENGTH: 15
<212> TYPE: PRT
<213> ORGANISM: Homo sapiens

<400> SEQUENCE: 71

Gly Gly Gly Gly Ser Gly Gly Gly Gly Ser Gly Gly Gly Gly Ser
1               5                   10                  15

<210> SEQ ID NO 72
<211> LENGTH: 20
<212> TYPE: PRT
<213> ORGANISM: Homo sapiens
```

```
<400> SEQUENCE: 72

Gly Gly Gly Gly Ser Gly Gly Gly Gly Ser Gly Gly Gly Gly Ser Gly
1               5                   10                  15

Gly Gly Gly Ser
            20
```